United States Patent
Piron et al.

(10) Patent No.: US 9,814,390 B2
(45) Date of Patent: Nov. 14, 2017

(54) INSERT IMAGING DEVICE FOR SURGICAL PROCEDURES

(71) Applicants: Cameron Piron, Toronto (CA); Michael Wood, Toronto (CA); Murugathas Yuwaraj, Markham (CA); Alex Panther, Toronto (CA); Nishanthan Shanmugaratnam, Scarborough (CA); William Lau, Toronto (CA); Monroe M. Thomas, Toronto (CA); Gal Sela, Toronto (CA); Joshua Richmond, Toronto (CA); Wes Hodges, London (CA); Simon Alexander, Toronto (CA); David Gallop, Toronto (CA)

(72) Inventors: Cameron Piron, Toronto (CA); Michael Wood, Toronto (CA); Murugathas Yuwaraj, Markham (CA); Alex Panther, Toronto (CA); Nishanthan Shanmugaratnam, Scarborough (CA); William Lau, Toronto (CA); Monroe M. Thomas, Toronto (CA); Gal Sela, Toronto (CA); Joshua Richmond, Toronto (CA); Wes Hodges, London (CA); Simon Alexander, Toronto (CA); David Gallop, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 15 days.

(21) Appl. No.: 14/777,300

(22) PCT Filed: Mar. 14, 2014

(86) PCT No.: PCT/CA2014/000254
§ 371 (c)(1),
(2) Date: Sep. 15, 2015

(87) PCT Pub. No.: WO2014/138923
PCT Pub. Date: Sep. 18, 2014

(65) Prior Publication Data
US 2016/0022146 A1    Jan. 28, 2016

Related U.S. Application Data

(60) Provisional application No. 61/801,746, filed on Mar. 15, 2013, provisional application No. 61/801,143, (Continued)

(51) Int. Cl.
*A61B 5/05*    (2006.01)
*A61B 5/00*    (2006.01)
(Continued)

(52) U.S. Cl.
CPC .......... *A61B 5/0035* (2013.01); *A61B 5/0059* (2013.01); *A61B 5/055* (2013.01);
(Continued)

(58) Field of Classification Search
CPC .. A61B 5/6865; A61B 17/3423; G01R 33/34; G01R 33/34084
See application file for complete search history.

(56) References Cited

U.S. PATENT DOCUMENTS

| 4,932,411 A | 6/1990 | Fritschy |
| 5,050,607 A | 9/1991 | Bradley et al. |

(Continued)

FOREIGN PATENT DOCUMENTS

| WO | 9838907 A1 | 9/1998 |
| WO | 0025673 A1 | 5/2000 |

(Continued)

OTHER PUBLICATIONS

International Search Report (PCT/CA2014/000254) dated Aug. 7, 2014.
(Continued)

*Primary Examiner* — Tse Chen
*Assistant Examiner* — Jason Ip
(74) *Attorney, Agent, or Firm* — Hill & Schumacher

(57) ABSTRACT

Insertable imaging devices, and methods of use thereof in minimally invasive medical procedures, are described. In some embodiments, insertable imaging devices are described that can be introduced and removed from an access port without disturbing or risking damage to internal tissue. In some embodiments, imaging devices are integrated into an access port, thereby allowing imaging of internal tissues within the vicinity of the access port, while, for example, enabling manipulation of surgical tools in the
(Continued)

surgical field of interest. In other embodiments, imaging devices are integrated into an imaging sleeve that is insertable into an access port. Several example embodiments described herein provide imaging devices for performing imaging within an access port, where the imaging may be based one or more imaging modalities that may include, but are not limited to, magnetic resonance imaging, ultrasound, optical imaging such as hyperspectral imaging and optical coherence tomography, and electrical conductive measurements.

5 Claims, 91 Drawing Sheets

Related U.S. Application Data filed on Mar. 15, 2013, provisional application No. 61/800,787, filed on Mar. 15, 2013, provisional application No. 61/800,911, filed on Mar. 15, 2013, provisional application No. 61/800,155, filed on Mar. 15, 2013, provisional application No. 61/818,255, filed on May 1, 2013, provisional application No. 61/818,325, filed on May 1, 2013, provisional application No. 61/924,993, filed on Jan. 8, 2014.

(51) Int. Cl.
*A61B 5/055* (2006.01)
*G01R 33/34* (2006.01)
*G01R 33/345* (2006.01)
*A61B 8/12* (2006.01)
*A61B 8/00* (2006.01)
*A61B 17/34* (2006.01)
*A61B 8/08* (2006.01)
*A61B 90/00* (2016.01)
*A61B 34/20* (2016.01)

(52) U.S. Cl.
CPC .......... *A61B 5/6847* (2013.01); *A61B 5/6865* (2013.01); *A61B 8/12* (2013.01); *A61B 8/4245* (2013.01); *A61B 8/445* (2013.01); *A61B 17/3423* (2013.01); *A61B 90/39* (2016.02); *G01R 33/3456* (2013.01); *G01R 33/34084* (2013.01); *A61B 5/0051* (2013.01); *A61B 8/4254* (2013.01); *A61B 8/4483* (2013.01); *A61B 8/483* (2013.01); *A61B 2017/3454* (2013.01); *A61B 2034/2055* (2016.02); *A61B 2090/374* (2016.02); *A61B 2090/3735* (2016.02); *A61B 2090/3762* (2016.02); *A61B 2090/3782* (2016.02); *A61B 2560/0443* (2013.01); *A61B 2562/04* (2013.01); *A61B 2562/247* (2013.01)

(56) References Cited

U.S. PATENT DOCUMENTS

| 5,170,789 | A | 12/1992 | Narayan |
|---|---|---|---|
| 5,211,165 | A | 5/1993 | Dumoulin et al. |
| 5,348,010 | A | 9/1994 | Schnall et al. |
| 5,476,095 | A | 12/1995 | Schnall et al. |
| 5,699,801 | A | 12/1997 | Atalar et al. |
| 5,928,145 | A | 7/1999 | Ocali et al. |
| 6,026,316 | A | 2/2000 | Kucharczyk et al. |
| 6,051,974 | A | 4/2000 | Reisker et al. |
| 6,236,205 | B1 | 5/2001 | Lüdeke et al. |
| 6,317,091 | B1 | 11/2001 | Oppelt |
| 6,377,836 | B1 | 4/2002 | Arakawa et al. |
| 6,470,204 | B1 | 10/2002 | Uzgiris et al. |
| 6,549,800 | B1 | 4/2003 | Atalar et al. |
| 6,628,980 | B2 | 9/2003 | Atalar |
| 6,832,108 | B2 | 12/2004 | deSouza |
| 7,599,729 | B2 | 10/2009 | Atalar et al. |
| 7,604,875 | B2 | 10/2009 | Wagner |
| 7,606,612 | B2 | 10/2009 | Hillenbrand et al. |
| 7,894,876 | B2 | 2/2011 | von Rueckmann et al. |
| 8,070,682 | B2 | 12/2011 | Zhu |
| 8,144,410 | B2 | 3/2012 | Yazdanfar et al. |
| 8,211,083 | B2 | 7/2012 | Broaddus et al. |
| 8,439,830 | B2 | 5/2013 | McKinley et al. |
| 2002/0079996 | A1 | 6/2002 | Zhang |
| 2003/0187347 | A1* | 10/2003 | Nevo .................... A61B 5/06 600/424 |
| 2005/0049624 | A1* | 3/2005 | Francese ............ A61B 17/3421 606/185 |
| 2008/0109026 | A1 | 5/2008 | Kassam |
| 2008/0177183 | A1 | 7/2008 | Courtney et al. |
| 2009/0048622 | A1 | 2/2009 | Wilson |
| 2010/0113919 | A1 | 5/2010 | Maschke |
| 2010/0256480 | A1 | 10/2010 | Bottomley et al. |
| 2011/0121833 | A1 | 5/2011 | Sambandamurthy et al. |
| 2011/0215807 | A1 | 9/2011 | Misic et al. |
| 2012/0071748 | A1 | 3/2012 | Mark et al. |
| 2012/0133363 | A1 | 5/2012 | Mareci et al. |
| 2012/0184844 | A1 | 7/2012 | Gielen et al. |
| 2012/0203095 | A1 | 8/2012 | Krieger et al. |
| 2012/0242337 | A1 | 9/2012 | Krieger |
| 2012/0253375 | A1 | 10/2012 | Mark et al. |
| 2012/0289816 | A1 | 11/2012 | Mark et al. |
| 2012/0296198 | A1 | 11/2012 | Robinson et al. |
| 2012/0316429 | A1 | 12/2012 | Schmidt et al. |
| 2013/0102851 | A1 | 4/2013 | Mark et al. |
| 2013/0102886 | A1 | 4/2013 | Mark et al. |
| 2013/0204095 | A1 | 8/2013 | Mark et al. |
| 2013/0204287 | A1 | 8/2013 | Mark et al. |
| 2014/0171873 | A1 | 6/2014 | Mark |

FOREIGN PATENT DOCUMENTS

| WO | 03093851 A1 | 11/2003 |
|---|---|---|
| WO | 2012003211 A1 | 1/2012 |

OTHER PUBLICATIONS

Written Opinion (PCT/CA2014/000254) dated Aug. 7, 2014.
Strick et al., Conf Proc IEEE Eng Med Biol Soc. 2008 ; 2008: 2047-2050.
Atalar et al., Magn Reson Med. Oct. 1996;36(4):596-605.
International Preliminary Report on Patentability dated Jul. 15, 2015.
Anderson, Kevan JT et al.,"Forward-Looking Intravascular Orthogonal-Solenoid Coil for Imaging and Guidance in Occlusive Arterial Disease", Magnetic Resonance in Medicine, vol. 60, No. 2, Aug. 1, 2008, pp. 489-491.
European Search Report from EP2967423 dated Apr. 7, 2017.

* cited by examiner

RECESS IS KEYED TO
PROTUBERANCE IN ORDER TO
ENFORCE RELATIVE PROBE
ALIGNMENT DURING INSERTION

Simplified Neurosurgical Configuration

Stripline Resonators in Radial Configuration

Loop coil oriented sideways within a probe

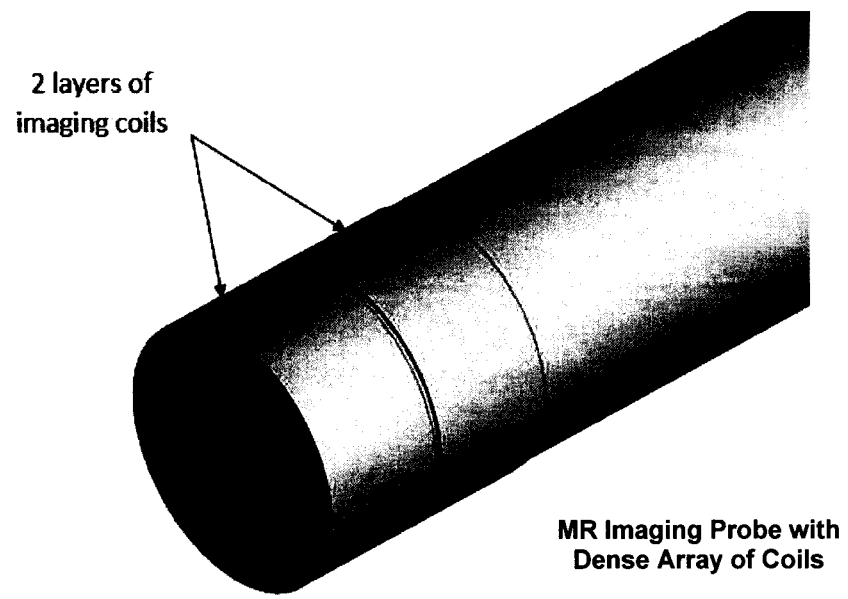
MR Imaging Probe with Dense Array of Coils
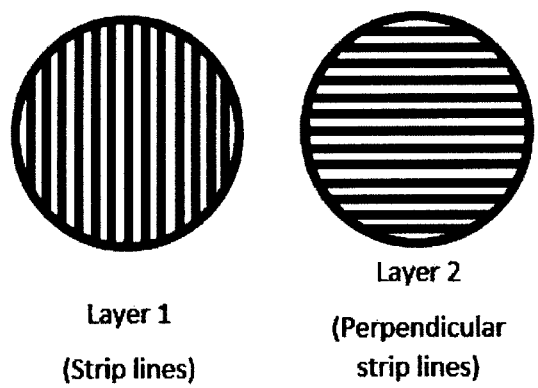
Layer 1
(Strip lines)
Layer 2
(Perpendicular strip lines)
FIG. 25

MR Probe with Swivelling Tip

MR Probe with Wrist and Rotatable Tip

3302

Probe showing correct positioning relative to the B₀ field

Access Port with Integrated MR Coil Configurations

Insertable MR Probe with
Spherical Magnet that
Generates $B_0$ Field

Insertable Ultrasonic Imaging Probe with Singular Circular Transducer

Insertable Ultrasonic Imaging Probe with Radially Array Transducer Elements

Insertable Ultrasonic Imaging Probe with Singular Circular Transducer with Middle Ultrasound transducer
Placement
(single, array and array
with tool access
opening)

Insertable Ultrasonic Imaging Probe with Single Radial Array of Ultrasound Transducers such that Optical View is not Occluded.

Insertable Ultrasonic Imaging Probe with Combined Ultrasonic Transducers Having Opening & Non-Conical tip

FIG. 54A-C

Fibers or light guides in insertable
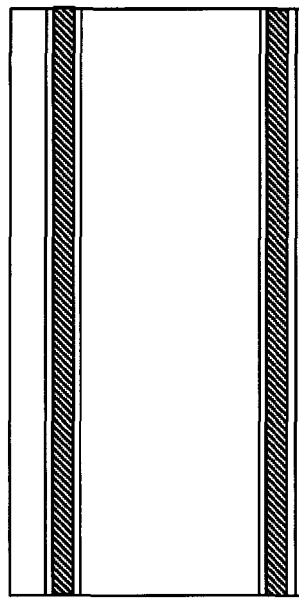
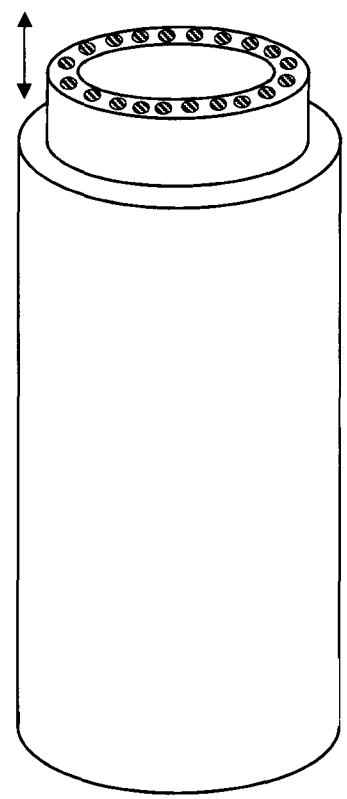
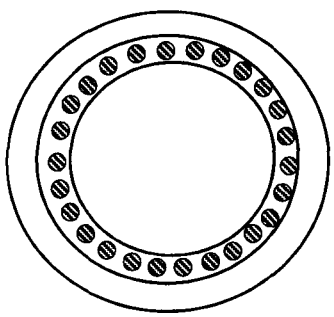
FIG. 59

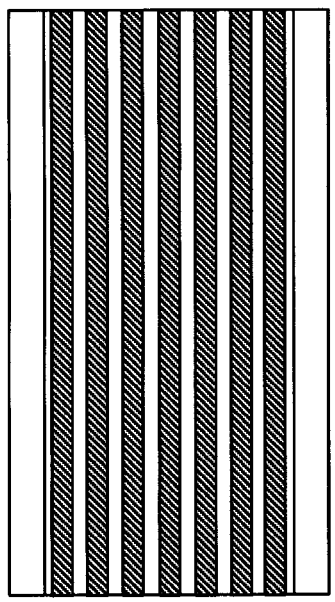
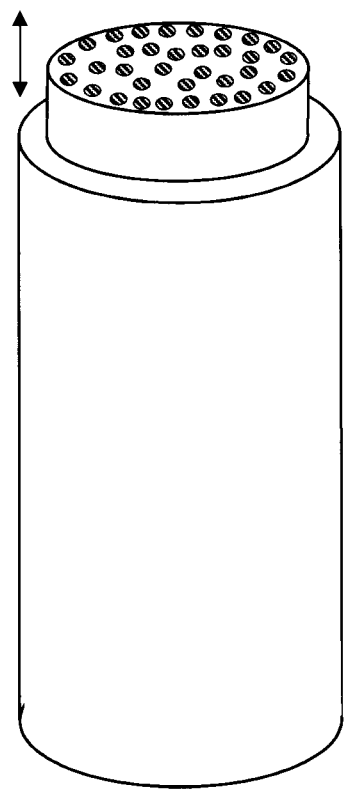
Fibers or light guides in insert device
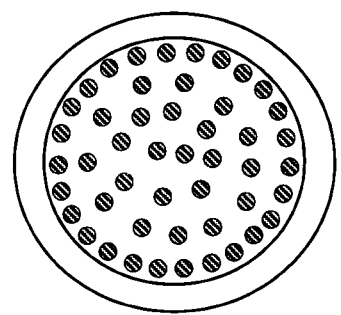
FIG. 60

FIG. 63A-D

Insert Imaging Devices with Differing Imaging Fields and Resolutions

Probe with Insert Imaging Arrays in Different Configurations

INSERT IMAGING DEVICE FOR SURGICAL PROCEDURES

CROSS-REFERENCE TO RELATED APPLICATION

This application is a National Phase application claiming the benefit of the international PCT Patent Application No. PCT/CA2014/000254, filed on Mar. 14, 2014, in English, which claims priority to U.S. Provisional Application No. 61/801,746, titled "INSERT IMAGING DEVICE" and filed on Mar. 15, 2013, the entire contents of which are incorporated herein by reference.

This application claims priority to U.S. Provisional Application No. 61/801,746, titled "INSERT IMAGING DEVICE" and filed on Mar. 15, 2013, the entire contents of which is incorporated herein by reference. This application also claims priority to U.S. Provisional Application No. 61/818,255, titled "INSERT IMAGING DEVICE" and filed on May 1, 2013, the entire contents of which is incorporated herein by reference. This application also claims priority to U.S. Provisional Application No. 61/801,143, titled "INSERTABLE MAGNETIC RESONANCE IMAGING COIL PROBE FOR MINIMALLY INVASIVE CORRIDOR-BASED PROCEDURES" and filed on Mar. 15, 2013, the entire contents of which is incorporated herein by reference. This application also claims priority to U.S. Provisional Application No. 61/818,325, titled "INSERTABLE MAGNETIC RESONANCE IMAGING COIL PROBE FOR MINIMALLY INVASIVE CORRIDOR-BASED PROCEDURES" and filed on May 1, 2013, the entire contents of which is incorporated herein by reference. This application also claims priority to U.S. Provisional Application No. 61/800,787, titled "POLARIZED LIGHT IMAGING DEVICE" and filed on Mar. 15, 2013, the entire contents of which is incorporated herein by reference. This application also claims priority to U.S. Provisional Application No. 61/800,911, titled "HYPERSPECTRAL IMAGING DEVICE" and filed on Mar. 15, 2013, the entire contents of which is incorporated herein by reference. This application also claims priority to U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013, the entire contents of which is incorporated herein by reference. This application also claims priority to U.S. Provisional Application No. 61/924,993, titled "PLANNING, NAVIGATION AND SIMULATION SYSTEMS AND METHODS FOR MINIMALLY INVASIVE THERAPY" and filed Jan. 8, 2014, the entire contents of which is incorporated herein by reference.

BACKGROUND

The present disclosure is generally related to image guided medical procedures.

In the field of surgery, imaging and imaging guidance is becoming a more significant component of clinical care, from diagnosis of disease, monitoring of the disease, planning of the surgical approach, guidance during the procedure and follow-up after the procedure is complete, or as part of a multi-faceted treatment approach.

Integration of imaging data in the surgical suite has become common-place for neurosurgery, where typically brain tumors are excised through an open craniotomy approach guided by imaging. The data that is used typically consists of CT scans with or without associated contrast (iodinated contrast), and MRI scans with or without associated contrast (gadolinium contrast). Systems provide a means to register the imaging data sets together, and registration methods to translate the three dimensional imaging space to the three dimensional space of the patient and tracking of instruments relative to the patient and the associate imaging data by way of an external hardware system such as a mechanical arm, or an RF or optical tracking device.

SUMMARY

Insertable imaging devices, and methods of use thereof in minimally invasive medical procedures, are described. In some embodiments, insertable imaging devices are described that can be introduced and removed from an access port without disturbing or risking damage to internal tissue. In some embodiments, imaging devices are integrated into an access port, thereby allowing imaging of internal tissues within the vicinity of the access port, while, for example, enabling manipulation of surgical tools in the surgical field of interest. In other embodiments, imaging devices are integrated into an imaging sleeve that is insertable into an access port. Several example embodiments described herein provide imaging devices for performing imaging within an access port, where the imaging may be based one or more imaging modalities that may include, but are not limited to, magnetic resonance imaging, ultrasound, optical imaging such as hyperspectral imaging and optical coherence tomography, and electrical conductive measurements.

Accordingly, in one aspect, there is provided a magnetic resonance imaging probe comprising:
  a longitudinal body;
  first and second magnetic resonance coils supported by said longitudinal body;
  wherein said first coil is configured to measure fields having a first direction within a region of interest beyond a distal portion of said longitudinal body;
  wherein said second coil is configured to measure fields having a second direction within a region of interest beyond a distal portion of said longitudinal body, wherein said first direction and said second direction are approximately orthogonal;
  and
  electrical circuits housed within said longitudinal body for tuning and matching said first and second coils and preamplifying signals detected by said first and second coils.

In another aspect, there is provided a magnetic resonance imaging probe comprising:
  a longitudinal body;
  one or more magnetic resonance coil arrays supported by said longitudinal body, wherein at least one coil array is a planar stripline array comprising:
    an array of parallel stripline conductors provided near a distal portion of said longitudinal body, wherein said array of parallel stripline conductors lies in a plane that is approximately orthogonal to a longitudinal axis of said longitudinal body;
    each stripline conductor having longitudinal conductive paths extending from ends thereof and contacting a coil loop at a location that is remote from said distal portion; and
    a tuning capacitor serially provided within each longitudinal conductive path; and a plurality of matching and preamplification circuits housed within said longitudinal body, wherein each matching and preamplification circuits is operatively coupled to a single stripline conductor.

In another aspect, there is provided a magnetic resonance imaging probe comprising:
a longitudinal body;
one or more magnetic resonance coil arrays supported by said longitudinal body, wherein at least one coil array is an axial stripline array comprising:
an array of parallel stripline conductors cylindrically arranged and extending in a longitudinal direction;
each stripline conductor having radial conductive paths extending from ends thereof and contacting an inner ground conductor; and
a tuning capacitor serially provided within each longitudinal conductive path; and
a plurality of matching and preamplification circuits housed within said longitudinal body, wherein each matching and preamplification circuits is operatively coupled to a single stripline conductor.

In another aspect, there is provided a magnetic resonance imaging probe comprising:
a longitudinal body portion comprising one or more magnetic resonance imaging coils;
a handle portion that is removably connectable to said longitudinal body portion, wherein an electrical connection is formed between said longitudinal body portion and said handle portion upon mechanical connection of said longitudinal body portion to said handle portion;
at least one electrical circuit for tuning and matching said coils and preamplifying signals detected by said coils, wherein said electrical circuit is divided among said longitudinal body portion and said handle portion, and wherein at least a preamplification portion of said electrical circuit is housed within said handle portion.

In another aspect, there is provided a magnetic resonance imaging probe comprising:
a longitudinal body;
one or more magnetic resonance coils housed within said longitudinal body, wherein at least one coil is a folded stripline coil comprising:
two longitudinal stripline conductors having a ground plane conductor provided therebetween;
a folded conductor segment connecting said two longitudinal stripline conductors near a distal portion of said longitudinal body;
a pair of matching capacitors, each matching capacitor provided between one of said longitudinal stripline conductors and said ground plane conductor;
a tuning capacitor serially provided within one of said longitudinal stripline conductors; and
a preamplifier circuit housed within said longitudinal body, wherein said preamplifier circuit is operatively coupled to said folded stripline coil.

In another aspect, there is provided a magnetic resonance imaging probe for performing intraoperative imaging during a minimally invasive medical procedure involving an access port, the probe comprising:
a probe body comprising a cylindrical body portion configured to be slidably and removably received within an inner lumen of the access port, said cylindrical body portion comprising one or more magnetic resonance imaging coils;
at least one electrical circuit housed within said probe body for tuning and matching said coils and preamplifying signals detected by said coils; and
one or more air passage features provided on or with said cylindrical body portion for facilitating expulsion of air from the inner lumen of the access port during insertion of said cylindrical body portion into the access port.

In another aspect, there is provided an access port for performing intraoperative imaging during a minimally invasive medical procedure while providing access to internal tissue, the access port comprising:
a hollow cylindrical body configured to be inserted into a subject for providing access to internal tissue;
one or more imaging elements integrated with and supported by said hollow cylindrical body;
one or more externally accessible connectors positioned near a proximal region of said hollow cylindrical body; and
at least one connection channel integrated with said hollow cylindrical body for supporting signal transmission between said externally accessible connectors and said imaging elements;
wherein at least one of said imaging elements is configured for imaging a distal region of interest beyond a distal end of said hollow cylindrical body.

In another aspect, there is provided an imaging sleeve for performing intraoperative imaging during a minimally invasive medical procedure involving an access port, the imaging sleeve comprising:
a hollow cylindrical body configured to be slidably and removably received within an inner lumen of the access port;
one or more imaging elements integrated with and supported by said hollow cylindrical body, wherein said imaging elements are positioned for imaging through the access port;
one or more externally accessible connectors positioned near a proximal region of said hollow cylindrical body; and
at least one connection channel integrated with said hollow cylindrical body for supporting signal transmission between said externally accessible connectors and said imaging elements.

In another aspect, there is provided an
A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 25 illustrates an example implementation of an insertable MR imaging probe having a dense array of coils.

FIG. 59 illustrates light guides in insertable sleeve.

FIG. 60 illustrates light guides in insert device.

DETAILED DESCRIPTION

Figure 1:
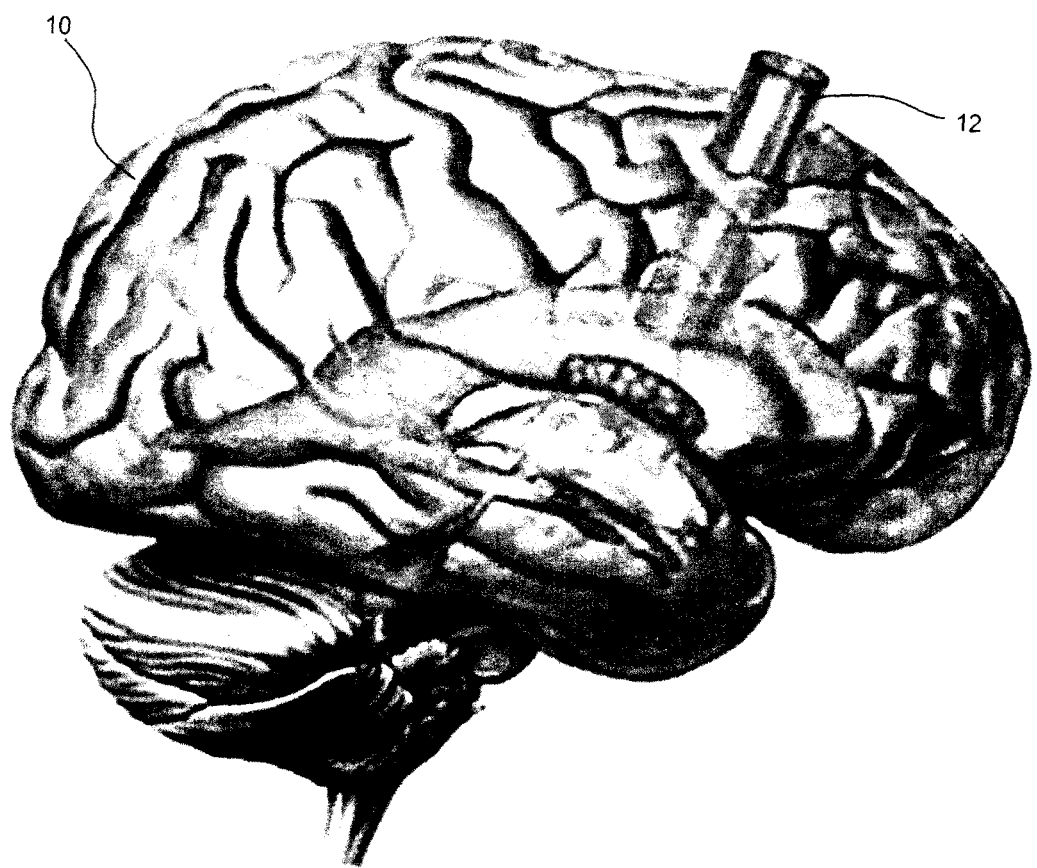
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial access port which may be employed in neurological procedures in order to provide access to internal tissue pathologies, such as tumors. One example of an intracranial access port is the BrainPath surgical access port provided by NICO, which may be inserted into the brain via an obturator with an atraumatic tip in the brain. Such an access port may be employed during a surgical procedure, by inserting the access port, via the obturator that is received within the access port, through the white matter fibers of the brain to access a surgical site.

For example, FIG. 1 shows an access port 12 inserted into a human brain 10, providing access to internal brain tissue. Surgical tools and instruments may then be inserted within the lumen of the access port in order to perform surgical, diagnostic or therapeutic procedures, such as resecting tumors as necessary. This approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

As noted above, some embodiments of the present disclosure provide insertable imaging devices that may be employed during such access-port-based procedures. The use of imaging devices within an access port, or the incorporation of imaging devices into an access port, provides additional interoperative images and data that may improve the accuracy, efficiency, and effectiveness of medical procedures. In some embodiments, methods and devices are described for performing imaging with an insertable imaging device that can be introduced and removed from an access port without disturbing or risking damage to internal tissue. In some embodiments, devices are integrated into an access port, thereby allowing imaging of internal tissues within the vicinity of the access port, while, for example, enabling manipulation of surgical tools in the surgical field of interest. Several example embodiments described herein provide imaging devices for performing imaging within an access port, where the imaging may be based one or more imaging modalities that may include, but are not limited to, magnetic resonance imaging, ultrasound, optical imaging such as hyperspectral imaging and optical coherence tomography, and electrical conductive measurements.

For example, in some embodiments, insertable imaging devices may simultaneously accommodate multiple imaging modalities. Insertable imaging devices according to the present disclosure can be also be integrated into currently available (e.g. conventional) imaging systems, such as MRI scanners, or may be interfaced with a dedicated imaging system. In other embodiments, insertable imaging devices may be configured to accommodate point measurement devices and modalities such as, but not limited to, a Raman touch probe and conductance or pressure measurement (e.g. involving measurements made at a single point or across an array of sensors).

It is to be understood that while many of the embodiments described herein relate to access-port-based neurological procedures, the embodiments provided herein, unless otherwise stated, may be employed for a wide range of medical procedures, involving a wide range of anatomical regions of the body. For example, various embodiments may be employed for imaging during procedures such as endorectal and endovaginal procedures. Furthermore, while many of the embodiments of the present disclosure relate to access-port-based procedures, some embodiments, such as insertable imaging probes described herein, may be employed with or without an access port.

As describe below, an insertable imaging device may, in some embodiments, include at least one imaging array employing at least one imaging modality. Examples of imaging modalities include magnetic resonance MR imaging, ultrasound, optical imaging (such as, but not limited to visible 2D-3D imaging, optical coherence tomography, hyper-spectral imaging, polarized light imaging, Raman Imaging, and fluorescence Imaging), electrophysiology, optical coherence tomography, X-ray (computerized tomography, spectral X-ray), photo-acoustic imaging, positron emission tomography, thermal imaging, electromechanical arrays (strain gauges, ionic conductors), and biosensor arrays. It will also be understood that these modalities may be used in receive and/or transmission mode, and may be used in conjunction with an external transmission or receiving system, and image processing system. Some embodiments may include a means to transmit the signals to and from the detectors/transmitters and coordinate the image acquisition, and image alignment. Some embodiments may also include a means to integrate the acquired information with a previously acquired volumetric image data.

The present disclosure is organized as follows. Section 1 presents various embodiments of insertable imaging device that are generic to a wide range of imaging modalities, where the generic embodiments include insertable imaging probes, access ports with integrated imaging elements, and embodiments involving various combinations of insertable imaging probes and access ports with integrated imaging elements. Section 2 describes various embodiments of insertable imaging probes and access ports with integrated imaging elements that are configured for magnetic resonance imaging. Additional sections of the present disclosure describe additional imaging modalities, and embodiments involving multimodal imaging.

1. Insertable Imaging Devices 1.1 Insertable Imaging Probe

Figure 2A:
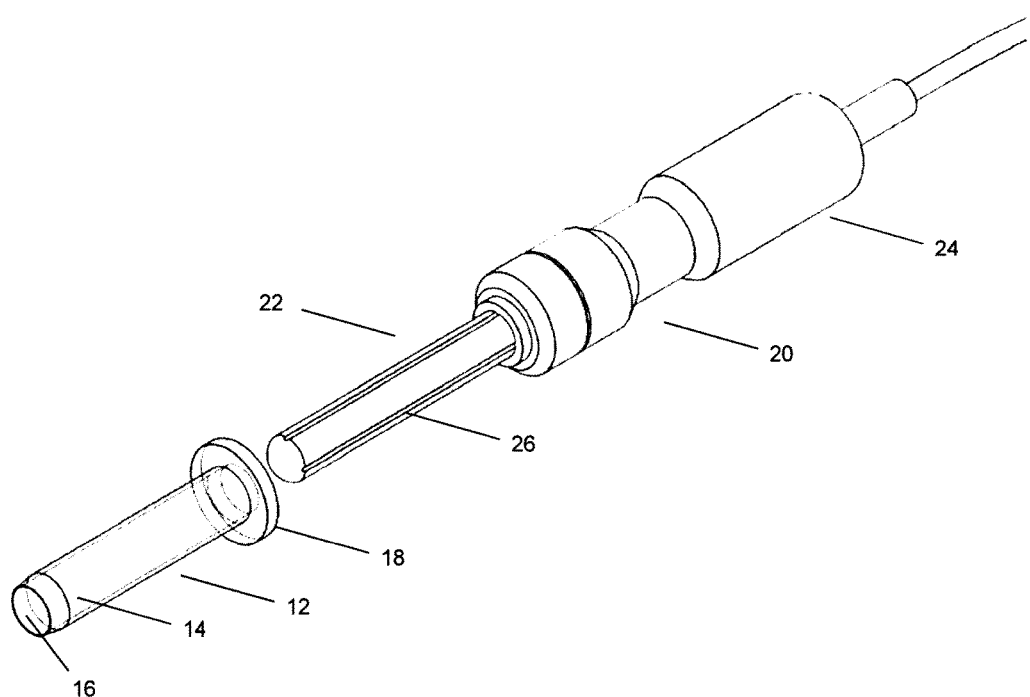
FIGS. 2A and 2B illustrate an example implementation of an insertable imaging probe that is insertable into an access port, showing the device (A) prior to insertion and (B) after insertion.
Figure 2B:
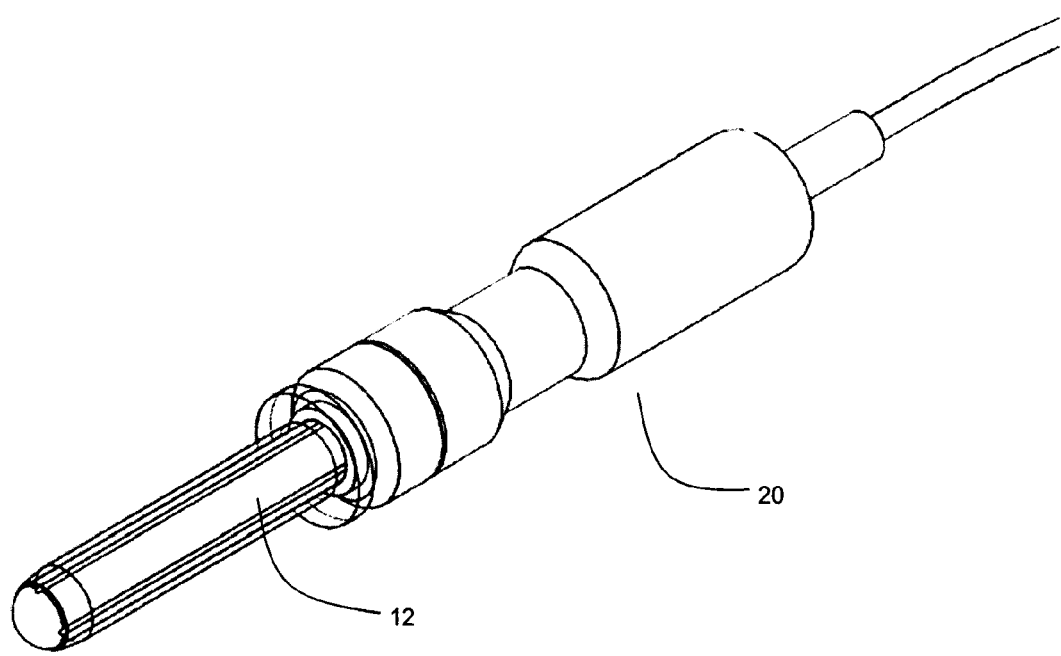

In some embodiments, an insertable imaging probe is provided that is insertable into an access port. FIGS. 2A and 2B illustrate an example implementation of such an embodiment, in which an insertable imaging probe is shown in FIG. 2A prior to insertion into an access port, and FIG. 2B after insertion into the bore of the access port. As shown in the FIG. 2A, access port 12 includes a sheath portion 14 defining an internal bore 16, and an external flange 18. Insert imaging probe 20 includes longitudinal body portion 22 and may include a handle portion 24. The insertable imaging probe 20 may be guided within the bore 16 of access port 12 in order to provide intra-operative imaging of internal tissues accessible within access port 12, such as anterior tissues beyond the distal end of the access port 12, and lateral tissues surrounding the lateral portions of access port 12. The body portion 22 may be provided with a rounded end (for example, with a slightly rounded end as shown in the FIG. 2A and FIG. 2B) in order to facilitate smooth entry into the bore of an access port 12.

Body portion 22 of insert imaging probe 20 houses one or more imaging elements 26, such as an array of imaging elements. As noted above, the imaging elements may employ one or more imaging modality including, but not limited to MRI, ultrasound, optical imaging (such as, but not limited to visible 2D-3D imaging, optical coherence tomography, hyper-spectral imaging, polarized light imaging, Raman Imaging, and fluorescence Imaging), electrophysiology, X-ray (computerized tomography (CT), spectral X-ray), photo-acoustic imaging, positron emission tomography (PET), thermal imaging, electromechanical arrays (strain gauges, ionic conductors), and biosensor arrays.

It will be understood that the volume of internal tissue that may be imaged when the insertable imaging device is inserted into the access port will depend on the specific imaging modality or modalities employed by the insertable imaging probe, as well as the specific configuration and orientation of the imaging elements.

The dimensions of the insertable imaging probe may be selected such that the probe may fit within a pre-selected access port. For example, the insert imaging probe may have a diameter such that upon insertion of the insertable imaging probe into the access port, the insert imaging port is received within the access port. Accordingly, the outer diameter of the body portion of the insert imaging probe may be selected to be sufficiently large that the insert imaging probe makes contact with the inner wall of the access port during its introduction therein. For example, the outer diameter of the insertable imaging probe may be selected such that the insertable imaging probe frictionally engages with the inner wall of the access port during insertion. For example, the outer diameter of the insert imaging probe may be selected to be greater than 95%, or greater than 98% or greater than 99%, of the inner diameter of the access port.

Such embodiments, which provide for a close fit between the insertable imaging probe and the access port, may be beneficial in maintaining a suitable orientation of the insertable imaging probe during its insertion within the access port, and/or for supporting the insertable imaging probe in a prescribed orientation during its insertion into the access port.

In order to facilitate insertion of the insertable imaging probe into the access port, the insertable imaging probe may include one or more air passage features that facilitate the expulsion of air from the bore of the access port during insertion of the insertable imaging probe into the access port, and to facilitate the introduction of air into the bore of the access port during withdrawal of the insertable imaging probe.

Figure 3A:
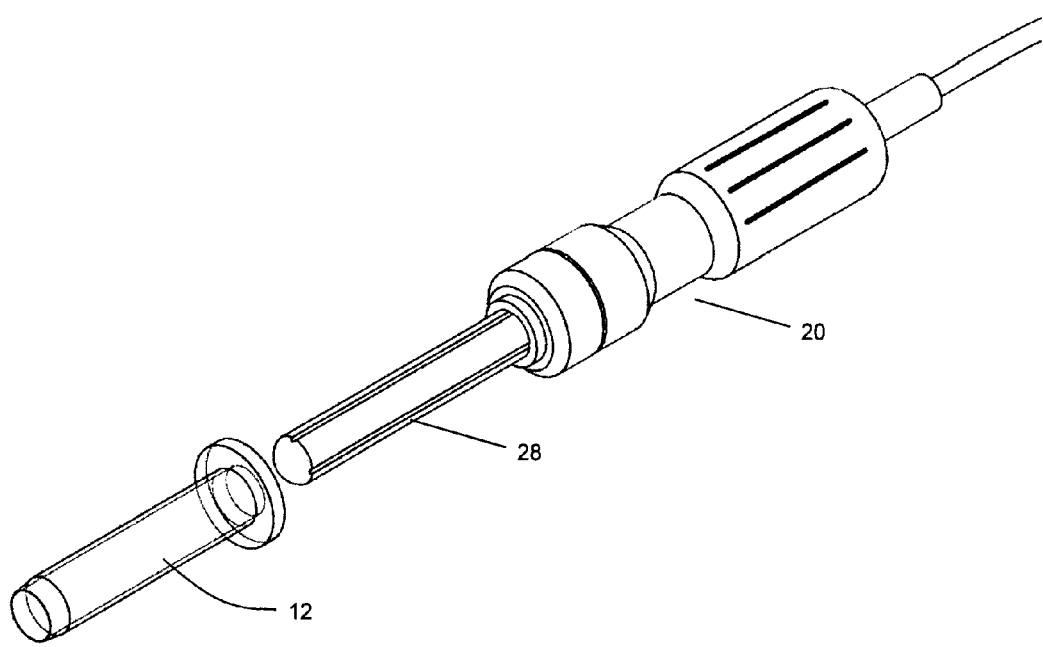
FIG. 3 illustrates an example implementation of an insertable imaging probe that includes external features that allow the passage of gas during insertion or withdrawal of the insertable imaging probe.

FIG. 3 illustrates one example implementation of an insertable imaging probe 20 that has grooves 28 (e.g. channels or recesses) formed within its outer surface that allow gasses to escape during insertion or be introduced during withdrawal, thus preventing a vacuum effect from occurring. As shown in FIG. 3, the grooves 28 may be longitudinal grooves. In other example implementations, the grooves may extend in alternative orientations, such as in a serpentine configuration or a threaded configuration, such that groove spans the longitudinal extent of the insertable imaging probe 20. In an alternative embodiment, insertable imaging probe 20 may include a longitudinal channel formed with the body of the insertable imaging probe 20, as opposed to on the surface of the insertable imaging probe 20. It will be understood that the grooves, channels, or passages need not be completely open, and may instead be filled with a gas-permeable material that can resist fluid flow while allowing the passage of a gas.

As described further below, the close fit between the insertable imaging probe and the access port reduces the amount of air between the imaging probe and the access port. This may be useful in improving image quality for selected imaging modalities. For example, the presence of air can lead to image distortion in magnetic resonance imaging due to differences in susceptibility between air, tissue, and the materials forming the access port and the insertable imaging probe. In another example, in which the insertable imaging probe employs an acoustic or optical imaging modality, the presence of an air gap may lead to losses in signal and/or signal artifacts due to multiple reflections. In such cases, the imaging probe may be coated with a material such as a liquid or gel in order to improve the matching of impedances between the insertable imaging probe and the access port.

In alternate implementations, insertable imaging probes may have different diameters suitable for several different types of access ports. For example, an insertable imaging probe may have a diameter suitable to be received within the NICO Brainpath access port, which is currently available in several lengths: 50 mm, 60 mm and 75 mm, where the inner diameter is 13.5 mm. Different lengths are used depending of depth of tumor/target. An imaging probe for use with such a port would have a diameter less than 13.5 mm. An imaging probe that needs to be moved directionally within the port would have a diameter significantly less than 13.5 mm. In one example implementation, an imaging probe that is intended to slide freely along the axis of the port could have a diameter between approximately 12 mm and 13.4 mm. In other example implementations, an insertable imaging probe may have a diameter suitable for other types of access ports, such as access ports suitable for abdominal or spinal surgical procedures.

Figure 4:
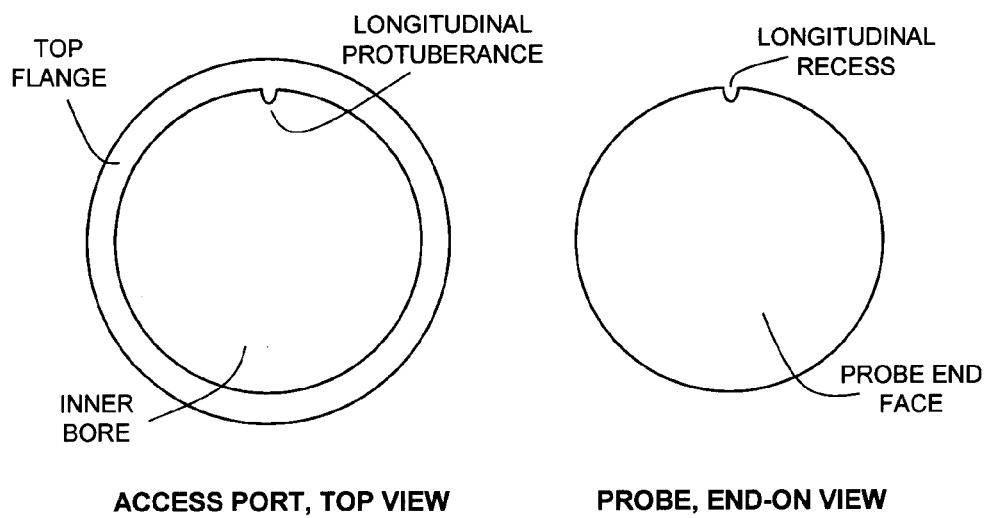
FIG. 4 illustrates an example implementation of an insertable imaging probe and an access port that have corresponding features for aligning the insertable imaging probe during its insertion into the access port.

In some embodiments, the insertable imaging probe and the access port may include corresponding features (e.g. they may be mutually keyed) that require the access port to be oriented in a prescribed angular relationship relative to the access port during the initial stages of insertion. This may be beneficial in improving and/or verifying the registration of the insertable imaging probe relative to the access port. An example implementation of such an embodiment is shown in FIG. 4. In this embodiment, one of the outer surface of the insert imaging probe 47 and the inner surface 48 of the access port may include a protrusion 45, and the other may include a recess 46 configured to receive the protrusion when the insertable imaging probe is inserted in a prescribed orientation.

1.1.1 The Probe Housing

As describe above, several embodiments of the present disclosure provide insert imaging probes that comprise a cylindrical body portion that is configured for insertion into an access port having a cylindrical bore. In some applications, a portion of the insertable imaging probe may be contacted with tissue (or could potentially be contacted with tissue) during a medical procedure. For example, in some embodiments described herein, the distal portion of the insertable imaging probe may contact tissue when the probe is inserted into an access port or conduit having a distal opening (aperture). Accordingly, in some embodiments, at least part of the body portion of the insertable imaging probe may have an external surface formed from a material that is bio-compatible. Examples of suitable biocompatible materials include polyurethane, polycarbonate, or Teflon.

Figure 5A:
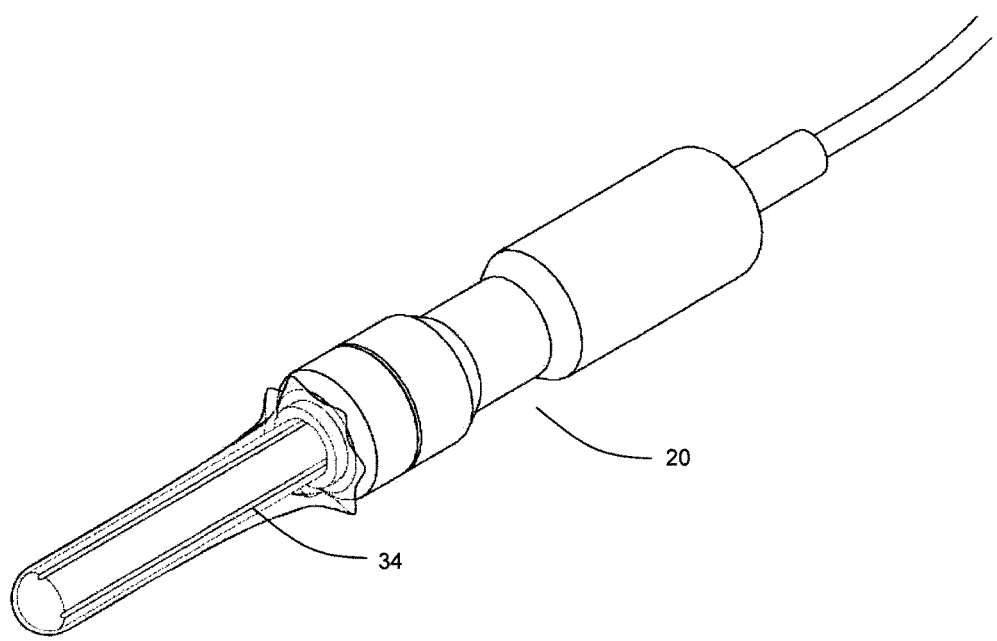
FIGS. 5A and 5B show an insertable imaging probe having a disposable outer sheath.
Figure 5B:
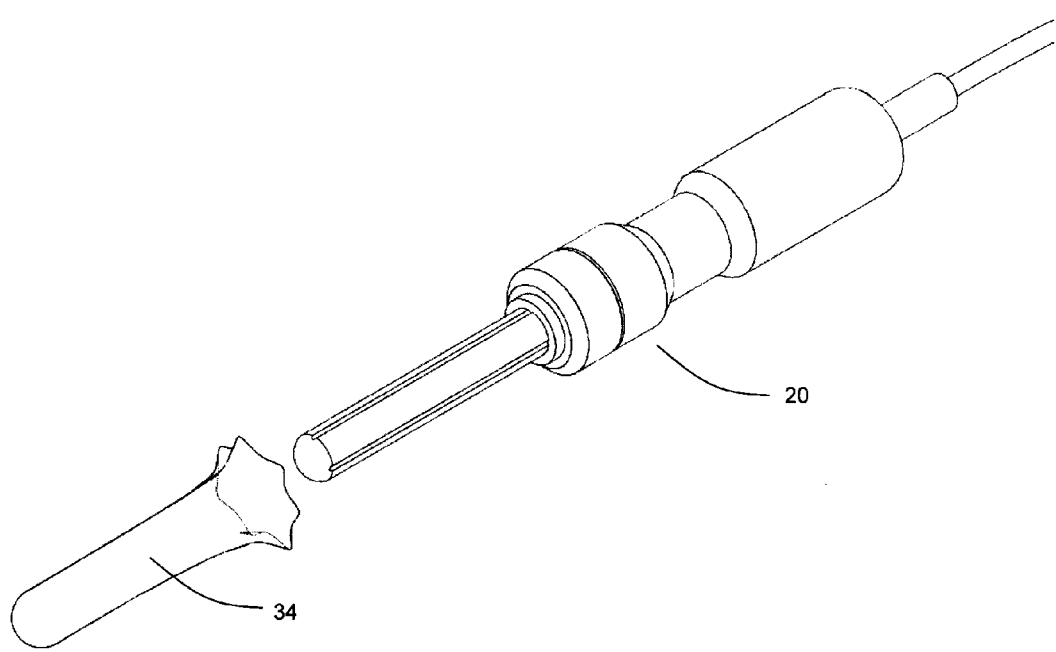

In some embodiments, at least one portion of the insertable imaging probe may be disposable and/or sterilizable. For example, the body portion of the insertable imaging probe may have an outer sheath or shell that is disposable, as shown in FIGS. 5A and 5B.

In some embodiments, the insertable imaging probe 20 may include a disposable and/or sterilizable (e.g. autoclavable) portion 34 that is connectable, via a connection mechanism such as a locking mechanism, to the handle portion. This handle, which may or may not be disposable, may also serve to store electrical components and/or to route cables back to the processing system as a whole. Incorporating some or all of the circuit elements within the handle of the probe enables the slim silhouette of the port coil.

Figure 6A:
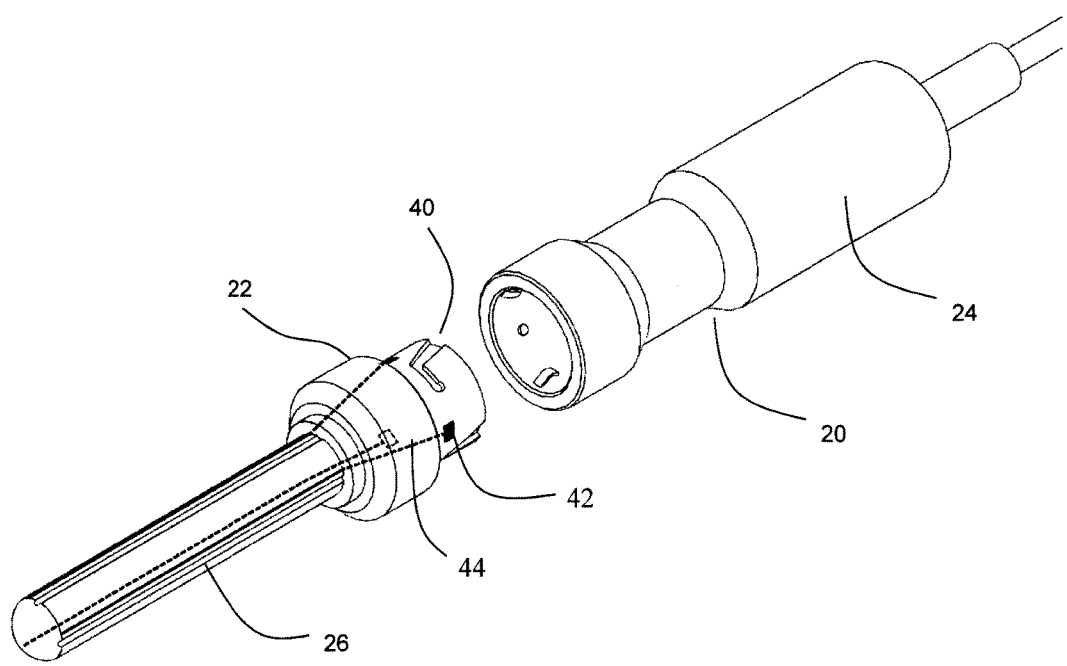
FIGS. 6A-6B illustrate an example insertable imaging probe in which a disposable body portion is connected to a handle portion by a connection mechanism.
Figure 6B:
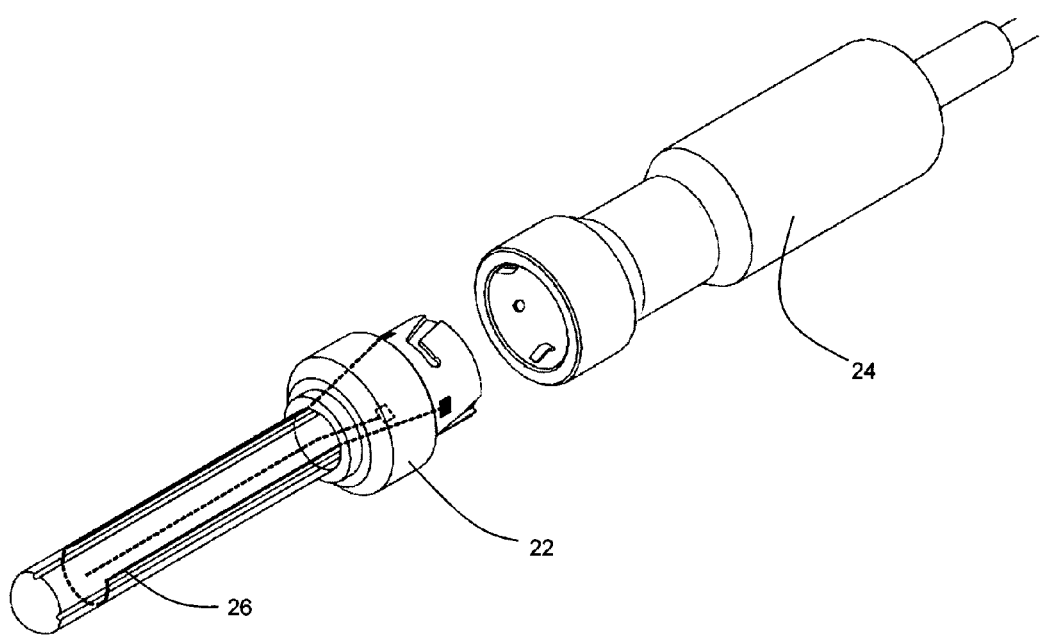

For example, FIGS. 6A and 6B illustrate an example embodiment in which insertable imaging probe 20 includes a body portion 22 that is attachable or connectable to a handle portion 24 via a connection mechanism 40. The electrical and imaging components 26 contained within the insertable imaging probe 20 may be divided into two groups: components that are housed within the handle, and components that are housed within the insertable and optionally disposable body portion of the insertable imaging probe. In some embodiments, at least some of the electrical components of the insertable imaging probe are housed within the handle 24, while other components, such as other electrical components and imaging elements or imaging assemblies, are housed within the disposable body portion.

For example, in the case of a magnetic resonance imaging probe, at least some of the electrical components, such as at least some components of the tuning and matching circuit, or preamplifier circuit, may be housed within the handle portion 24, while other components, such as one or more electrical coils, may be housed within the body portion 22 of the insertable imaging probe 20. The handle portion 24 may be mechanically and electrically connected to the body portion when the body portion is attached to (e.g. locked to) the handle 24. The mechanism 40 may be provided at the interface of the two components to ensure unique and unambiguous mating of the two parts. In one non-limiting example implementation, this connection mechanism may be provided by circular mating connectors with uniquely arranged grooves and corresponding pins or keys 42 which ensure correct polarization of the contacts 44.

In some example embodiments, a handle may be provided that is removably connectable to different body portions, where each body portion has a different coil orientation. For example, one body portion may include an endonasal coil with two orthogonal striplines, while another body potion may include a port coil using an orthogonal loop and a stripline. As long as the coil elements are tuned outside of the handle, the preamplifier could be located in the handle.

1.1.2 Markings on Insertable Imaging Probe

In some embodiments, the insertable imaging probe may have delineated markings to assist in the positioning of the insertable imaging probe within the access port. For example, the body portion of the insert imaging probe may have graduated measurement markings to provide depth information when guiding the port into the access probe.

In other example implementations, the insertable imaging probe may include one or more directional markings identifying an orientation of the probe relative to a preferred orientation. For example, in embodiments in which the insertable imaging device includes one or more magnetic resonance imaging coils, the body or handle of the imaging probe may include a directional marker identifying a preferred orientation of the insertable imaging probe relative to the $B_0$ magnetic field. Alternatively, in the example case of an insertable imaging probe that is configured for performing polarization sensitive imaging, the insertable imaging probe may have one or more directional markers identifying one or more polarization axes.

1.1.3 Single Element Insertable Imaging Probes

In some embodiments, an insertable imaging probe (or an imaging introducer) may including a single imaging element, such as a single MR coil or a single ultrasound transducer. In such cases, 2D and/or 3D imaging may be realized by mechanically (robotically) rotating the insertable imaging probe during insertion or removal of the insert component, and subsequently reconstructing the volume image through the use of software reconstruction methodologies based on a tracked orientation and position of the insertable imaging probe. In some embodiments, two or more imaging elements may be employed, where each element is associated with a different imaging modality. Such embodiments are described in more detail below.

1.1.4 Insertable Imaging Probes with Multi-Element Imaging Arrays

In other embodiments, an insertable imaging probe (or an imaging introducer) may including a plurality of imaging elements (e.g. an array of imaging elements), such as an array of MR coils, and an array of ultrasound transducers. Such embodiments are described in more detail below.

1.2 Imaging Introducer for Access Port

Figure 7A:
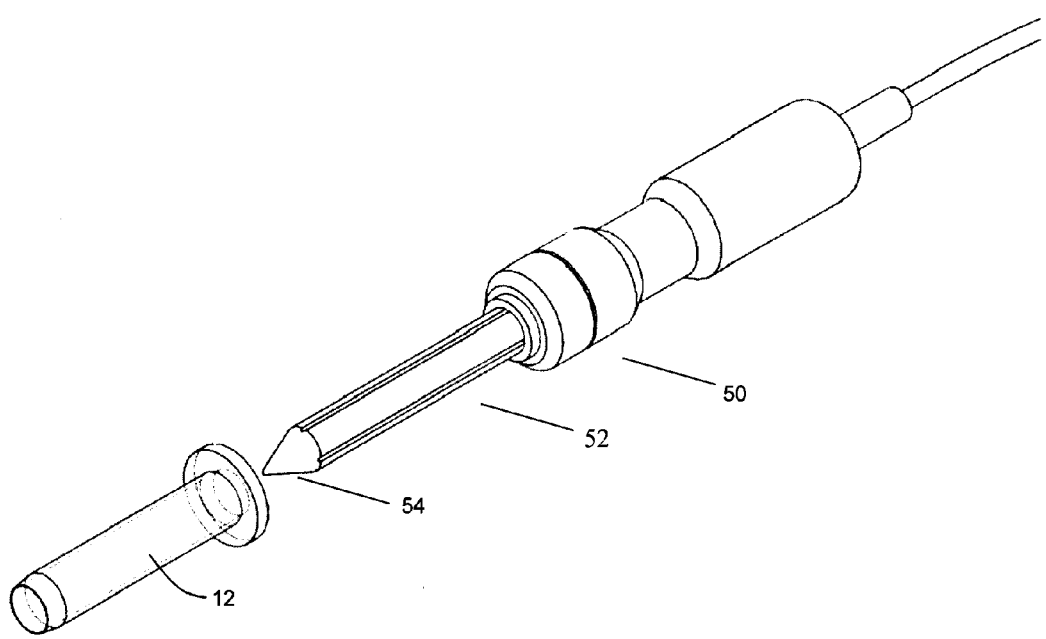
FIGS. 7A and 7B illustrate an example implementation of an insertable imaging probe that has an atraumatic distal tip, such that the insertable imaging probe may function as an imaging introducer or imaging obturator capable of performing imaging during inserting of the access port.
Figure 7B:
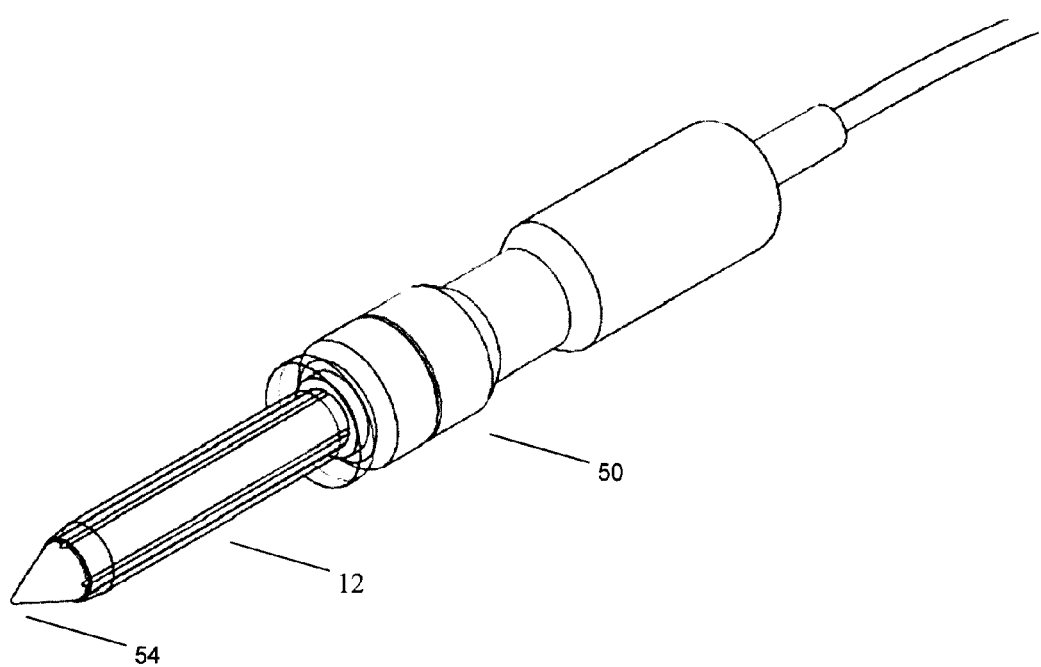

In some embodiments, the insertable imaging probe may have an atraumatic distal tip, such that the insertable imaging probe may function as an introducer or obturator for inserting the access port into the subject or patient in order enable the collection of images during the introduction of the access port, while reducing trauma and collateral damage to internal tissue. One example embodiment is illustrated in FIGS. 7A and 7B. FIG. 7A shows imaging probe 50 having body portion 52 and atraumatic tip 54. As noted above, imaging probe 50 may also have one or more channels formed in its external surface (or within its body) in order to provide a path for the passage of gases during insertion or withdrawal. FIG. 7B shows imaging probe 50 received within access port 12, where atraumatic tip 54 extends through a distal aperture within access port 12. The angle of the atraumatic tip 54 may be chosen to render the tip atraumatic for a given tissue type, or set of tissue types. For example, in the case of intracranial neurological procedures, suitable angles include 15 to 30 degrees.

1.3 Access Port with Integrated Imaging Elements

In the preceding embodiments, insertable imaging devices were described as insertable imaging probes that may be configured for use with an access port. However, in other embodiments, the access port itself may have imaging elements formed therein or thereon. For example, the access port may have integrated imaging elements, such as, but not limited to, magnetic resonance MR imaging, ultrasound, optical imaging devices (such as, but not limited to visible 2D-3D imaging), optical devices and/or conduits for performing optical coherence tomography, hyper-spectral imaging, polarized light imaging, Raman Imaging, and fluorescence Imaging), electrophysiology, photo-acoustic imaging, thermal imaging, electromechanical arrays (strain gauges, ionic conductors), and biosensor arrays.

An external connection to the proximal end of the access port could be made with connectors such as pins and sockets, with push-on connectors (such as MCX, or SMB), or threaded coaxial connectors such as SMA, or any other multi-pin connector. If the connector is to be used in a magnetic resonance imaging system, it connector should be non-magnetic.

1.4 Insertable Sleeves with Integrated Imaging Elements

Figure 9:
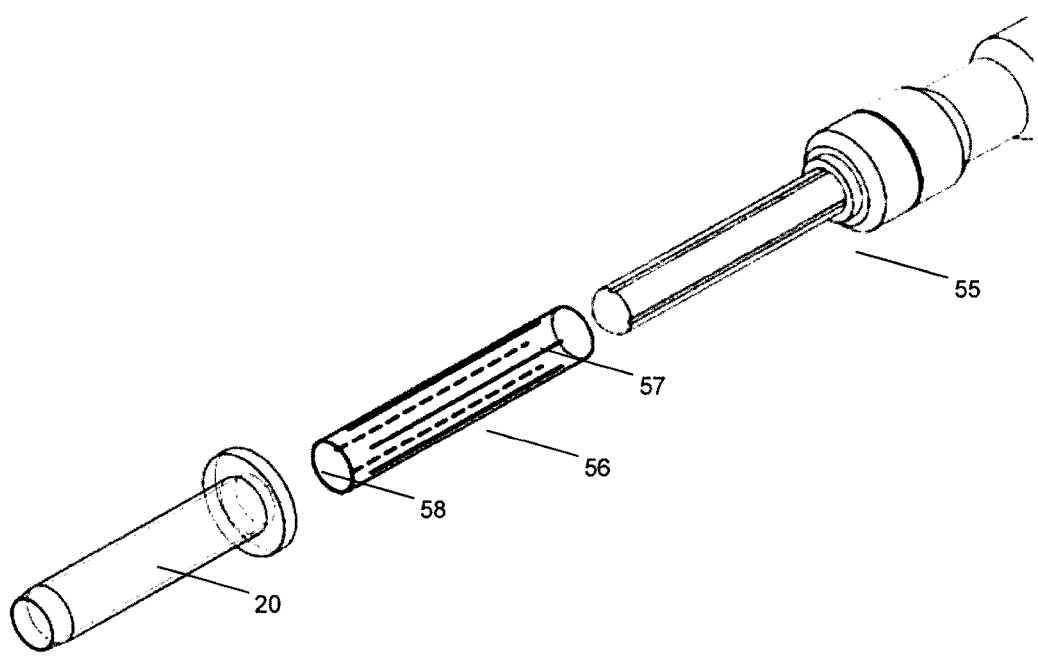
FIG. 9 illustrates an example implementation of an imaging sleeve that includes a single or multiple imaging elements.

In some embodiments, an insertable imaging device may be provided in the form of an imaging sleeve that is insertable into an access port. For example, FIG. 9 illustrates an example embodiment of an insertable imaging device 55 having an imaging sleeve 56 comprising a central bore 58 and imaging element 57 provided thereon. In alternate embodiments, imaging element 57 may also be provided thereon. In FIG. 9, imaging sleeve 56 includes a single imaging element 57, where imaging element 57 is positioned for lateral imaging, and where imaging element 57 generally collects image data through the side wall of access port 20. The imaging element 57 is energized by control circuit placed in imaging probe 50 (shown in FIG. 7B) through contact points 59. The contact points ensure good connectivity using a press-fit mechanism or other similar design features between the imaging sleeve 56 and the probe end 55. For example, the imaging sleeve shown in FIG. 9 could be employed for performing a surface or volumetric image by rotating the sleeve while inserting or removing the sleeve, and collecting image data correlated with the position and orientation of the imaging sleeve.

In an alternative embodiment, in which an imaging element is incorporated into the sleeve near or at a distal region of the imaging sleeve, such that it is oriented for imaging a tissue region beyond the distal end of the imaging sleeve (e.g. by imaging in a longitudinal direction). In such an embodiment, the imaging element may obtain images through the bottom of the access port, or directly from the internal tissue, depending on the configuration of the distal end of the access port (e.g. depending on whether or not an aperture is present in the access port, or depending on the width of an aperture in the access port). The region imaged by the imaging sleeve in this alternative embodiment could be increased, for example, by rotating the imaging sleeve. It will be understood that other embodiments may be provided by combining the aspects mentioned above, such that one or more image elements are provide for both longitudinally directed imaging and laterally directed (e.g. radially) imaging. Furthermore, an alternative embodiment in which an array of imaging elements are integrated into the imaging sleeve.

The imaging element or elements incorporated into the imaging sleeve may employ a wide range of imaging modalities, including, but not limited to, magnetic resonance MR imaging, ultrasound, optical imaging devices (such as, but not limited to visible 2D-3D imaging), optical devices and/or conduits for performing optical coherence tomography, hyper-spectral imaging, polarized light imaging, Raman Imaging, and fluorescence Imaging), electrophysiology, photo-acoustic imaging, thermal imaging, electromechanical arrays (strain gauges, ionic conductors), and biosensor arrays.

In some embodiments, the imaging sleeve may have an aperture or opening at its distal portion, such that the operator or clinician may insert items such as tools or other imaging devices and access internal tissues exposed through the central bore. In other embodiments, the distal end of the imaging sleeve may be closed at its distal surface by a tissue fixing surface that is transparent or at least partially transparent to imaging radiation associated with at least one imaging modality.

One potential benefit of an imaging sleeve embodiment is the ability to intraoperatively remove an imaging sleeve of a first type or modality and replace it with an imaging sleeve of a second type or modality. This benefit is not present for the aforementioned embodiments involving an access port with integrated imaging elements, in which the choice of imaging elements is fixed.

1.5 Combinations of Insertable Imaging Devices

In other embodiments, two or more insertable imaging devices may be used together, for example, in order to achieve multi-modal imaging of internal tissues. It will be understood that there are wide variety of combinations of insertable imaging devices that may be combined together to provide different imaging embodiments. The following examples are provide to illustrate some example implementations of such embodiments, and the scope of the present disclosure is not intended to be limited to these embodiments.

Some specific examples of combinations of insertable imaging devices are described and illustrated below.

1.5.1 Multiple Coaxial Imaging Sleeves

Figure 10:
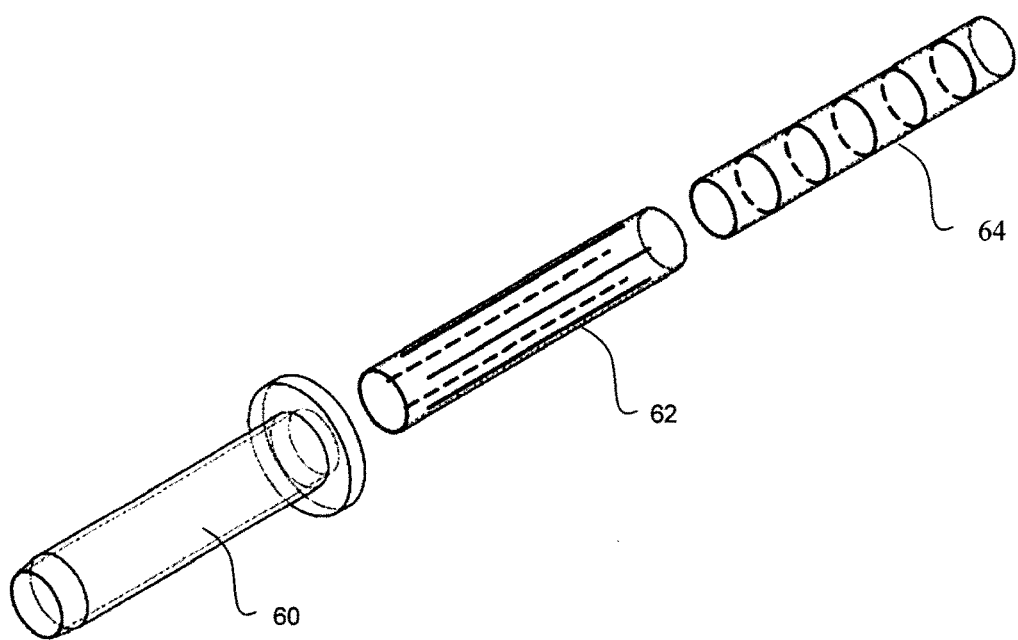
FIG. 10 shows one example embodiment of a combination of several insertable imaging devices, involving a non-imaging access port and two coaxial imaging sleeves inserted into the access port.

FIG. 10 illustrates a non-imaging access port 60, and two coaxial imaging sleeves 62 and 64 that are insertable into the access port 60 where the two imaging sleeves 62 and 64 may be nested.

1.5.2 Imaging Sleeve(s) and Insert Imaging Probe/Imaging Introducer

Figure 11:
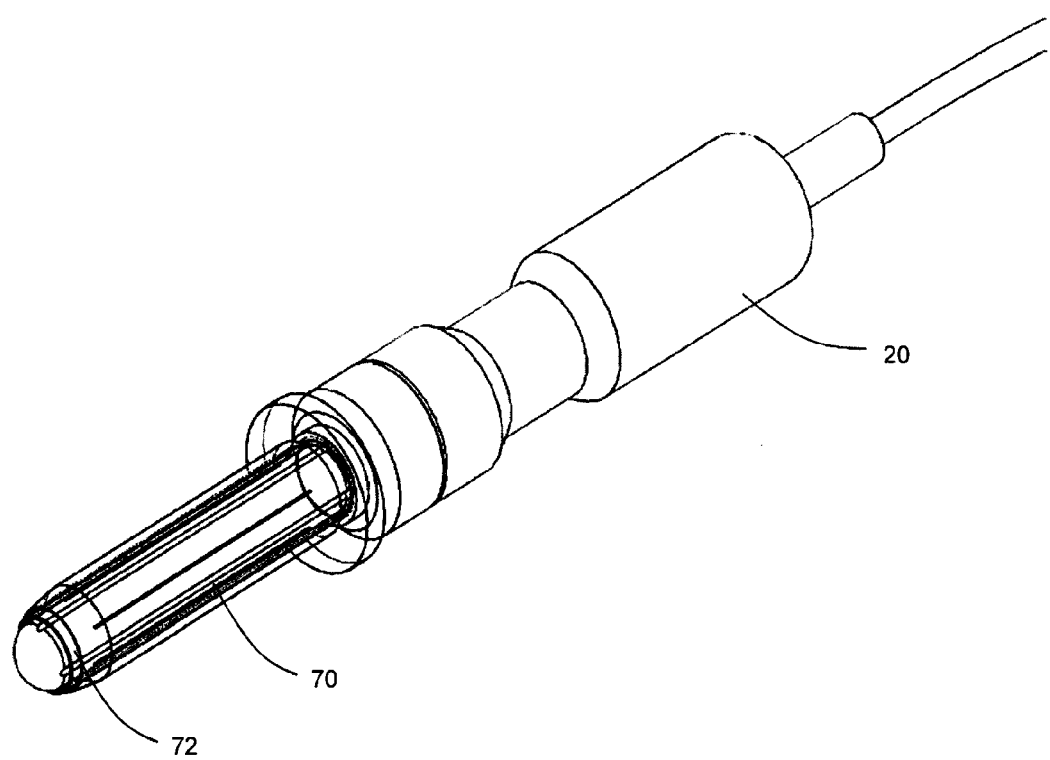
FIG. 11 shows another example embodiment of a combination of several insertable imaging devices, involving a non-imaging access port, an imaging sleeve inserted into the access port, and an insertable imaging probe.

FIG. 11 illustrates a non-imaging access port 70, one or more imaging sleeves 72 inserted into the access port (two or more imaging sleeves may be nested), and one of an insertable imaging probe 20 and an imaging introducer. Electrical connection to the conductive elements in imaging sleeves 72 may be established using press-fit mechanism 59 described in FIG. 9.

1.5.3 Imaging Access Port and Insert Imaging Probe/Imaging Introducer

In a further embodiment, an access port with integrated imaging element(s) and one of an insertable imaging probe and an imaging introducer may be envisioned.

Figure 12:
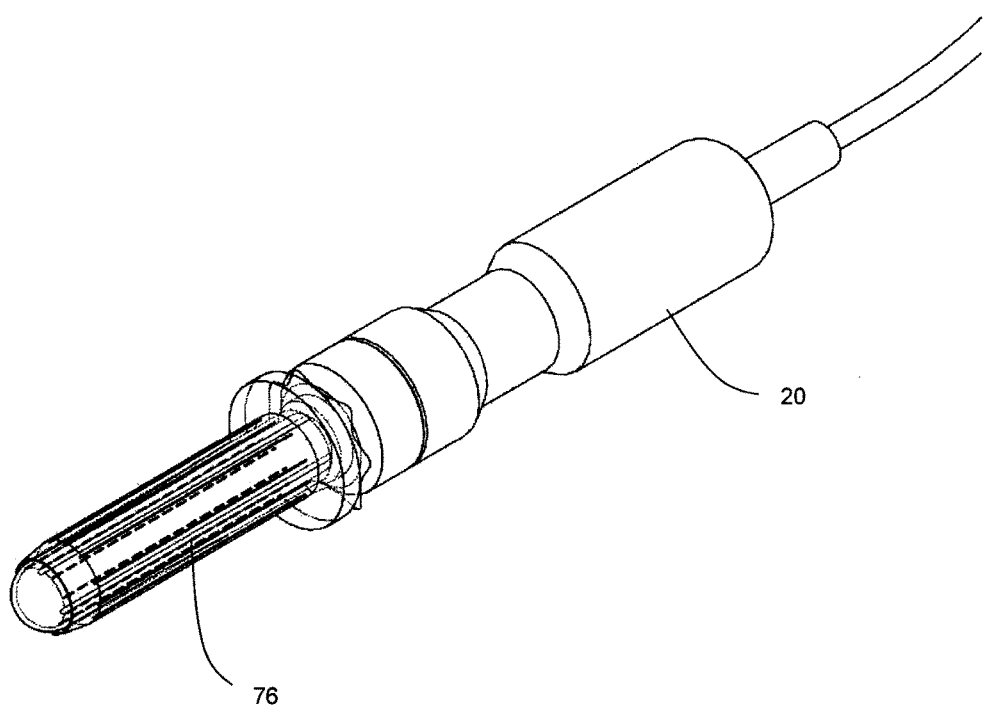
FIG. 12 shows another example embodiment of a combination of several insertable imaging devices, involving an access port with integrated imaging element(s) and an insertable imaging probe.

1.5.4 Imaging Access Port and Imaging Sleeve(s) and Insert Imaging Probe/Imaging Introducer In FIG. 12, an access port with integrated imaging element(s) 76 is shown and one or more imaging sleeve inserted into the access port (two or more imaging sleeves may be nested), with an imaging probe 20 inserted into the imaging sleeve.

Figure 13:
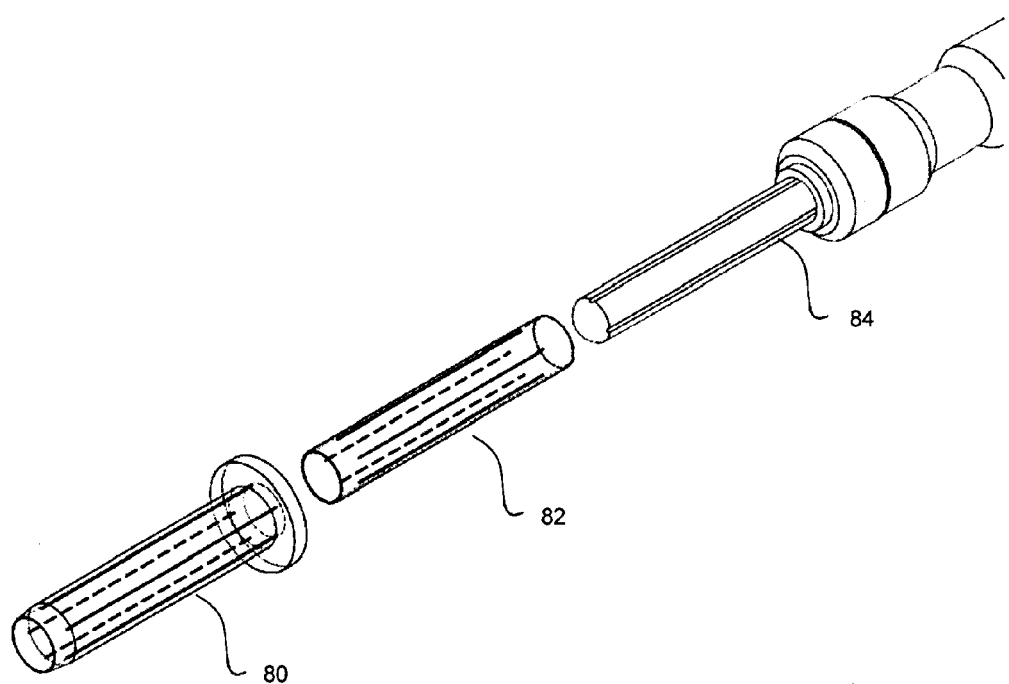
FIG. 13 shows another example embodiment of a combination of several insertable imaging devices, involving an access port with integrated imaging element(s), an imaging sleeve inserted into the access port, and an insertable imaging probe.

1.5.5 Imaging Access Port and Imaging Sleeve(s) and Insert Imaging Probe/Imaging Introducer In FIG. 13, an exploded view is shown, including an access port 80 with integrated imaging element(s) 82, an imaging sleeve 82 insertable into the access port 80 (where two or more imaging sleeves may be nested), and an insertable imaging probe 84.

While the preceding section has introduced several embodiments of the present disclosure from a general perspective, the following sections present specific and non-limiting embodiments providing example implementations involving selected imaging modalities or combinations of imaging modalities. The following section presents example various implementations involving magnetic resonance insertable imaging devices.

2. Magnetic Resonance (MR) Insert Imaging Device

The present section describes various embodiments employing one or more magnetic resonance imaging radio-frequency (RF) coils (e.g. coil elements) for imaging within an access port, cannula, lumen, channel or other such structure, in order to achieve magnetic resonance imaging within an internal area of interest.

Some embodiments introduced herein provide insertable MR imaging devices that are alternatives to current surface or volume coils, where the insertable MR imaging devices can be inserted within a cavity to provide imaging of the tissues surrounding the devices and tissues beyond a distal end of the device (end-fire imaging) given its close proximity. The coil's ability to detect signals increases as the coil approaches the tissue being imaged. RF coils that are local to the tissue of interest have a higher signal-to-noise ratio (SNR) than those positioned further away, and thereby a higher quality image.

As described above, some embodiments described in the present section may complement a minimally-invasive neurological procedure (such as surgical procedures) whereby a procedure involving internal brain tissue is conducted via a narrow corridor formed via an access port. For example, an insertable magnetic resonance imaging device may be adapted to be received (e.g. slidably received, as described in Section 1 above) into the bore of an access port and exploit its close position to produce MR images, such as high resolution MR images of the surrounding (lateral) brain tissue and/or forward-looking (anterior, distal) tissues. Such images may be used during medical procedures (e.g. surgical procedures), potentially providing detail that would otherwise not be obtainable with current technologies (or would otherwise be obtainable with less resolution or signal to noise, using currently available technologies).

Several insertable MR coil probes known in the art have been designed for vascular or prostate imaging, where the tissue of interest is located adjacent (laterally) to the insertable coil. Some embodiments of the present section of the disclosure provide insertable imaging devices that are suitable for imaging anterior tissues, or both lateral and anterior tissues. Such devices may be useful, for example, in neurosurgical and endo-nasal applications involving an inserted access port, where it is imperative to receive signals from the tissue residing at the distal portion of an access port.

2.1 Example MR System

Figure 14:
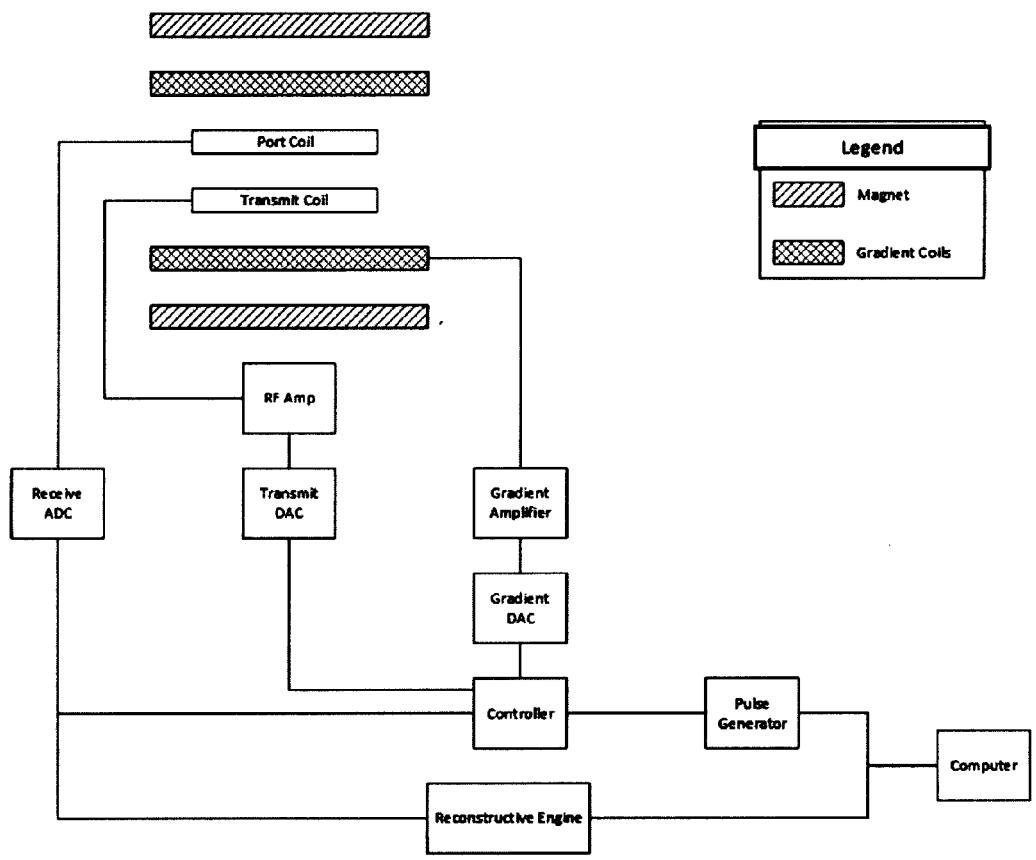
FIG. 14 schematically illustrates an example magnetic resonance imaging system that includes an insertable magnetic resonance imaging device.

FIG. 14 provides a schematic illustration of a magnetic resonance imaging system that involves an insertable MR imaging device. The main magnet of a magnetic resonance imaging scanner generates a magnetic field ($B_0$) and RF coils are used to generate orthogonal magnetic fields ($B_1$) for exciting the signals during transmission and receiving the MR relaxation signals during reception. The main magnet could be, for example, a solenoid, single-sided magnet, or a dipole array made with superconducting wire, high temperature superconducting (HTS) wire, an electromagnet, or a resistive magnet, or lastly a Halbach array of permanent magnets.

The example system includes an insertable MR imaging device, which may be, for example, an insertable MR imaging probe, an insertable MR imaging introducer for inserting an access port, an access port with one or more integrated MR imaging coils, one or more MR imaging sleeves that are configured to be coaxially inserted into an access port, or various combinations of these insertable imaging devices, as illustrated in Section 1. Various example implementations of such insertable MR imaging devices, and various coil configurations, are described in detail below.

Magnetic resonance imaging can be performed either with separate transmit and receiver coils, or by using the same coil for transmit and receive. The transmit coil may be a head coil, body coil, or the probe itself. The reason one tends to use a separate transmit coil is to have uniform excitation of tissue. However, by using appropriate pulse sequences, it is possible to still obtain reasonable images from a non-uniform T/R coils.

Other elements included in the example MR system, shown the Figure include a gradient system consisting of coils, amplifiers, and DAC converters, an RF system which comprises a transmitting and receiving coil which may or may not be the same device, in addition to DAC/ADC, and amplifiers. Finally, a computer, controller, pulse generator and reconstruction engine are included.

The controller sends the pulse sequence at the correct time, and the reconstruction engine generates the image from the raw data. The controller and the reconstruction engine, while shown as separate components in FIG. 14, may alternatively be integrated in a single device.

2.2 Example Electrical Circuit

Figure 15:
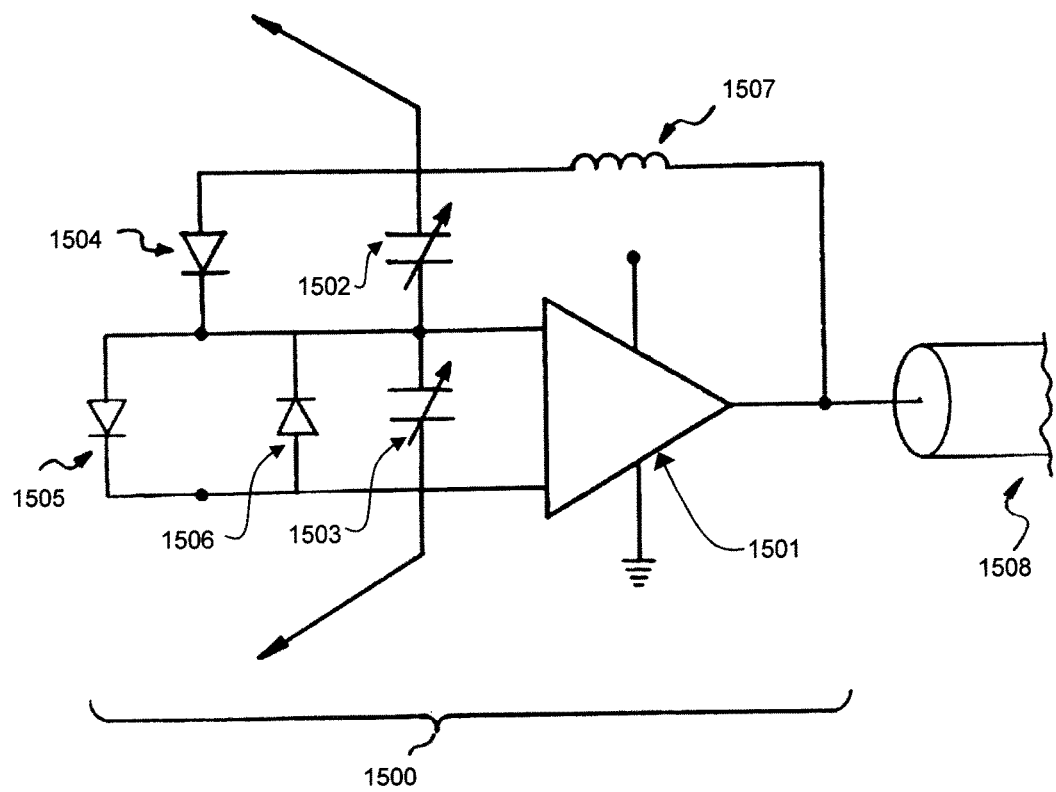
FIG. 15 schematically illustrates an example implementation of circuit for receiving signals from a magnetic resonance coil element within an insertable MR imaging device.

FIG. 15 schematically illustrates an example implementation of circuit for receiving signals from a magnetic resonance coil element within an insertable MR imaging device. The electrical circuit 1500 includes a preamplifier 1501 (or low noise amplifier (LNA) that amplifies the signal that is generated. Variable capacitors (1502 and 1503) are used to tune and match the circuit 1500. Diodes (1504, 1505, 1506) are used to detune the coil (if it is a receive only coil) when the system is transmitting. One or more inductor(s) (or RF chokes) 1507 are used to separate DC control signals from the RF path.

An example of a circuit 1500 for receiving signals to a magnetic resonance coil is shown in FIG. 15. In the example embodiment shown, a coil element (e.g. a single coil or a coil element of an array of coil elements) is connected and matched to a low-noise preamplifier, which will amplify the received signal for processing. These channels may be connected using a 50Ω coaxial cable (15.8) that carries the ac signal to and from the preamplifier. The preamplifier, itself, may be powered through a set of discrete wires. In this diagram, the coil is connected to the two arrows. A coax connection could be made here with the outside of the connector at the bottom and the center line at the top, alternatively a pair of wires could be used, or a twinax line, or a twisted pair, or a direct connection to the coil.

The circuit may contain an active and passive detuning diode to ensure the coil is non-resonant at the Larmor frequency during the transmission phase of the MRI. The passive diode is activated by the transmitting field while the active diode is powered through the centerline of the aforementioned coaxial cable.

The coil must be tuned to the resonant frequency of the system. A variable capacitor is typically used for this purpose because it is easily adjusted. However, a fixed capacitor could alternatively be used. Secondly, to achieve the lowest noise figure, the preamplifier has an ideal source impedance. Another variable capacitor is used to vary the source impedance so that this impedance is achieved. Again, a fixed-value capacitor could be used for this purpose. The inductor is used to as an RF choke to separate the control signals (such as a command to block during transmit) from the RF path.

It is noted that not all of the components would need to reside within the probe body—some could reside within the handle.

It is noted that the circuit shown in FIG. 15 is but one example circuit. There are alternate methods to noise match the preamplifier (such as using inductors, multiple capacitors, multiple inductors, transformers, transmission lines, etc), alternate methods to detune the coil (such as PIN diodes, switches, FETs, MEMS devices), alternate methods to shield the control signals from the RF line (such as PIN diodes, switches, transmission lines).

Although FIG. 15 illustrates a single circuit that is connectable to a single coil, it will be understood that in embodiments in which the MR imaging device includes an array of coil elements (i.e. multiple channels), the circuit shown in FIG. 15 (or an alternative circuit) may be included for each coil element in the array.

2.3 Insertable MR Imaging Probes

In some embodiments, the insertable MR imaging device is an insertable imaging probe, as described in Section 1.1 above, where the imaging elements are one or more MR coils.

2.3.1 The Probe Housing

In embodiments in which the MR imaging probe is configured to be used within a MRI scanner, employing the scanner to provide the primary $B_0$ field, the probe housing constructed from an MRI-compatible material. Examples of MRI-compatible materials include polycarbonate, Teflon, Delrin and PEEK.

The dimensions of the insertable imaging probe may be selected such that the probe may fit within a pre-selected access port, as described in Section 1.1. However, it is to be understood that the MR imaging probe intended to be limited to applications involving the use of an access port, and may additionally or alternatively be used outside of an access port in any in-situ or ex-situ applications where appropriate. For example, MR imaging probe embodiments according to the present disclosure may be employed for local imaging during an open craniotomy, endonasally, or when examining sample tissue. In some non-limiting example embodiments, the diameter of the MR imaging probe can range from a diameter from less than approximately 1 mm to 13 mm, and with a length of less than approximately 1 mm to 100 mm.

In some embodiments, at least one portion of the MR imaging probe may be disposable and/or sterilizable, as described in Section 1.1. For example, the disposable and/or sterilizable (e.g. autoclavable) portion of the insertable MR imaging probe may be connectable, via a locking mechanism, to a handle that is used to position the MR imaging probe as required. This handle, which may or may not be disposable, may also serve to store electrical components and/or to route cables back to the MRI system as a whole. Incorporating some or all of the magnetic resonance circuit elements within the handle of the probe enables a slim silhouette of the body portion of the MR imaging probe.

As described in Section 1.1.1, in some embodiments, the electrical and imaging components contained within the MR imaging probe may be divided into two groups: components that are housed within the handle, and components that are housed within the insertable and optionally disposable body portion of the insertable imaging probe. In some embodiments, at least some of the electrical components of the MR insertable imaging probe are housed within the handle, while other components, such as other electrical components and imaging elements or imaging assemblies, are housed within the disposable body portion. For example, at least some of the electrical components, such as at least some components of the tuning and matching circuit, or preamplifier circuit, may be housed within the handle portion, while other components, such as one or more electrical coils, may be housed within the body portion of the insertable imaging probe.

Some example configurations for the integration of electrical components into the handle of a MR imaging probe are as follows. In one example, only the wire portion of the coil resides in the probe body, while the remainder of the components reside in the handle. In another example, the coil wire and tuning capacitors reside within the probe body, while the matching components and preamplifier(s) reside in the handle. In another example, the coil wire, tuning capacitors, and matching circuits reside within the probe body, while the preamplifier(s) reside within the handle. Finally, in another example, all components may be housed within the probe body. In embodiments in which one or more components are integrated into the handle, for use with a disposable or interchangable probe body portion having one or more integrated coils, the tolerances on the capacitors housed within the handle portion could be specified to be sufficiently low or tight.

Some MR imaging probe designs according to embodiments provided herein serve to excite or receive a $B_1$ field substantially perpendicular with the main $B_0$ field, as generated by the main magnet, to acquire a high or maximum signal potential. It is possible that the alignment of the port coil with the main magnetic field changes with operating conditions, for example, the angle of the operating corridor. For this reason, the MR imaging probe may be made available in varying coil geometries to accommodate operating conditions and magnetic field orientations. The various coil configurations described below provide several non-limiting example implementations of such different coil geometries.

In some embodiments, the handle portion of the MR imaging probe may be reusable, and may be configured to mate with a variety or disposable and/or sterilizable body portions having different coil types of geometries.

2.3.2 Markings on Coil Housing and/or Handle

As noted in Section 1.1.2, the body and/or handle portion of the insert imaging probe may have delineated markings, for example, with graduated measurement markings to provide depth information (perception) when guiding the port into the cavity.

Figure 37:
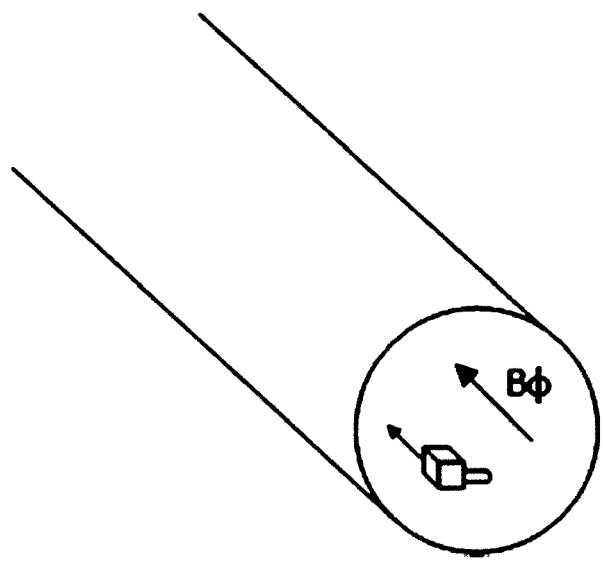
FIG. 37 illustrates an embodiment of a probe showing the correct positioning relative to the $B_0$ field.

In addition, a '$B_0$' marking may be provided, which can be employed to ensure the probe is positioned with proper electromagnetic field alignment. Aligning the $B_0$ marking on the MR imaging probe with the known direction of the $B_0$ field of the scanner (e.g. axially within the bore of the scanner) will ensure that coil elements within the MR imaging probe will be receiving and/or transmitting fields orthogonal to the $B_0$ field of the scanner as shown in FIG. 37.

2.4 Coil Configurations and Geometries

The coil designs presented below are provided as example and non-limiting implementations of potential coil configurations. Some of the following embodiments provide coils that are configured to produce a forward-looking focused receiving or transmitting zone. In other words, some of the following embodiments provide coil configurations that are sensitive to regions anterior to the longitudinal probe body (regions beyond the distal end of the probe body), e.g. in an end-fired configuration beyond the distal region of the body of the imaging probe. Such embodiments may be included or incorporated within the various MR imaging probes described within this disclosure.

The coils themselves may be formed from a conductive material, for example copper, silver, silver coated copper wire, super conducting wire or tape, high temperature superconducting wire or tape, carbon nanotubes, or graphene, that may or may not be cooled (to lower metal resistivity and hence increase SNR) during image acquisition. Where needed, a dielectric substrate may be used. Suitable dielectric materials may be materials such as polyurethane, polycarbonate, Teflon, air, foam, FR4, liquid crystal polymer (LCP), low temperature cofired ceramics (LTCC), or high temperature cofired ceramics (HTCC), among others.

It will be understood that the MR coil may be provided according to a number of different configurations and fabrication methods. For example, the coil may be formed from wire and wound. Alternatively, the coil could be thick film conductor, and screen printed. In othere examples, the coil could be tape and adhered to a surface. In other examples, the coil metal may be sputtered or machined away from a block of metal, etched, or formed using EDM.

2.4.1 Folded Stripline

The first example embodiment is based on the stripline resonator, and is illustrated in FIGS. 16 A-C. This stripline generates a $B_1$ field (or, as a receive-only coil, is sensitive to magnetic fields) in the x direction.

The stripline, having a folded configuration, focuses the imaging region in an end-fire direction (e.g. in a region beyond the distal extent of the coil, as shown in the Figure.

Figure 16A:
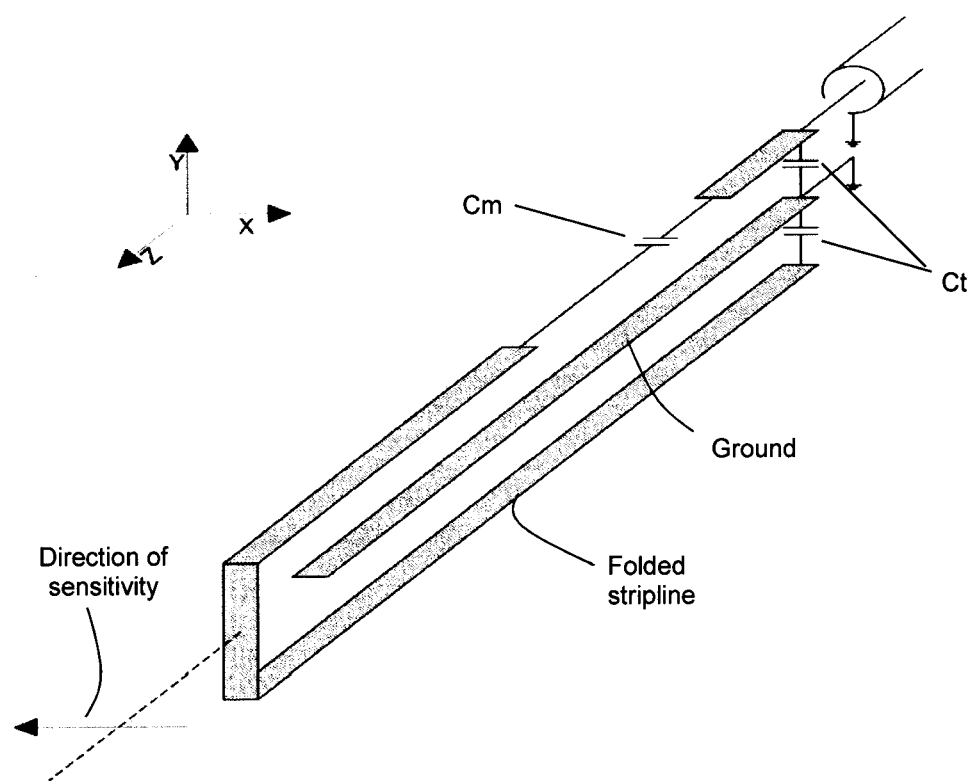
FIGS. 16A-C illustrate an example coil configuration employing a folded stripline resonator.

As seen in FIG. 16A, this stripline coil is electrically shortened with capacitors ($C_t$) to a half-wavelength in dimension where the wavelength is akin to the aforementioned Larmor frequency. A matching capacitor ($C_m$) is used to match the stripline to the amplifier. This structure is advantageous given its low-profile design, and high adjacent SNR capability.

The stripline may be constructed from conducting material that is folded about a dielectric substrate containing a ground-plane, also made from conducting materials.

The signal line and the ground line should be separated by some material, such as a dielectric, or other insulator. The dielectric can also be used to insulate the outer conductors from the patient. In this figure, the dielectric is between the conductors, as well as on the outside of the outer conductors. The figure shows a side view of the stripline inside a cylinder. It is configurable within a cylinder. The electrodes are close to the surface of the probe body.

Figure 16B:
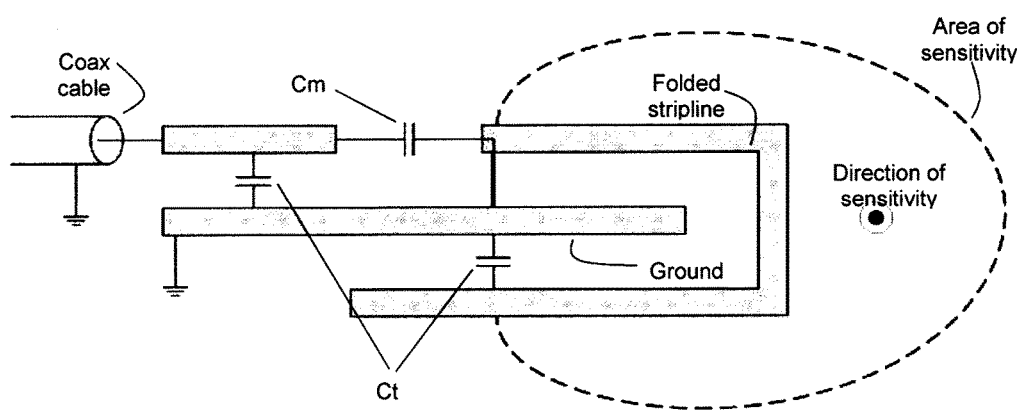
Figure 16C:
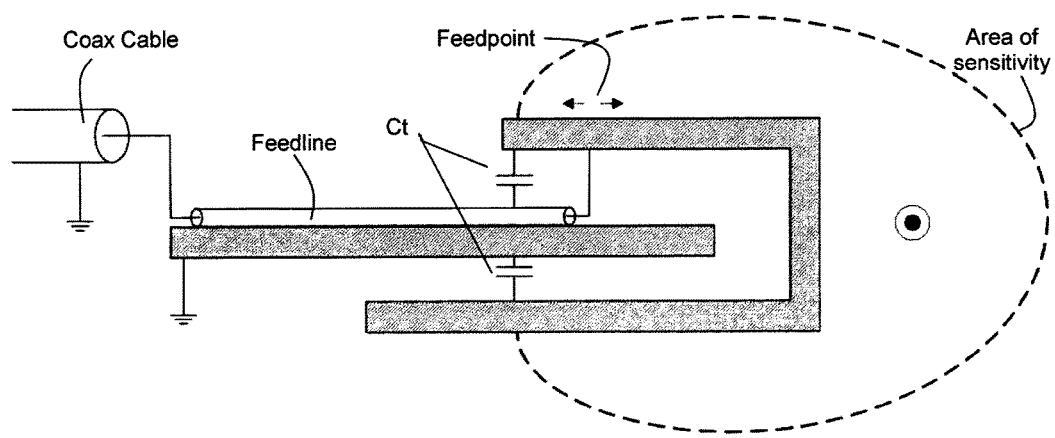

To feed the stripline, two example approaches are considered: the first embodiment employs a series capacitor to match the feedline to 50Ω (or any desired impedance), as shown in FIGS. 16B and 16C. The second embodiment varies the location of the feed point to achieve a 50Ω match (or any desired impedance) and does not use a matching capacitor ($C_m$). In this embodiment, the outer conductor of a coax line may be (though is not required to be) electrically connected to the ground conductor of the coil to avoid floating conductors when connecting the feedline.

It will be understood that any or all the electrical components (e.g. capacitors, diodes, amplifiers, RF inductors) from the conducting strips used for the stripline may be contained within the handle portion of the insertable MR imaging probe. This configuration allows for a low-cost disposable embodiment to be provided, where the electrical components are located in a re-usable "handle" portion and connected to a disposable (or sterilizable) body portion. Two example implementations of this embodiment are shown in FIGS. 17A and 17B.

Figure 17A:
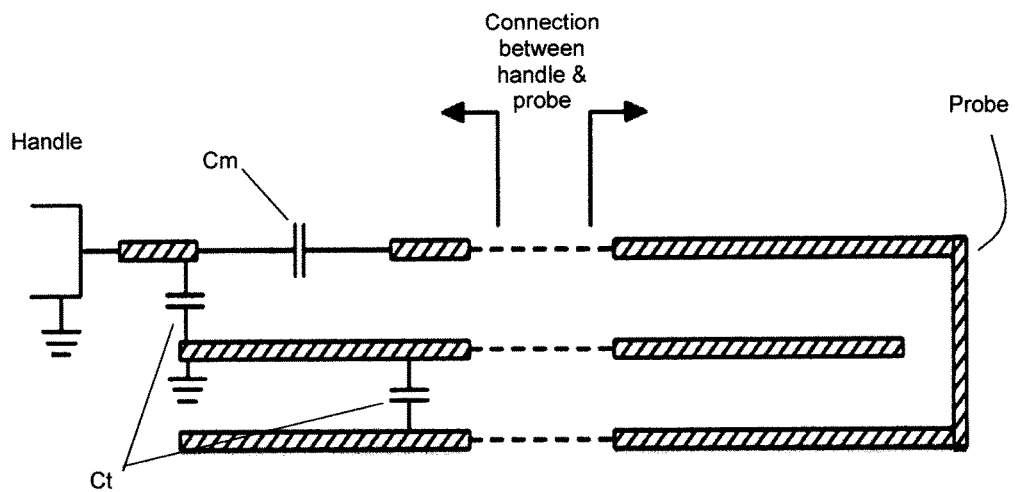
FIGS. 17A-B illustrate an example coil configuration employing a folded stripline resonator in which the electronics are provided within the handle portion, while the coil element is provided in a disposable or sterilizable body portion.
Figure 17B:
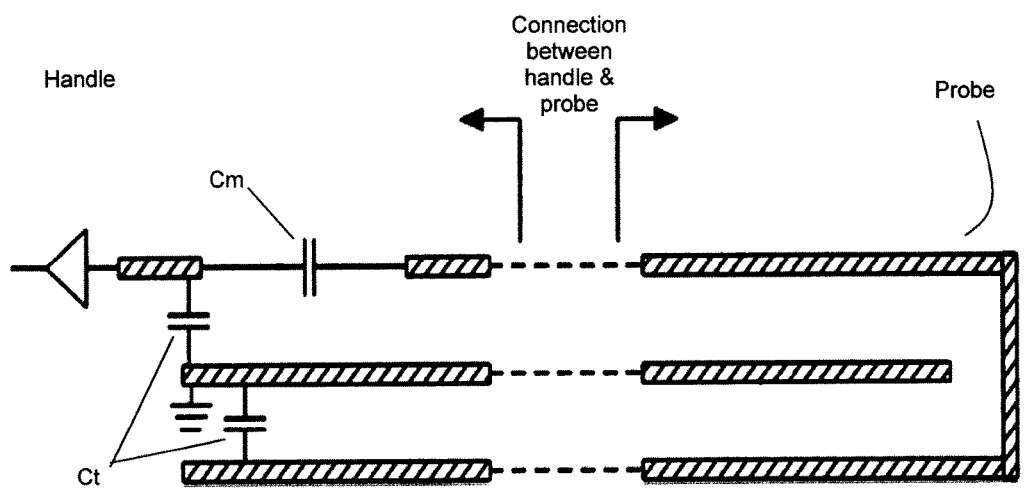

In FIG. 17A, the handle is on the left, the removable portion is on the right. The connections can be made with coax connectors such as SMA, N, F, microcoax, SMB, pin and socket, press contact, springs. The preamp could be located in the handle (as in FIG. 17B), or even further removed from the imaging coil and not in the handle. However, putting the preamp closer to the antenna can improve performance by increasing SNR.

In some example implementations, the width of the stripline can vary from less than approximately 1 mm to greater than 13 mm, while the length of the folded stripline can measure from less than 1 mm to greater than 100 mm. The value of the tuning capacitors $C_t$ will change as the length is varied, because the length of the antenna corresponds to inductance, and the capacitors are required to resonate with the inductance. One skilled in the art will know to vary the capacitor value as the length is varied.

It will be understood that there are many possible configurations of the stripline resonator based coil. The following sections illustrate some additional example implementations that involve coils based on multiple striplines.

2.4.2 Folded Quadrature Striplines

Figure 18:
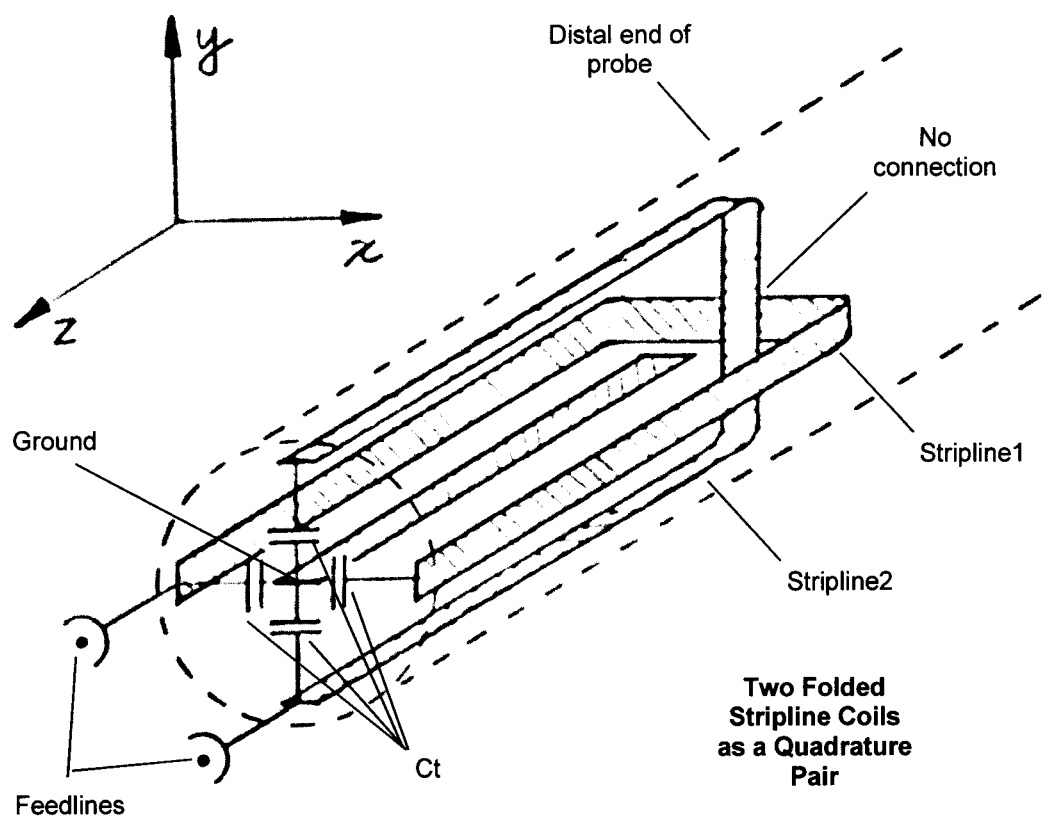
FIG. 18 illustrates an example coil configuration employing a two folded stripline resonators arranged in a quadrature configuration.

A quadrature coil is sensitive to two orthogonal polarizations of magnetic field. FIG. 18 presents an example of two folded stripline coils as a quadrature pair. One of the striplines generates (or is sensitive to) a $B_1$ field in the x direction and the other in the y. The four capacitors shown in the figure are tuning capacitors. The center line is connected to ground. While the striplines both fold over each other at the distal end of the probe, there is no electrical connection made between the striplines at this point. The only electrical connection between the striplines is the common ground that they share.

To connect to tuning and matching circuitry, a ground connection would be attached to the center line. A matching circuit would be attached each of the circle-dot connections. The matching circuit could be a matching capacitor, or inductor, or phase shifting network, followed by a preamplifier. The end of the probe is at the other end of the capacitors.

It is to be understood that the number of striplines used herein may vary. These striplines are depicted as sharing a common ground plane within the center of the coil, however, in other embodiments, the striplines may have separate ground planes.

2.4.3 Distal Stripline Arrays

Figure 19A:
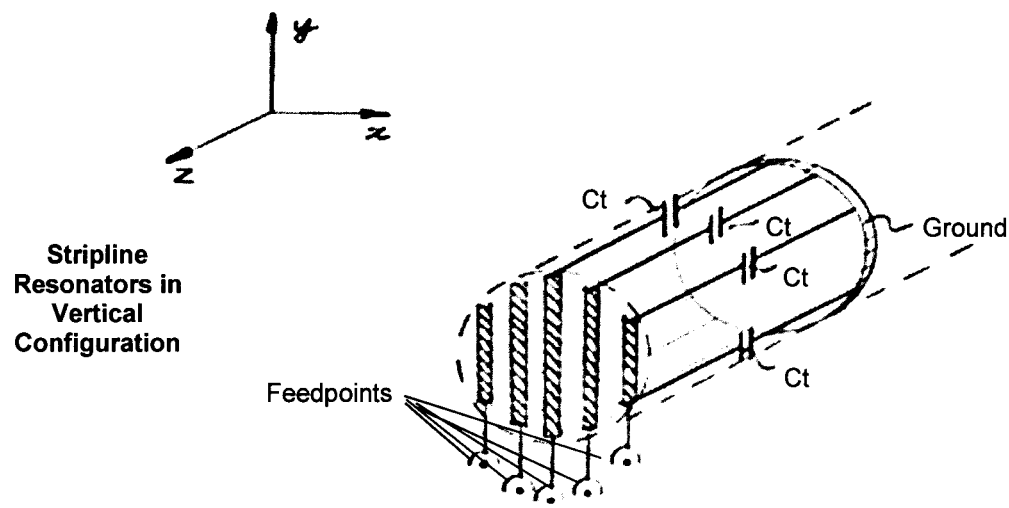
FIGS. 19A-C illustrate example embodiments where stripline resonators are provided at or near the distal portion of the MR imaging probe, either in a linear (A, B) or (C) radial configuration.
Figure 19B:
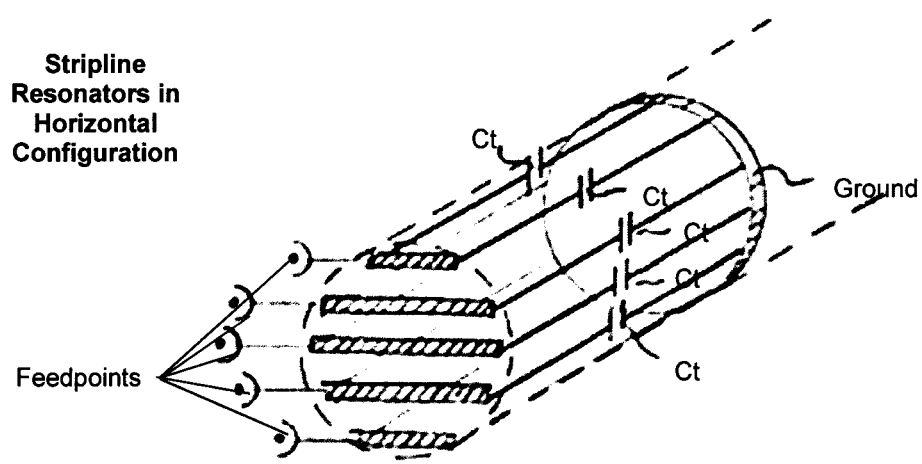
Figure 19C:
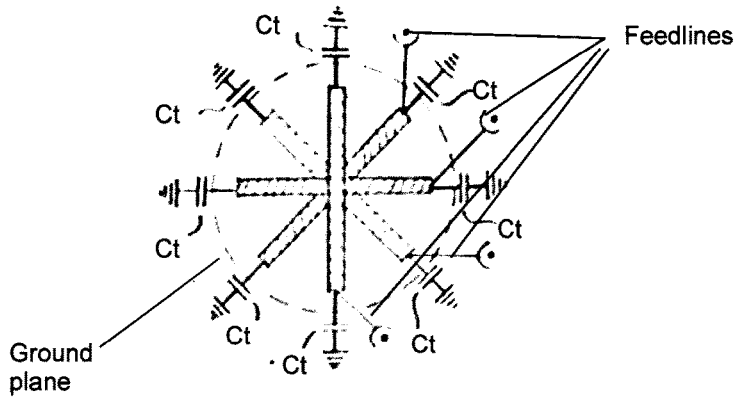

FIGS. 19A-C illustrate additional embodiments where stripline resonators are provided at or near the distal portion of the MR imaging probe, either in a linear or radial formation. In each of these embodiments, the receiving or transmitting region associated with the coil array lies beyond the distal region of the MR imaging probe.

The common ground is a solid, circular ground plane underneath each stripline. The depth is somewhat exaggerated in this figure. The outputs would be combined as a phased array to obtain the full image. In FIG. 19A the array of striplines is sensitive to a magnetic field in the 'x' direction. In FIG. 19B, the array is sensitive to the 'y' direction. There are several possible methods (previously described) to feed striplines. In FIGS. 19A and 19B the feeding method is as per FIG. 16C. Preamplifiers and the remainder of the magnetic resonance imaging system are not shown.

In the radial arrangement, shown in FIG. 19C, the striplines are all above a common ground plane. In this example figure, 4 striplines are shown, each with a pair of tuning capacitors to adjust the resonant frequency. The striplines are not making electrical contact, and are separated vertically. The striplines are fed as per FIG. 16C. Again, not shown are preamplifiers or any further elements of a magnetic resonance imaging system. The output from each stripline are combined to form an image as a phased array coil.

2.4.4 Loop Coils

Figure 20A:
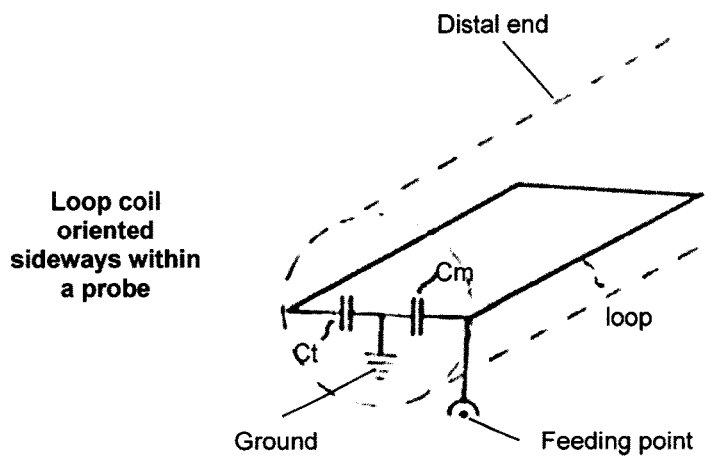
FIGS. 20A-D illustrate various example implementations of a loop coil configuration.

FIGS. 20A-D illustrate various example implementations of a loop coil. The loop coil may be beneficial given its high Q, accompanying high SNR, and versatility. In FIG. 20A, a loop is oriented sideways in a probe. The distal end of the probe is into the page, and the feeding location is at the location of the semi-circle. Two capacitors (Ct and Cm) are used to tune the loop to the appropriate resonant frequency. Not shown are any additional matching components that would be used to noise match the loop to a preamplifier. Also not shown are any preamplifiers which could be located separately (or, alternatively, formed within the probe). The feedpoint is located across Cm.

Figure 20B:
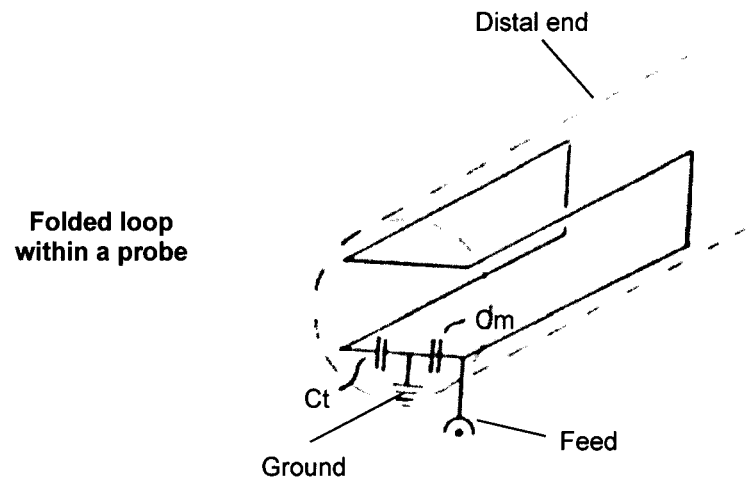

In FIG. 20B, a folded loop locates the fold at the tip of the probe to allow for the maximum forward looking sensitivity. Two capacitors (Ct and Cm) are used to tune the loop to the appropriate resonant frequency. Not shown are any additional matching components that would be used to noise match the loop to a preamplifier. Also not shown are any preamplifiers which could be located separately (or, alternatively, formed within the probe). The feedpoint is located across Cm.

Figure 20C:
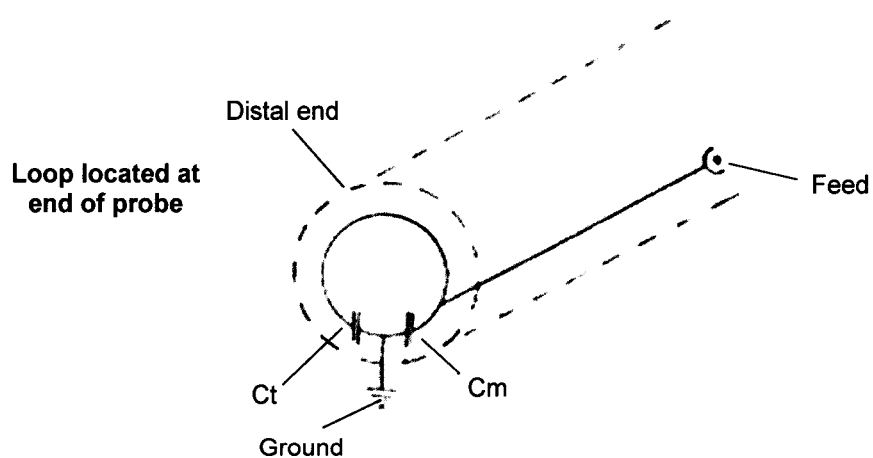

A loop coil may be included within the tip of a probe, as in FIG. 20C. This loop could have varying diameters to increase the intensity of the forward-looking imaging region. The diameter of the loop may range from micrometers to centimeters. The loop coil may be constructed from conducting material, as previously outlined, and may be backed by a dielectric substrate. In FIG. 20C the loop is tuned with capacitive elements (such as Cm and Ct), and is fed across capacitor Cm. Not shown are any preamplifiers which could be located separately (or, alternatively, formed within the probe).

Loop coils may be used in an array, and may be decoupled from other elements within the array either geometrically or with capacitive or inductive components.

Figure 20D:
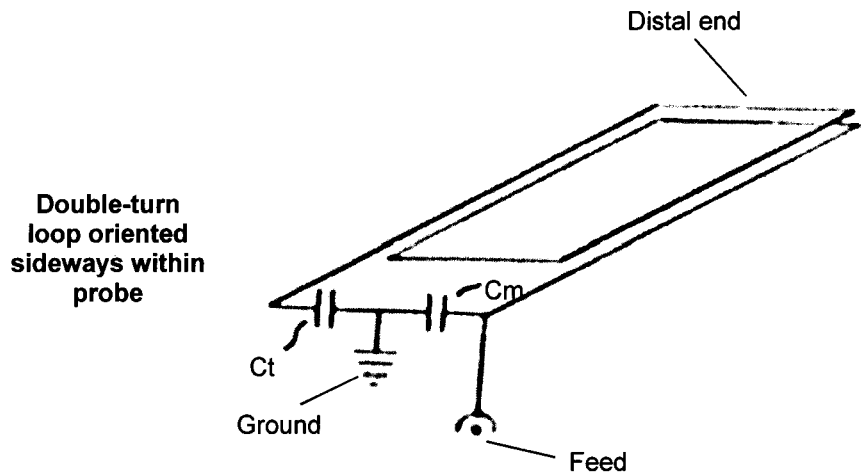

FIG. 20D shows a two-turn coil, oriented sideways within a probe. The two-turn loop coil uses capacitors Cm and Ct to tune the coil to the resonant frequency of the system. The feedpoint is located across capacitor Cm. Not shown are any preamplifiers which could be located separately (or, alternatively, formed within the probe). It will be understood that in alternate embodiments, any number of turns may be employed.

Figure 21A:
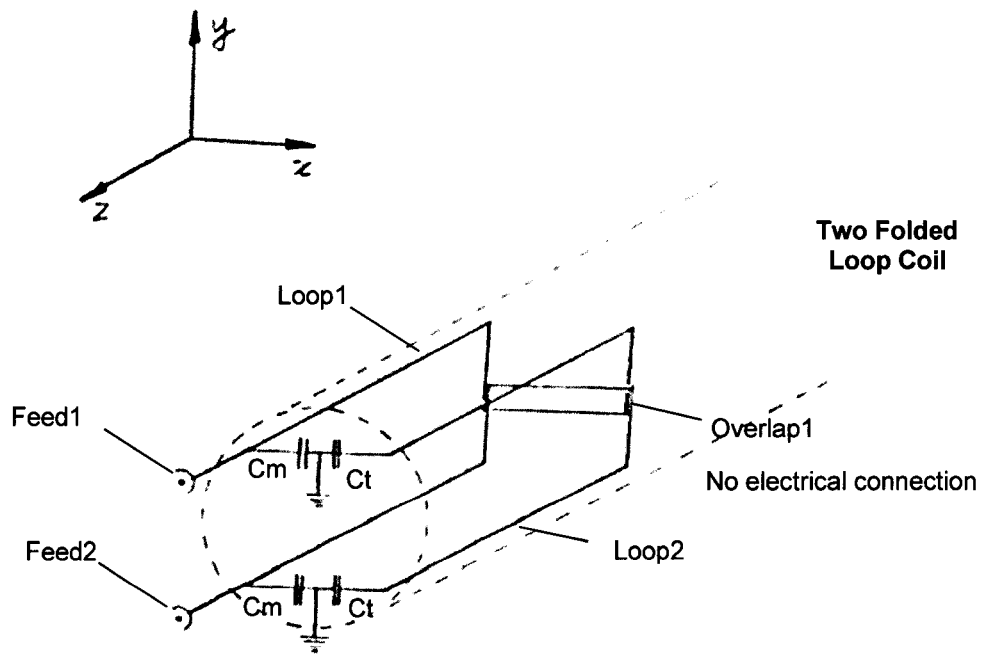
FIGS. 21A-B illustrate example coil loop implementations involving (A) two and (B) four folded loop coils that are provided at or near the distal portion of the MR imaging probe.
Figure 21B:
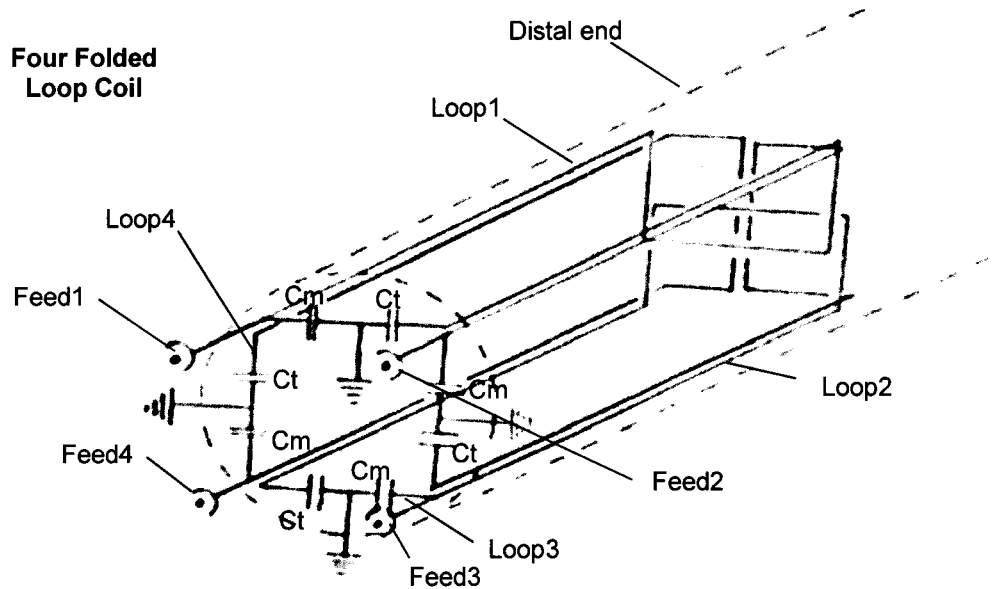

FIGS. 21A-B illustrate example coil loop implementations involving (A) two and (B) four folded loop coils that are provided at or near the distal portion (e.g. the tip) of the MR imaging probe in order to enhance the forward looking aspect of the probe.

In FIG. 21A, two folded loops arranged so that their folds are located at the distal end of a probe to maximize their forward looking sensitivity. The two loops are overlapped so as to cancel their mutual inductance to decouple the two loops. There is no electrical connection made at the overlap. It is also understood that in alternate embodiments, capacitors of inductors could be used to decouple the loops. Each of the loops is equipped with a pair of capacitors for tuning and a feeding location. Not shown are any noise matching circuits, or any decoupling diodes, or any preamplifiers that might be used to amplify the signal. The feedpoints for each loop are located across capacitor Cm.

FIG. 21B is similar to FIG. 21A showing 4 loops. Again, all loops are overlapped to decouple them, without forming an electrical connection. As in FIG. 21A, other decoupling methods are possible, such as using shared capacitors, or inductors. Each loop is equipped with a pair of capacitors for tuning as well as a feeding location. Not shown are any noise matching circuits, or any decoupling diodes, or any preamplifiers that might be used to amplify the signal. The folded ends are located at the distal end of the probe.

2.4.5 Butterfly Coils

In some embodiments, one or more coils of the MR imaging probe may be provided in a butterfly coil configuration. For example, butterfly coils may be provided within the MR imaging probe in a planar configuration or in a folded configuration (to improve the forward-looking imaging aspects of the coil). Example implementations of butterfly coil configurations are, shown in FIGS. 22A-C.

Figure 8:
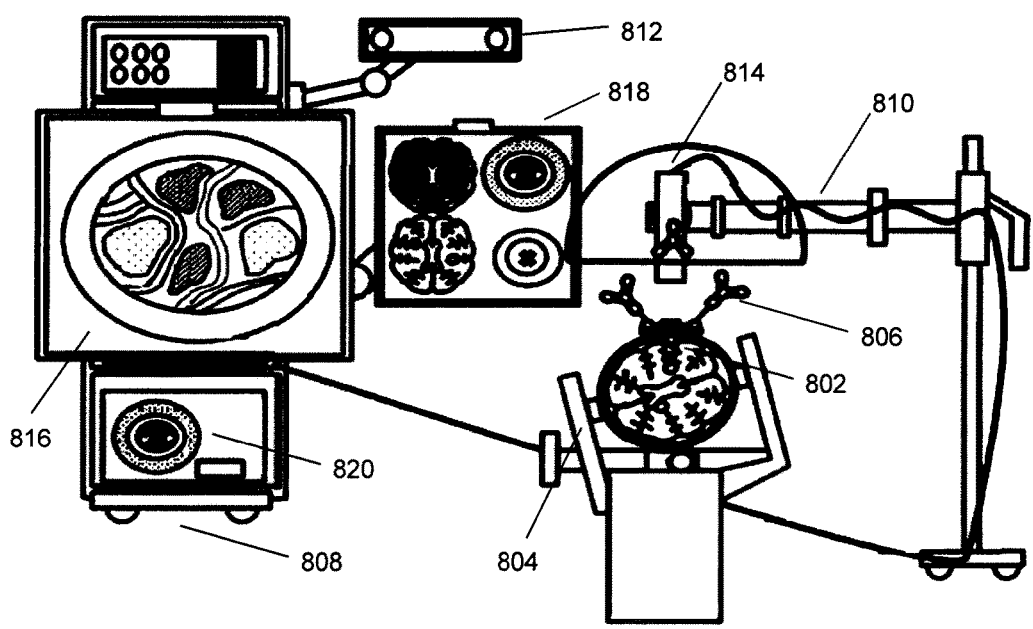
FIG. 8 is an illustration demonstrating an example simplified neurosurgical configuration.
Figure 22A:
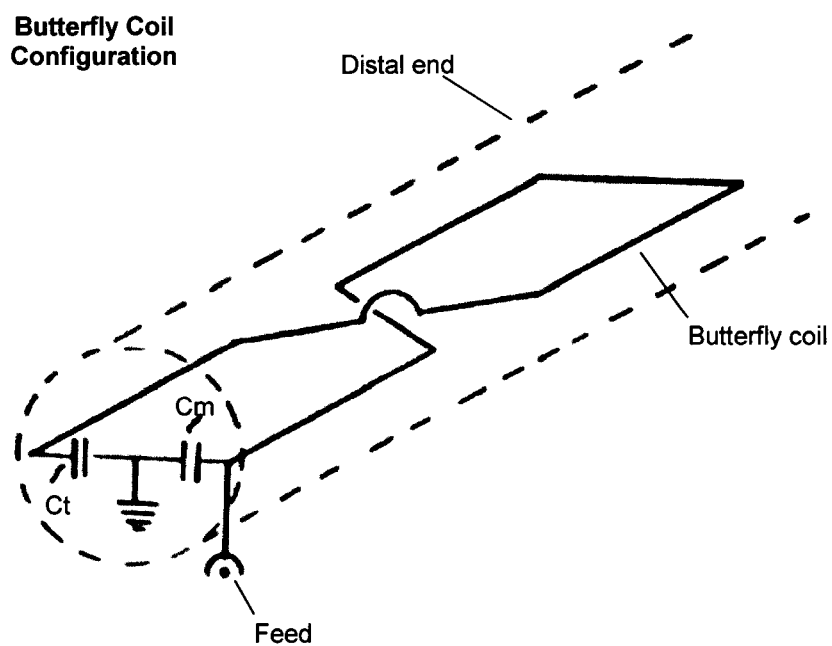
FIGS. 22A-C illustrate three example coil implementations involving butterfly coil configurations.
Figure 22B:
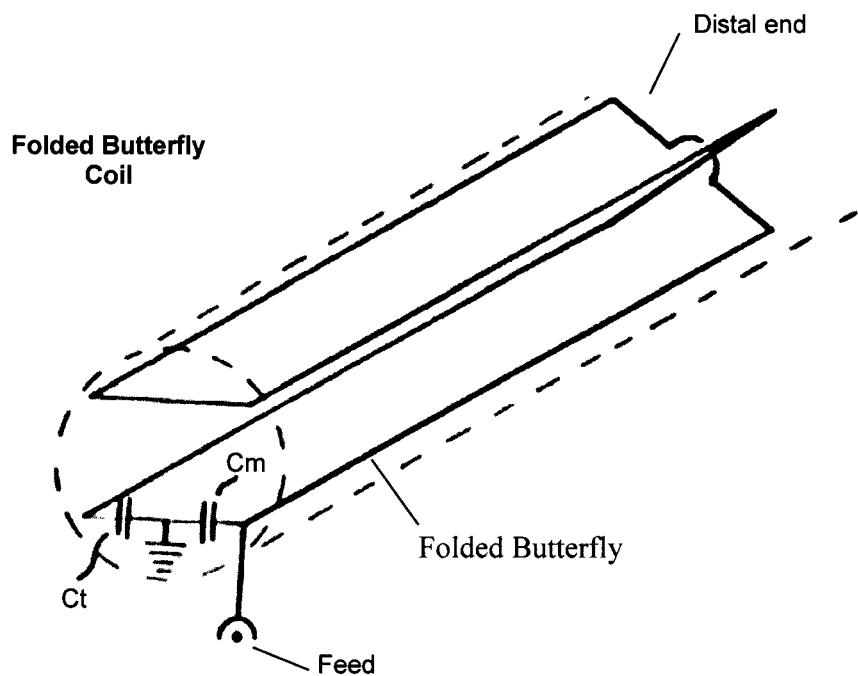

FIG. 22A shows a butterfly, or figure-8 coil. Here it is shown located along the length of a port. Two capacitors, Cm and Ct, are used for tuning the coil to the appropriate resonant frequency, and the feeding location is indicated by the semicircle. This coil will be sensitive to areas above and below it. Not shown are any noise matching components, control signals, detuning elements, or preamplifiers. FIG. 22B also shows a folded butterfly coil. The fold is located at the distal end of the probe to maximize the forward looking area. No electrical connection is made at the fold location. Two capacitors, Cm and Ct, are used for tuning the coil to the appropriate resonant frequency, and the feeding location is indicated by the semicircle. Not shown are any noise matching components, control signals, detuning elements, or preamplifiers.

Figure 22C:
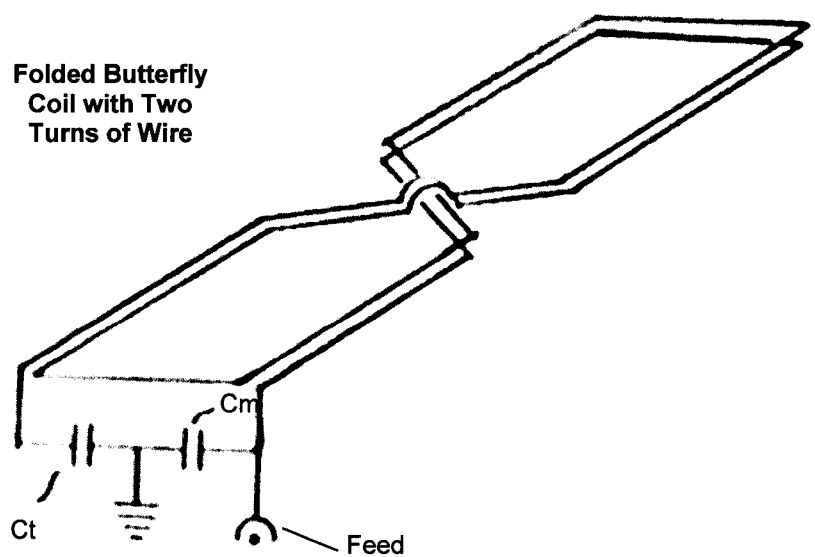

FIG. 22C shows a butterfly coil with two turns of wire. Two capacitors, Cm and Ct, are used for tuning the coil to the appropriate resonant frequency, and the feeding location is indicated by the semicircle. This coil will be sensitive to areas above and below it. Not shown are any noise matching components, control signals, detuning elements, or preamplifiers. No electrical connection is made between the two turns of the coil, save through the capacitors Cm and Ct.

As with other coil geometries described here, the coil dimensions may be scaled from micrometers to centimeters (e.g. from approximately 1 micron to approximately 1 cm) in diameter and micrometers to centimeters in length.

The butterfly coil may have any number of turns, and may be positioned either radially surrounding the port, such that each butterfly is rotated around the axis that runs along the length of the port or along the length. The coil butterfly is constructed from a conducting material and may be formed upon a dielectric substrate. As noted above, the probe material should be formed using a material with a good susceptibility match to water. The butterfly coil may be decoupled from other elements in a coil array through geometric positioning or capacitive/inductive elements.

2.5 Arrays

The preceding embodiments described several example implementations of coil configurations that may be employed in an insertable MR imaging device, such as an insertable MR imaging probe. It will be understood that coils according to these configurations, or according to variations thereof, may be provided in an array form.

2.5.1 Sparse and Dense Arrays

In some embodiments, an array may be formed by providing, on or within an insertable MR imaging device, a plurality of coils in a prescribed spatial arrangement. The array of coil elements which combine to form the port coil may be provided according to many different embodiments without departing from the scope of the present disclosure. Example embodiments feature an array of RF elements to enable parallel imaging where the sensitivity of each element is used to accelerate imaging times. These arrays may be used as receive-only, transmit-only, or in combination as a transceiving device. In transceiving mode, an electrical switch is included in order to toggle between the receiving and transmitting circuits. Examples involving parallel imaging include asymmetric g-factor, using phase encoding in one direction, driving gradients in opposite direction.

In some embodiments, the array may be a dense array (e.g. a high-density array). As used herein, the phrase "dense array" refers to an array having a relative spacing between neighboring array elements of less than approximately 1 mm and the phrase "sparse array" refers to an array having a relative spacing between neighboring array elements of greater than approximately on the order of 1 cm. For example, FIG. 25 illustrates an example implementation of an insertable MR imaging probe having a dense array of striplines.

In some embodiments, the array elements of a dense array may form a phased array. In a phased array, each coil has a spatially separate region of sensitivity.

Within the array, each element may be tuned to the Larmor frequency of the nuclei under investigation using non-magnetic capacitive components as required. These elements may have multiple tunings to enable collecting data from numerous nuclei. The desired tuning can be selected actively by way of an electronic switch that includes the appropriate tuning capacitors within the circuit. The Larmor frequency is proportional to the applied magnetic field strength, and as such, the imaging array can be designed to operate at varying field strengths, whether it be a low-field or high-field application. To maintain isolation between the channels corresponding to various coil elements, the coil elements are decoupled from each other, for example, either capacitively, geometrically, or inductively within the circuit. The plurality and placement of the capacitive and/or inductive elements are dictated by individual coil geometries. Where appropriate these components may be placed in the handle.

Figure 27:
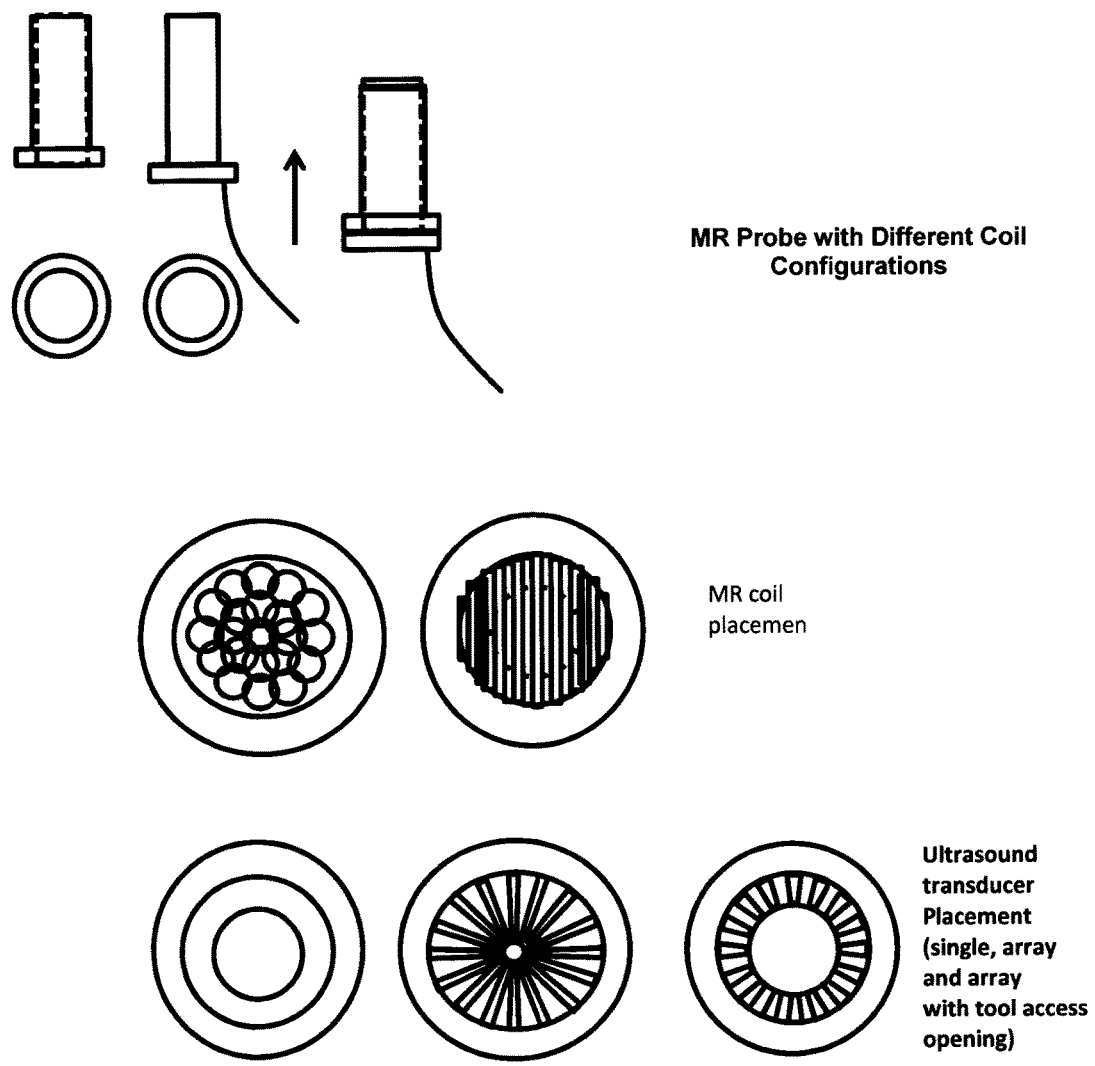
FIG. 27 illustrates an example implementation of an insertable MR imaging probe having an array of loop coils arranged near a distal surface of the insertable MR imaging probe, in a configuration for end-fire array-based imaging.

In one embodiment, the imaging device may include a dense array of MRI receiver coils, such as an array of stripline coils as in FIGS. 19A-C. In another example implementation of an array configured for end-fire imaging, an insertable MR imaging probe may include an array of multiple loop coils, as shown in FIG. 27. In this manner, a forward-looking imaging field can be imaged, for example, with a high sensitivity, and with the ability to cover the field of imaging using many small array elements, which enables parallel imaging.

2.5.2 Combinations of Different Coil Configurations and Geometries

In addition to the aforementioned embodiments involving single and multiple coils of a given type, it will be understood that in other embodiments, a MR imaging probe may include multiple coil types, for example, to form a coil array.

For example, in some embodiments, two or more of loop coils, striplines, and butterfly coils can be combined within a MR imaging probe. In some embodiments, the coils that are combined may include one or more folded coils to generate an end-fire focused imaging area. The proceeding section presents several non-limiting examples of such combinations. It will be understood that these examples are non-limiting and that other configurations may be obtained by alternative combinations of two or more coil types.

Figure 23:
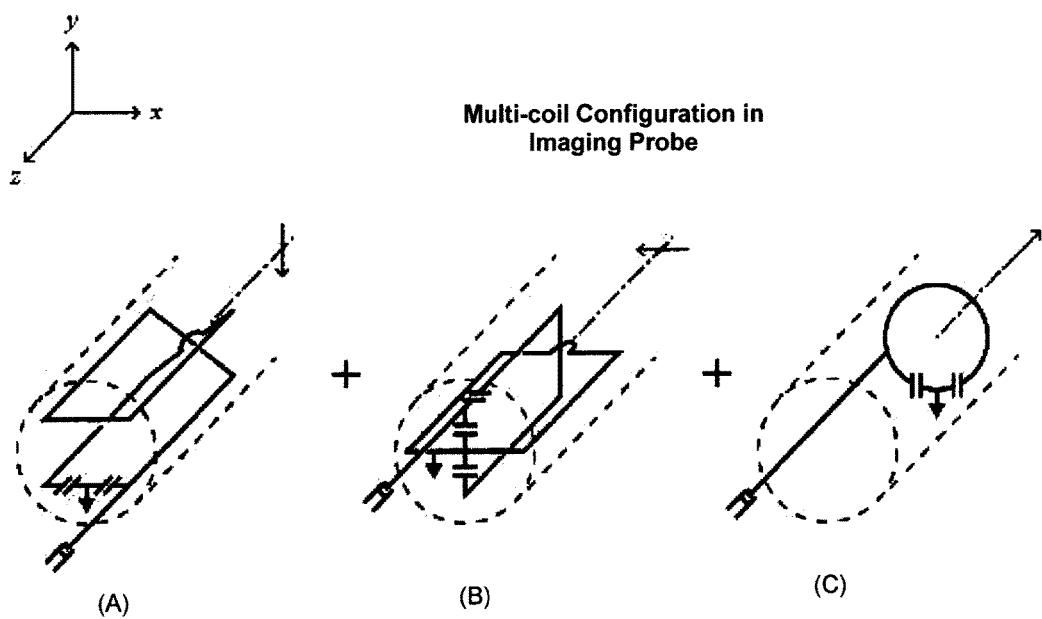
FIG. 23 illustrates an example implementation of an embodiment in which multiple coil types are combined within an MR imaging probe to produce a probe that is sensitive to magnetization beyond the distal region of the imaging probe.

An example in which the three aforementioned coil types are provided together in a geometrically decoupled fashion is shown in FIG. 23. The conductor may be a wire, or a planar conductor, etc. This arrangement is particularly attractive given that it generates $B_1$ fields (or is sensitive to a varying magnetic field) in x, y, and z. Therefore, this will provide a high resolution forward looking image regardless of its orientation with respect to the main magnetic field. The distal tip of the probe is into the page, as indicated by the arrows. All of these coils are inherently decoupled by being sensitive to orthogonal magnetic fields. FIG. 23 shows a separate view of three orthogonal coils that can be combined within 1 imaging probe. Coil 'A' shows a folded butterfly (as in FIG. 22B) sensitive to fields in the 'y' direction, coil 'B' shows a folded stripline coil (as in FIG. 6A), sensitive to fields in the 'x' direction, and coil 'C' shows a loop coil (as in FIG. 20C) sensitive to fields in the 'z' direction. All three of these coils may be combined in a single imaging probe due to the orthogonality of the fields that they are individually sensitive to.

Figure 24:
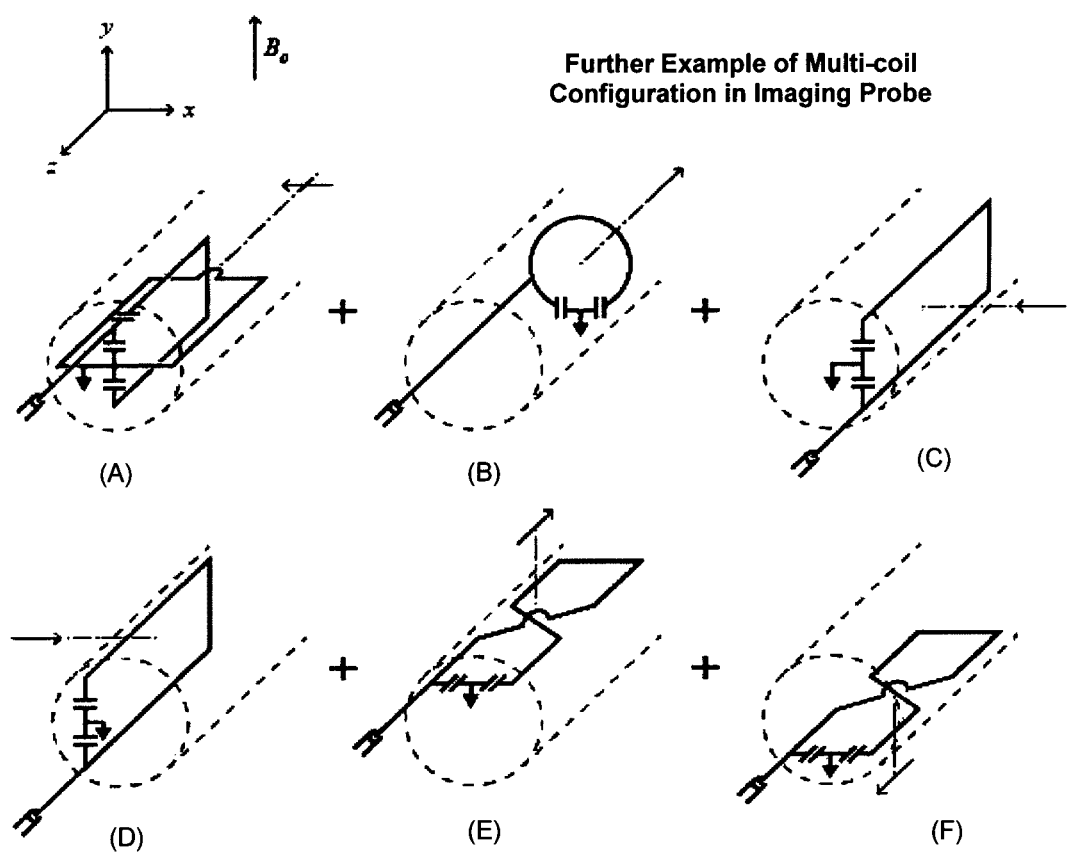
FIG. 24 illustrates an example implementation of an embodiment in which multiple coil types are combined within an MR imaging probe.

Another example implementation employs striplines, loops, and butterfly coils that are all arranged to be orthogonal to the $B_0$ field, as shown in FIG. 24. To allow for multiple channels orthogonal to the B0 field, a combination of coil geometries are used. Six different coil configurations are used to image to the left, right, above, below, and forwards of the imaging probe. To image forwards of the probe, coils 'A' and 'B' are used (folded stripline ('A') and loop ('B')), to image to the left of the probe, coil 'C' (sideways loop orientation), to image to the right of the probe, coil 'D' (sideways loop orientation), to image above the probe coil 'E' (butterfly oriented along probe), and to image below the probe, coil 'F' (butterfly oriented along probe). All these coils can be combined in a single imaging probe.

Adding more coils can improve performance. This arrangement uses two loops to look left and right, two butterflies to look up and down, and a loop and stripline at the tip. The end of the probe is located with arrows.

The coils are designed to receive signals along the x and z directions, and the coils are intended to be orientated such that the external $B_0$ field is directed along the y axis (based on appropriate orientation of the MR imaging probe, for example, according to a field orientation marker on the probe handle and/or probe body). Although 6 coils are shown in the FIG. 24, it will be understood that there are many such possible arrangements that may be achieved without departing from the scope of the present disclosure.

FIG. 27 illustrates an example embodiment in which an array of coils is provided at the distal end of an insertable imaging probe. Although the figure shows an array of loop coils, it is to be understood that an array of other coil types could be used, such as an array of striplines, butterfly coils, or any combination thereof.

Figure 28A:
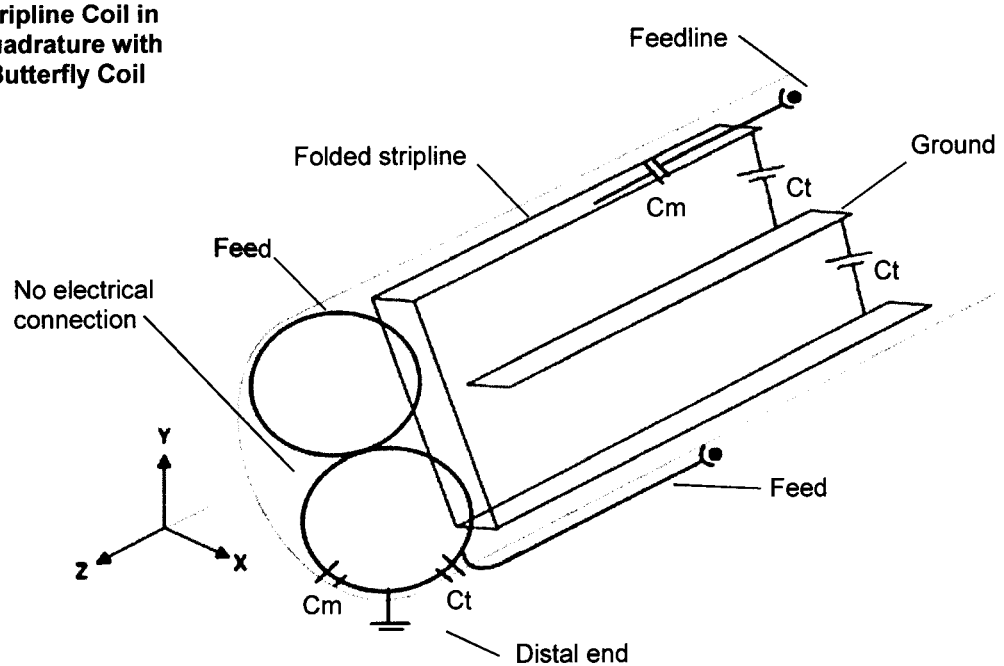
FIGS. 28A-B illustrate an example implementation of an imaging probe arranged to be in quadrature with butterfly arrays.

FIG. 28A illustrates an example embodiment in which a stripline coil is provided in quadrature with a butterfly coil located at the distal tip of a probe. The butterfly coil is tuned with capacitors Cm and Ct. The folded stripline is tuned with capacitors Ct and matched with capacitor Cm. The folded stripline is sensitive to fields in the 'x' direction, while the butterfly coil is sensitive to fields in the 'y' direction. This orthogonal sensitivity allows the coils to be inherently decoupled. Not shown are any preamplifier, or decoupling diodes.

Figure 28B:
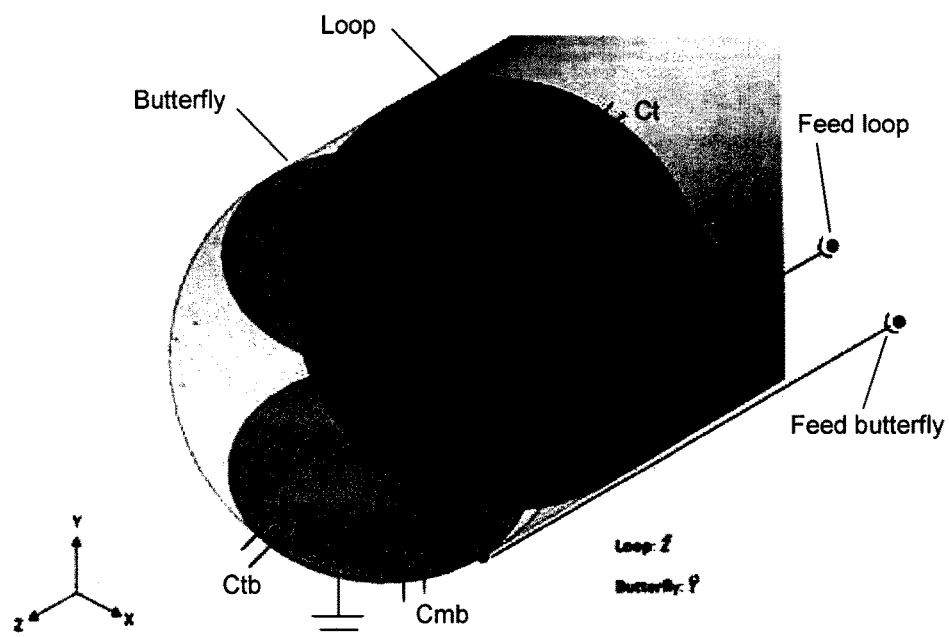

FIG. 28B illustrates an example embodiment in which a butterfly coil is provided in quadrature with a loop coil located at the distal tip of a probe. The butterfly coil is tuned with capacitors Cmb and Ctb, the loop is tuned with capacitors Cm and Ct. The butterfly coil is sensitive to fields in the 'y' direction while the loop is sensitive to fields in the 'z' direction. This orthogonal sensitivity allows the coils to be inherently decoupled. Not shown are any preamplifier, or decoupling diodes.

Figure 29:
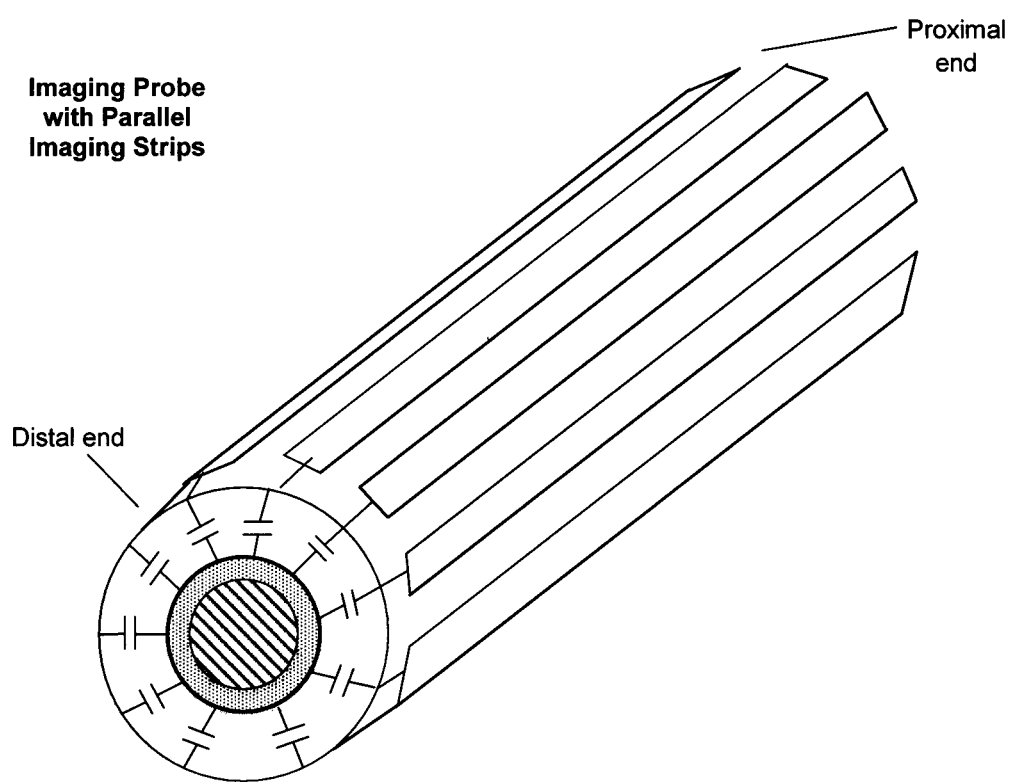
FIG. 29 illustrates an example implementation of an imaging probe aligned parallel to enable high parallel imaging factors in a single direction.

In FIG. 29, an array of stripline coils are placed parallel to the axis of the probe. The stripline coils may be placed equi-distant apart around the circumference of the imaging probe. Not shown are tuning capacitors from each stripline to a central ground at the proximal end of the probe, also not shown are the matching circuit (which could take either forms described above) or preamplifiers, or blocking diodes. Using an array of striplines allows the coil to obtain higher SNR in the areas immediately next to the imaging probe, though this geometry is more sensitive radially than forward looking.

Figure 30:
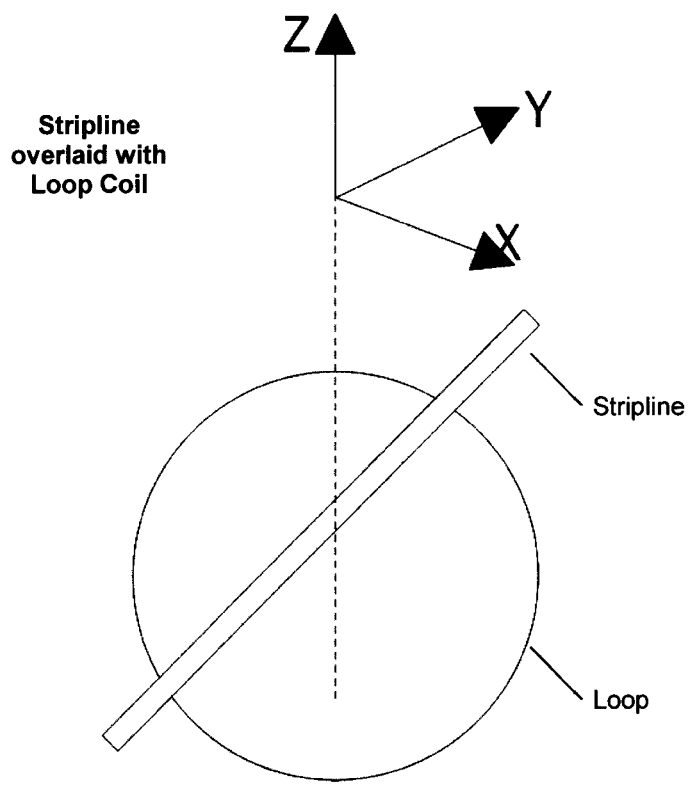
FIG. 30 illustrate an example implementation of an imaging probe having strip line coil overlaid with a loop coil.
Figure 31A:
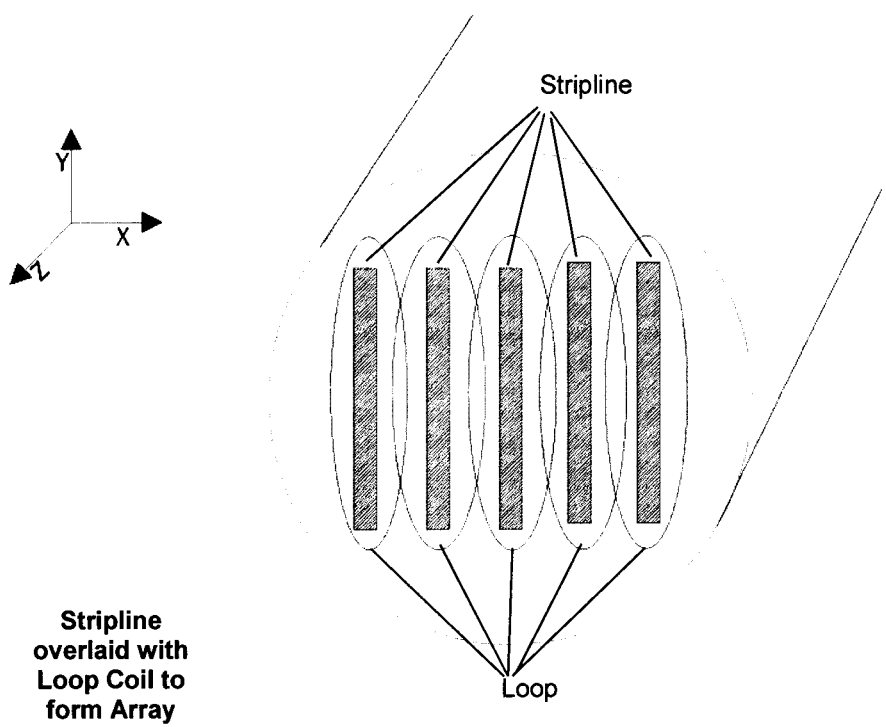
FIGS. 31A-B illustrates an alternate embodiment where each stripline coil is overlaid with a loop coil to form an array.
Figure 31B:
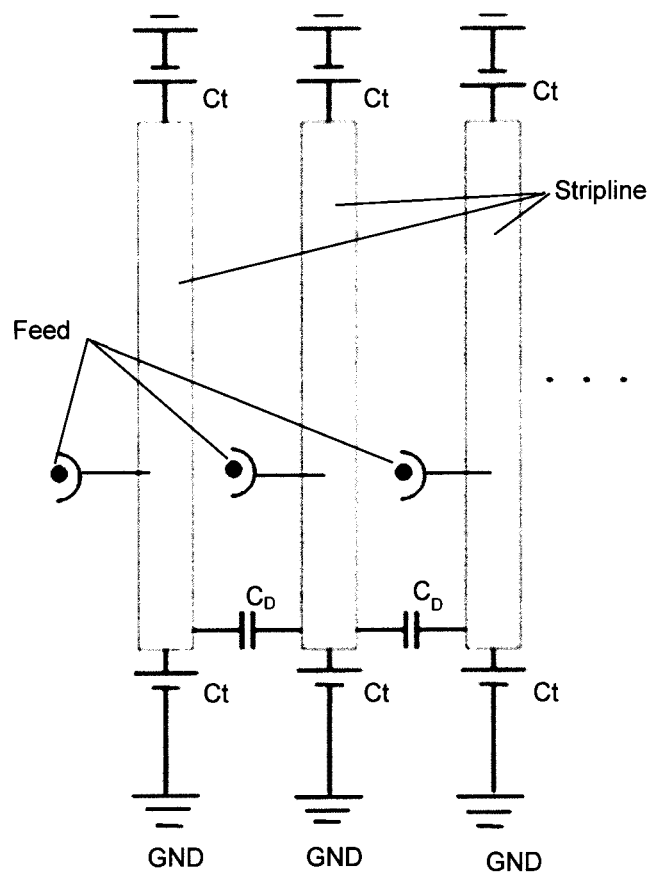

Another example embodiment is illustrated in FIGS. 30 and 31 in which striplines in an array are overlaid with loop coil configurations. Stripline coils and loop coils are inherently decoupled. FIG. 30 illustrates a stripline coil and loop coil combination configuration. In this figure, the stripline is sensitive to a field in the 'x' direction while the loop is sensitive to a field in the 'z' direction. Not shown are tuning/matching circuits, preamplifiers, blocking diodes, etc. The stripline requires a ground circuit (not shown). FIG. 31A illustrates an alternate embodiment where each stripline coil is overlaid with a loop coil to form an array. Not shown are tuning/matching circuits, preamplifiers, blocking diodes, etc. Each stripline may have a ground below it, or all striplines may share a common ground. FIG. 31B is a further elaboration of FIG. 31A that illustrates an exemplary array circuit that indicates the use of decoupling capacitors (Cd) between elements of a planar stripline array. Each stripline is tuned with two capacitors (Ct) and fed as per FIG. 16C. Each stripline may have a ground, or they may all share a common ground plane (not shown).

2.5.3 Increasing Parallel Imaging through Automatic Coil Detection

In some embodiments, the insertable MR imaging probe may be employed for parallel imaging, which is a technique used in MR to reduce the acquisition time. This is accomplished by providing multiple receiving coils, each receiving signals from a slightly different spatial area. Parallel imaging may be performed in either the slice direction, the frequency direction, or the phase encoding direction.

Parallel imaging will be most effective when the body portion of the probe is oriented such that the phase encoding direction of the scanner is perpendicular to the axis of the striplines. However, due to the variances of neurosurgery, the direction of the port often cannot be known in advance, nor can it be fixed.

To still allow for maximum parallel imaging, a navigation system can be used to track the location of the port relative to the patient, and the scanner can then choose an oblique slice. Typically, in MR scanners, the scan planes are chosen in standard orthogonal planes, i.e. axial, sagittal, and coronal. However, it is possible to scan in any plane (referred to as an oblique plane) by choosing the gradients correctly. In order for the scanner to know the direction of the port, the port coil must be tracked, typically by optical means.

An MR image typically has two axes—the frequency axis, and the phase axis. Parallel imaging can be used (but not exclusively) to speed up the time of acquiring the phase axis. The frequency axis and the phase axis can correspond to a real axis, such as 'x', or 'y', or 'z', or any arbitrary direction. If an array of coils was placed in a scanner such that each coil was arranged on a line that did not correspond to the scanner's definition of 'x', 'y', or 'z', it could be advantageous to define an oblique reference plane so that the axis of the coils does lie along this plane. This will allow maximum time improvement using parallel imaging. The combination of knowledge of the port's orientation obtained from an optical tracking system with the knowledge of the scanner's reference planes will allow a user to vary the scan parameters such that the oblique angles chosen by the scanner maximize the parallel imaging capacity.

2.5.4 Rotatable Forward-Looking Coil Element

In another embodiment, the forward-looking imaging capability of an MR insertable imaging probe may be extended by providing a means or mechanism for rotating the tip of the coil.

Figure 32:
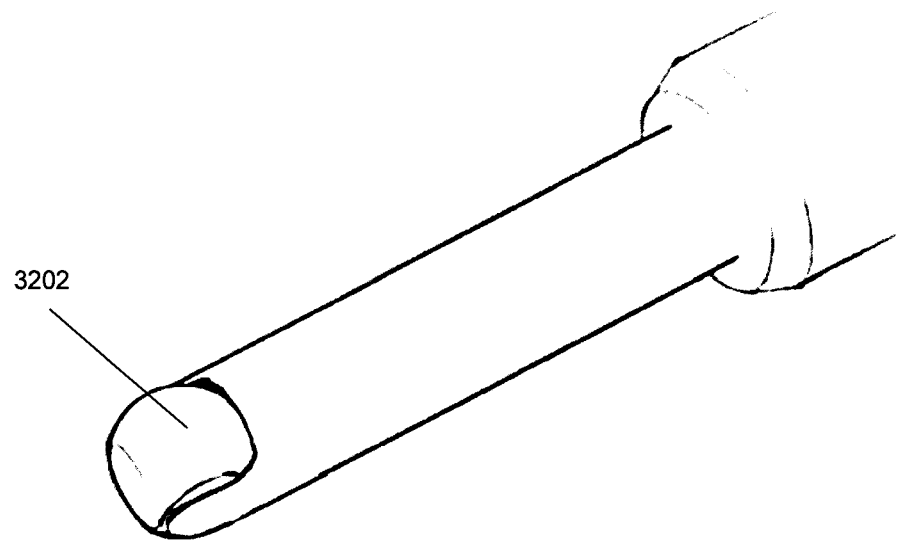
FIG. 32 shows in example implementation of an insertable MR imaging probe having a swivelling tip.

An example of this is shown below where a swiveling tip housing the coil elements rotates to increase the imaging angle. For example, the coil elements may be enclosed within a rotating head 3202, as shown in FIG. 32. FIG. 32 shows in example implementation of an insertable MR imaging probe having a swiveling tip housing the one or more imaging elements, where the tip rotates to increase the imaging angle. The mechanism could be a physical connection such as a set of gears, or pulleys, or pulling cables.

Figure 33:
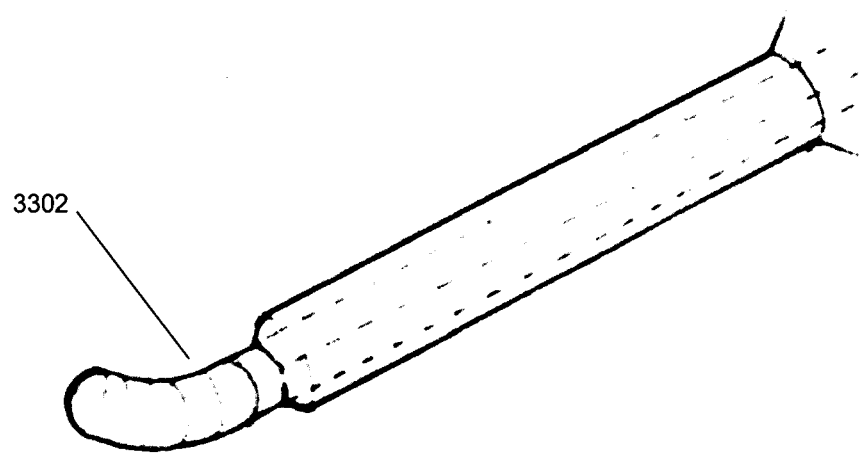
FIG. 33 illustrates an example implementation in which the probe tip includes a wrist rotatable in varying angles.

Another example option depicted demonstrates that by creating a joint between the body of the port coil and its tip, or an articulated mechanism 3302 or wrist as shown in FIG. 33. FIG. 33 illustrates an example implementation in which the probe tip includes a wrist such that imaging elements within the tip can rotate about to image at varying angles. The elements within the tip can rotate about to image at varying angles, which may allow the probe to be employed to acquire high resolution images of a larger end-fire area about the port, resulting in superior imaging and increased imaging penetration.

Variable bending of the port tip can be also achieved through the use of oppositely placed cables located along the wall of the bendable portion. Such an insertable MR imaging probe can also have an orifice along the axis to allow the introduction of surgical tools through this access point. This embodiment may be used within a surgical channel and is particularly attractive to image endo-nasally.

Figure 34:
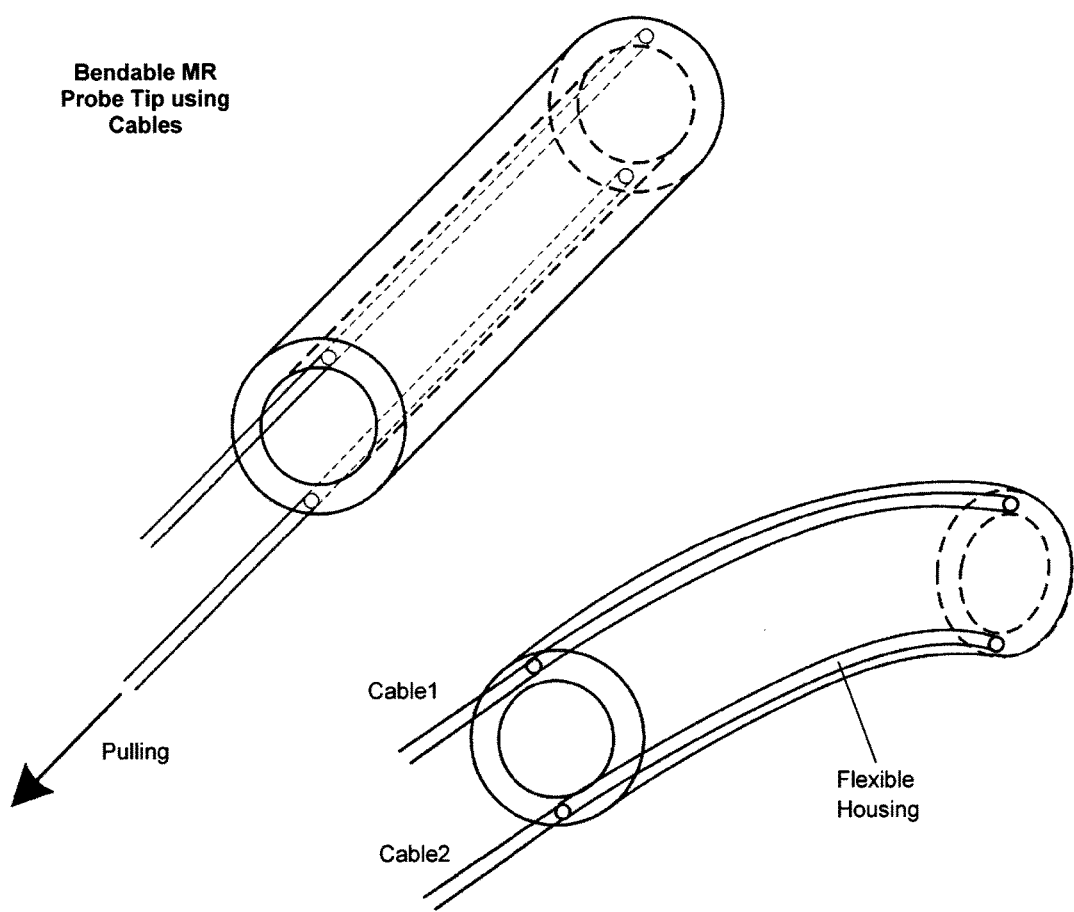
FIG. 34 illustrates an example implementation of an insertable MR imaging probe in which variable bending of the probe tip is achieved through the use of oppositely placed cables located along the wall of the bendable portion.

FIG. 34 illustrates an example implementation of an insertable MR imaging probe in which variable bending of the probe tip is achieved through the use of oppositely placed cables located along the wall of the bendable portion. As shown in FIG. 34, cables are inserted through the probe wall. The cables are securely attached to the distal end of the probe, but not to the proximal end. With a flexible housing, when one cable is pulled with greater force than the other, and the proximal end of the probe is fixed, a bending motion is achieved. If more than 2 cables are used, motion in two directions can be achieved. With 2 cables, motion is in one dimension only.

It should be noted that the same functionality of scanning a broad range of angles through the end-fire area can be achieved with a rigid probe with one wrist and one elbow joint. The joints can be actuated using electromechanical actuators or mechanical actuators such as gears, cables and pulleys.

Although the present embodiments, with a rotating or swiveling distal portion of the probe, pertain to insertable MR imaging probes, it will be understood that they may be extended or adapted to insertable imaging probes employing other imaging modalities, such as optical and ultrasound imaging.

2.5.5 Insertable MR Imaging Probe with Expandable Forward-Looking Coil Elements

Figure 35:
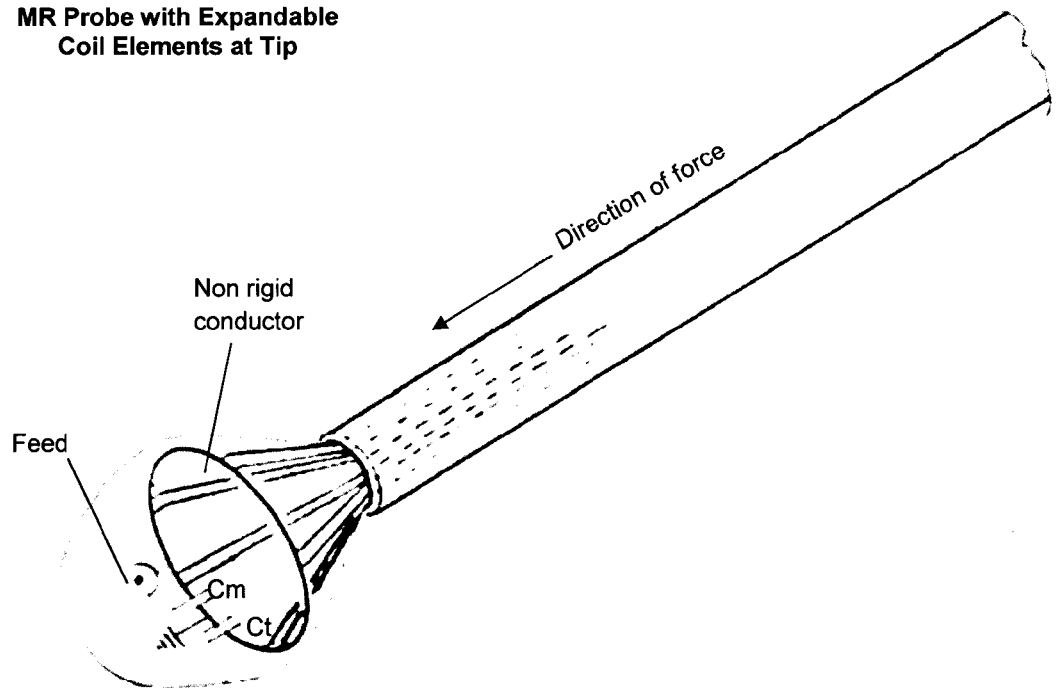
FIG. 35 illustrates an example insertable MR imaging probe having a forward-looking (e.g. end-fire) configuration, where the distal region of the probe body includes one or more expandable coil elements.

FIG. 35 shows an example embodiment of an insertable MR imaging probe having a forward-looking (e.g. end-fire) configuration, where the distal region of the probe body includes one or more expandable coil elements. As shown in FIG. 35, the coil elements may be housed within a balloon or inflatable/expandable pouch. In one example implementation, once inserted, the balloon may be expanded to create a region, for example, of up to 5 cm in diameter, in order to accommodate the expanding coil structure.

The example embodiment shown in FIG. 35 shows a loop that is constructed from a non-rigid subsection of the conductive materials described herein and attached to mechanical arms that serve to open the coil up to its full size within the ballooned region. In doing so the forward-looking imaging depth of penetration is increased. Any flexible conductive material could be used for the coil. This could be, for example, wire, cable, or any flexible tape. In FIG. 35, the loop is shown tuned with two capacitors Cm and Ct, and fed across capacitor Cm. Not shown are any preamplifiers, blocking diodes, or other elements of the magnetic resonance imaging system.

2.6 Access Ports with Embedded Coils

The preceding embodiments of Section 2 have disclosed various example insertable MR imaging probes. In several of the forthcoming portions of Section 2, alternative embodiments are described in which one or more coils (e.g. coil elements) are formed on or within an access port, or a sleeve that is insertable into an access port, as initially described in Sections 1.3 and 1.4.

In one embodiment, one or more coil elements are formed on, or embedded within, an access port, thus providing a hollow imaging sleeve wherein instruments such as surgical tools can be inserted during a medical procedure. This provides an entry point for other imaging devices, MR guided therapies, or contrast agent administration. This may include biopsy tools, deep brain stimulation devices, thermal imaging equipment, or ultrasound devices among others.

Figure 36A:
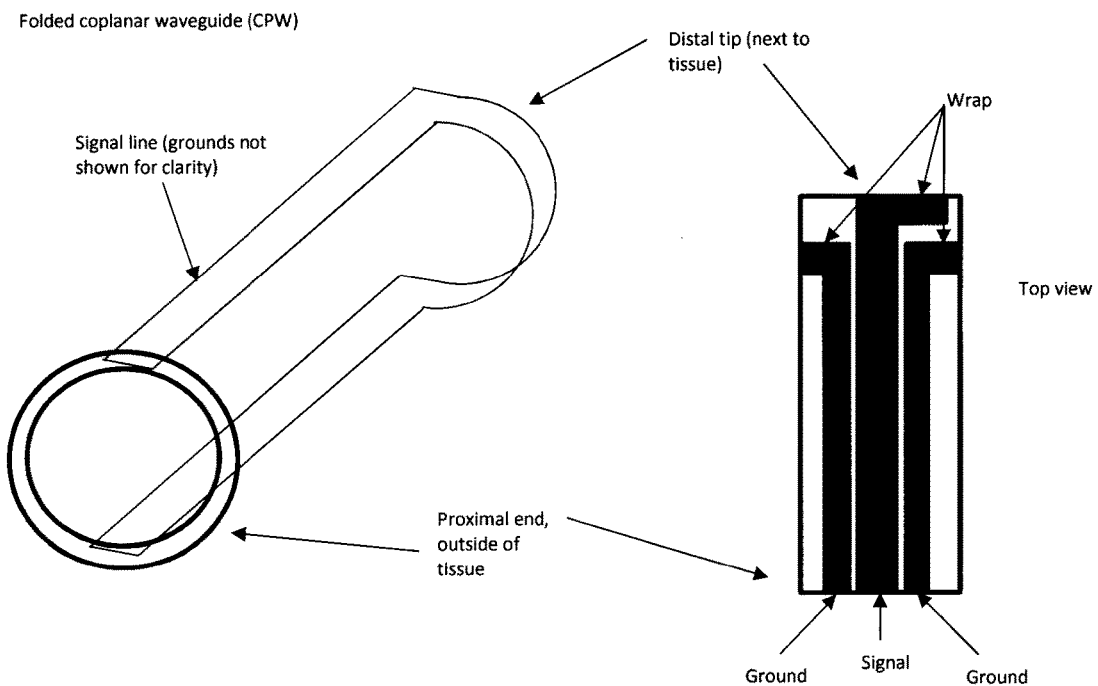
FIGS. 36A-36D illustrates an example of embedding coils in the side walls of a port.

FIGS. 36A-36D illustrates embedding the coils in the side walls of the port. Here, instead of the resonant microstrip lines of the previous embodiment, this uses coplanar waveguide as the resonator. Coplanar waveguide is a type of transmission line where the ground and signal lines are arranged side-by-side in the configuration ground-signal-ground. This allows for a channel to be open within the port. This technique is compatible with the previously mentioned ability to locate some components within the handle, and some within the port itself. In FIG. 36A, all tuning, matching, and receiving equipment is located within the handle, and attached when it is time to scan. The handle makes electrical connection with the signal and ground lines indicated in FIG. 36A.

Figure 36B:
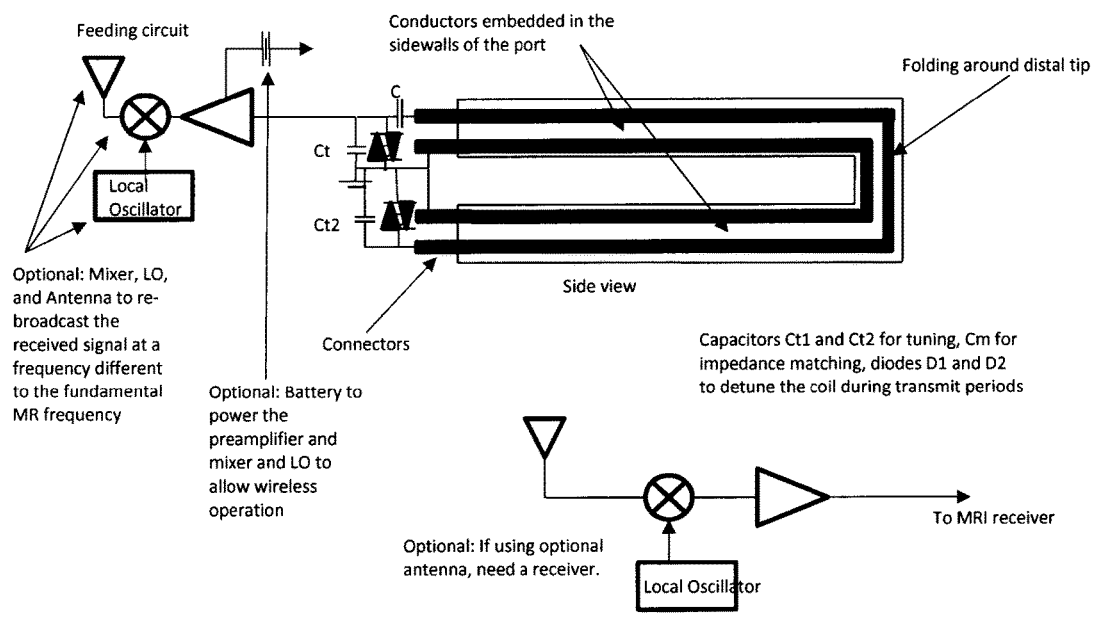

In FIG. 36B, the coil communicates wirelessly with the scanner, eliminating the cable from the port coil to the scanner. In order to achieve this, further circuitry is required to upconvert the signal, and to transmit at a frequency different from the larmor frequency using a local antenna. A further antenna is required to receive the signal, and further electronics are required to downconvert and amplify the signal before passing the signal to the MR receiver.

Figure 36C:
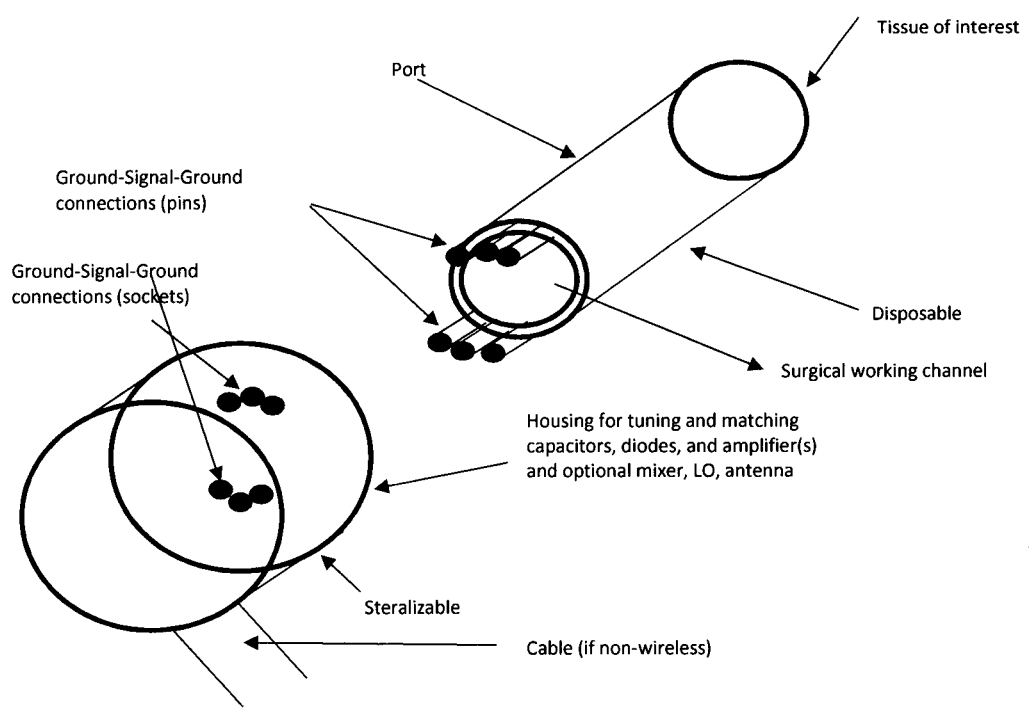

FIG. 36C shows a detail of FIG. 36A indicating how the connection from handle to probe is made. Contacts are made at all ground and signal connections, and tuning, matching, and receiving elements are contained within the handle portion, as described earlier.

Figure 36D:
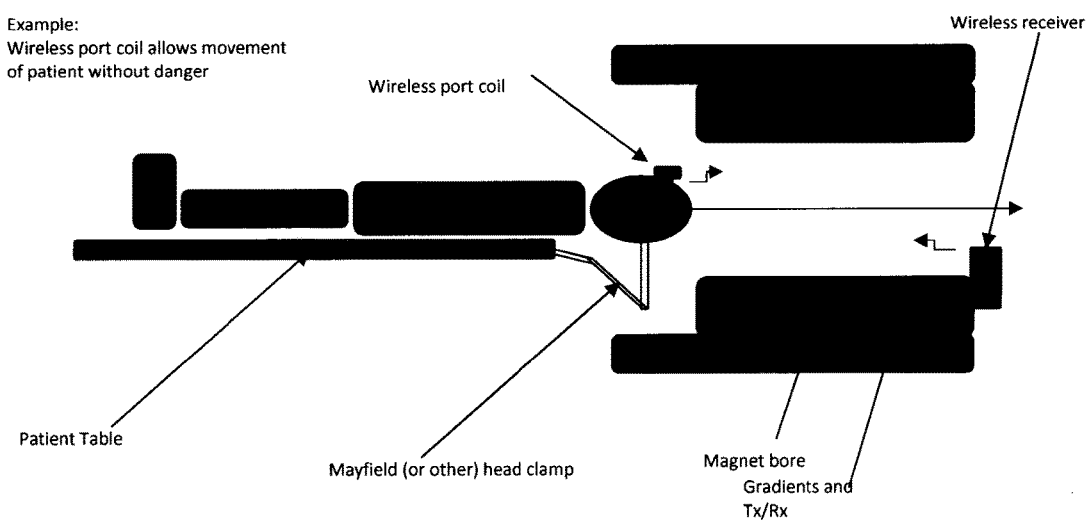

FIG. 36D describes a detail of FIG. 36B indicating possible locations for a receiving antenna to be used in a wireless coil setup. In this example, one antenna is located within the handle of the port coil, and another, receiving antenna, is located at the far end of the magnet bore. However, there are many possible antenna locations that would also accomplish the same objective.

The embodiments below illustrate a non-limiting set of other example implementations of access ports with integrated imaging coils.

2.6.1 Examples of Access Ports with Integrated Coils

Figure 38A:
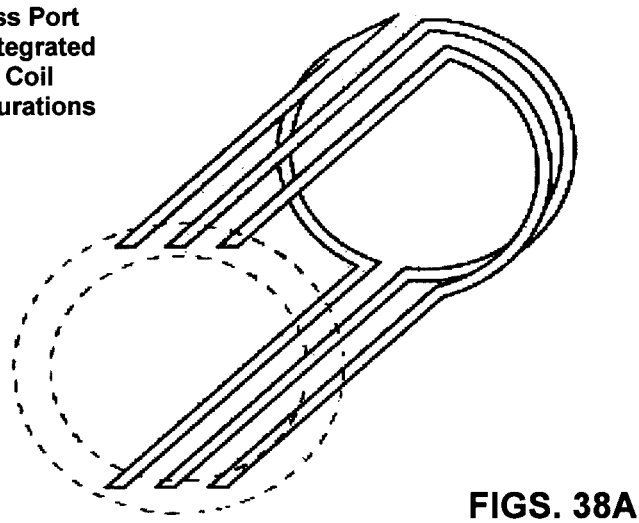
FIGS. 38A-D illustrate various example implementations of access ports with integrated MR coil arrays.
Figure 38B:
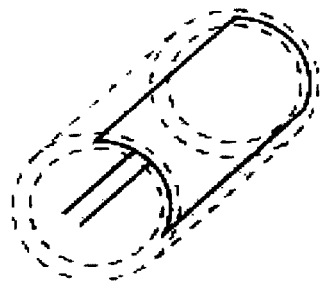
Figure 38C:
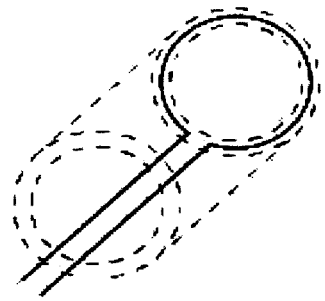

FIGS. 38A-D illustrate various example implementations of access ports with integrated MR coil arrays. FIGS. 38A-C indicates 3 example imaging probes that allow for access ports. In FIG. 38A, a folded coplanar stripline coil (as described above) is shown. In FIG. 38B, a sideways looking loop coil is shown. In FIG. 38C, a loop is show at the tip of the probe, with an open channel through the center of the loop. Further, all of these examples from FIGS. 38A-C, could be combined with other coils to form arrays.

Figure 38D:
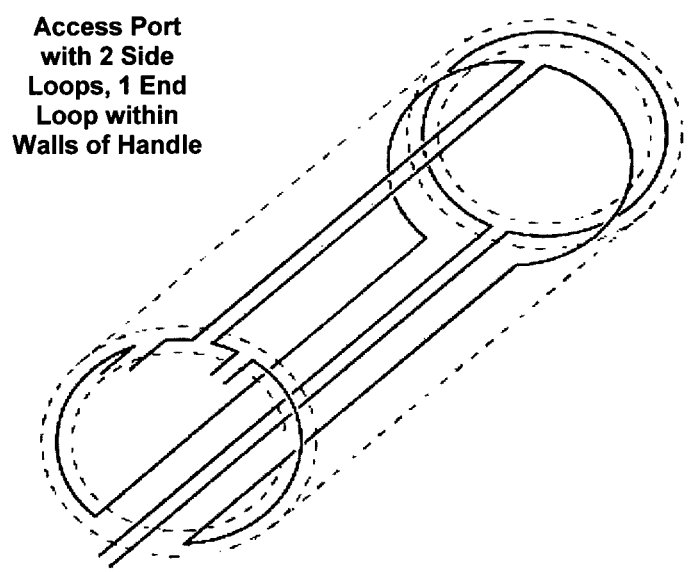

FIG. 38D illustrates an access port with two side loops and an end loop configuration with the coils embedded within the walls of handle, giving an access port through the center, as well as visualization to the left, right, and forwards of the imaging probe.

A central ground is not required for a stripline coil if it is formed as a coplanar waveguide (type of transmission line). In this version, the ground, instead of being below the signal line, is located to the left and right of the signal line.

2.7 Intermediate Imaging Sleeve Insertable into Access Port

In other embodiments, an imaging sleeve with one or more integrated MR coils may be provided, where the imaging sleeve is insertable into an access port, thereby providing a reconfigurable and optional means of port-based-imaging while still providing a central bore that provides access (direct or indirect) to internal tissues. This embodiment was introduced in Section 1.4.

In one embodiment, one or more coil elements are formed on, or embedded within, a sleeve that is slidably received within an access port, thus providing a hollow imaging sleeve wherein instruments such as surgical tools can be inserted during a medical procedure. All the geometries with hollow openings are applicable here.

2.8 Embodiments with Combinations of Multiple Insertable MR Imaging Devices

Finally, it will be understood that, as described in Section 1.5 (and in Sections 1.5.1-1.5.5), additional embodiments may be provided by combining two or more of the above insertable imaging devices.

For example, in one example implementation, an insertable imaging apparatus may include one insertable imaging device that includes an array of integrated lateral imaging elements, and another insertable imaging device that includes an array of imaging elements that are oriented for forward-looking (end-fire) imaging.

Figure 39:
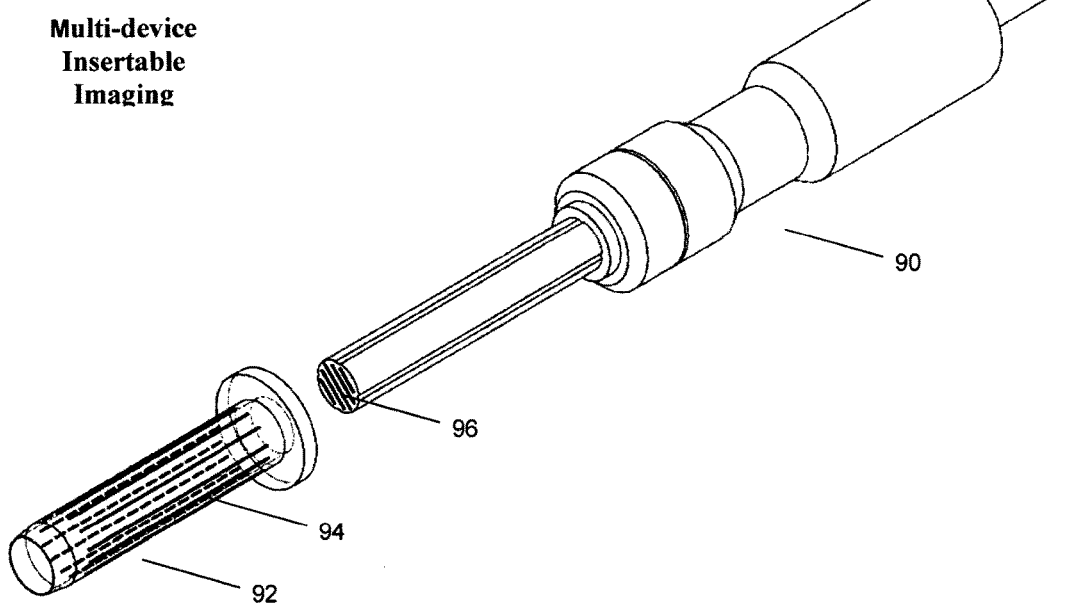
FIG. 39 illustrates an example implementation of a multi-device insertable imaging probe.

An example of such an embodiment is shown in FIG. 39, which illustrates an insertable imaging apparatus including an access port 92 with an array of laterally oriented MR coil elements 94, and an insertable MR imaging probe 90 having one or more forward-looking (end-fire) MR coil elements 96. In a cylindrical coordinate system, the insertable MR imaging probe is employed to perform imaging in the 'z' direction, while the access port with integrated imaging elements is employed to perform imaging in the 'θ' and 'r' directions.

Some imaging elements may be contained in the outer access sheath, however most of the body of the imaging device will contain the imaging receivers and probes. By placing the imaging devices in close proximately to the surgical volume, a very high signal to noise ratio can be obtained for all modalities.

It will be understood that a wide range of combinations of insertable MR imaging devices (probes, access ports, and imaging sleeves) may be employed without departing from the intended scope of the present disclosure. Many such combinations are described in Sections 1.5.1-1.5.5.

2.9 Example of Tested MR Imaging Probe Using Stripline Geometry

Figure 40:
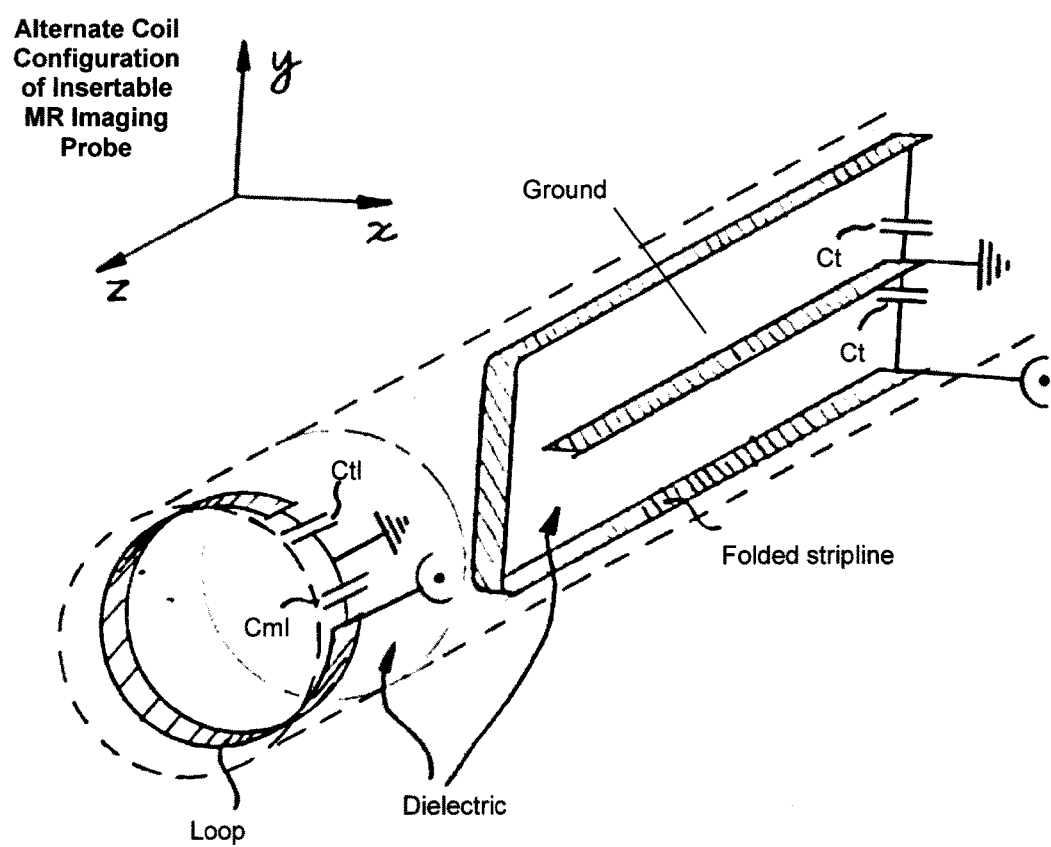
FIG. 40 illustrates an alternative coil configuration employed in another experimental implementation of an insertable MR imaging device, in which stripline and loop geometries were included.

The present section describes an example implementation of a stripline-based MR imaging probe that was fabricated and tested. The coil configuration is shown in FIG. 40. It consists of a folded stripline geometry with a distal loop, constructed from 4 mm wide copper tape that was adhered to the perimeter of a cannula. This stripline is 75 mm long and is shown paired with its ground-plane, in a coplanar formation that also extends the length of the cannula and encircles the tip. The stripline is formed from copper tape, which has a 'plane'. This is the same orientation of the ground. Circuit components were located at the proximal end. The coil is sensitive to the left, right, up, down, as well as forward. It is not sensitive backward. In this figure, capacitors Cml and Ctl is used to tune a loop coil, capacitors Ct are used to tune a folded stripline coil. Not shown are preamplifiers, blocking diodes, or other circuitry used.

This stripline was matched and tuned using non-magnetic capacitors and pin diodes were included in the circuit to provide blocking during the transmission portion of the MR scan. Foam tape was used to isolate the stripline from the ground plane in the areas where they crossover. The folded stripline coil was sensitive to fields in the 'x' direction and the loop coil was sensitive to fields in the 'z' direction.

Figure 41:
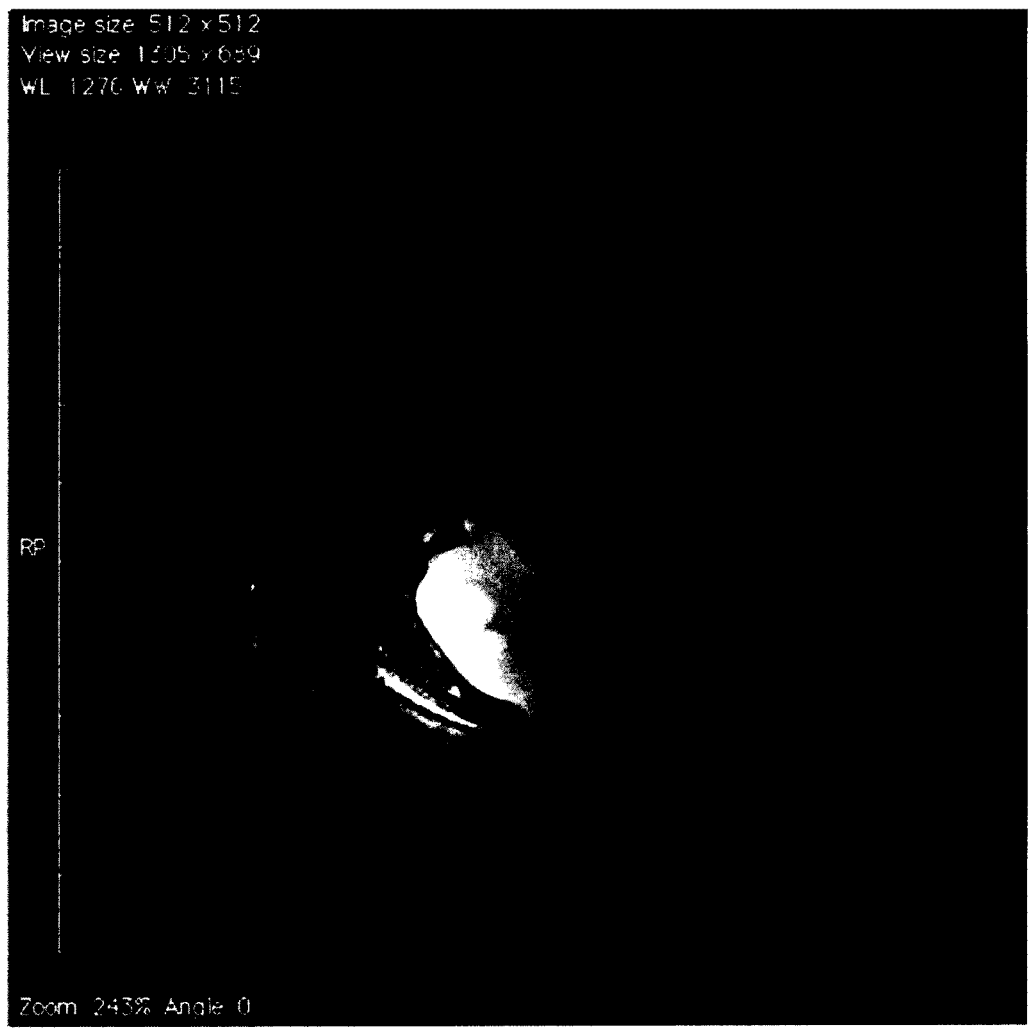
FIG. 41 shows an image of a sheep's brain acquired with an MR imaging probe having the coil configuration shown in FIG. 40.

FIG. 41 shows an image of a sheep brain acquired with this MR imaging probe at 1.5 T with a resolution of 0.5 mm by 0.5 mm by 2 mm.

Figure 42:
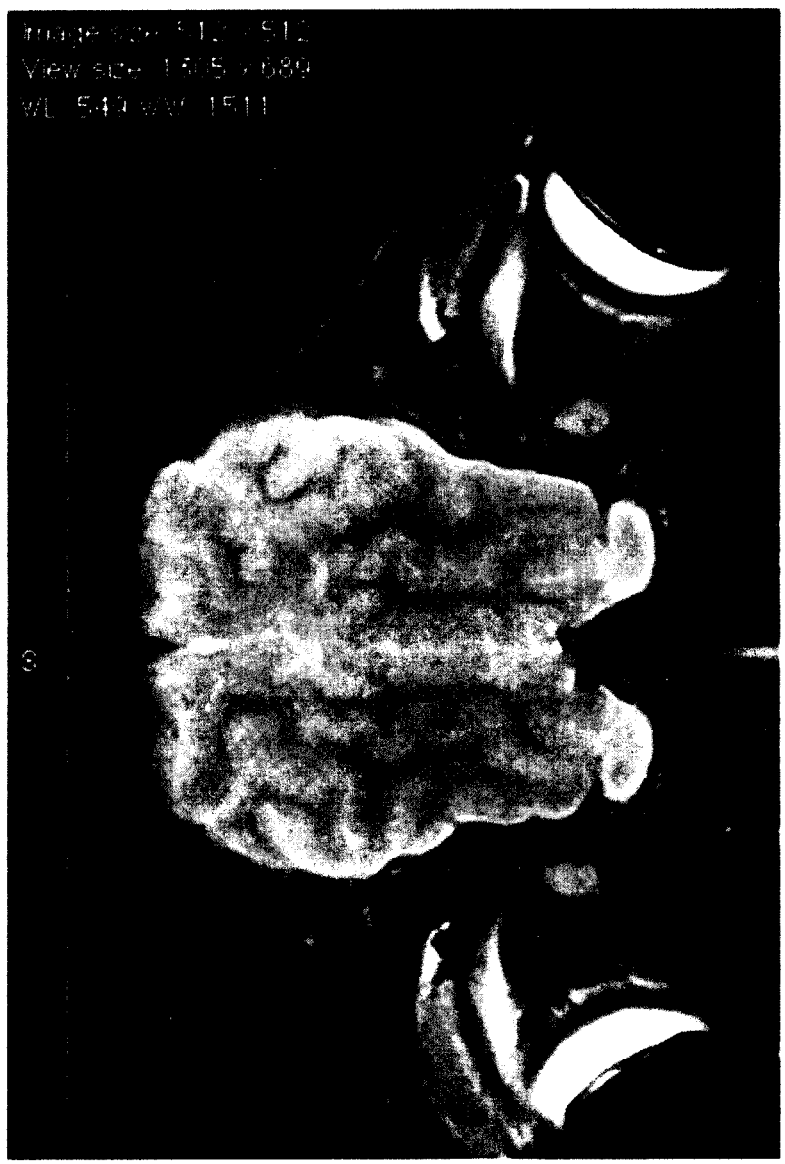
FIG. 42 shows an image of the same sheep brain acquired with the same resolution using a 32 channel head coil at 3.

FIG. 42 shows an image of the same sheep brain acquired with the same resolution using a 32 channel head coil at 3T. A comparison of the images emphasizes the clarity achieved at 1.5 T with this port coil embodiment as compared with the noisy 3 T version.

An alternative example implementation of the MR imaging probe as then fabricated, having coil geometry as depicted in FIG. 40. It included a folded stripline coil in conjunction with a loop coil. The loop coil had a diameter of 10 mm and was positioned at the tip of the MR imaging probe in order to complement the end-fire stripline element, which also intrinsically decouples the elements. The coils were spatially positioned such that they were intrinsically decoupled.

The loop was formed with 14 gauge silver-coated copper wire and was electrically isolated from the stripline by a foam dielectric substrate. The 50 mm long stripline was formed with adhesive Copper tape wrapped around a foam substrate. Both the stripline and stripline ground plane had a width of 10 mm. Non-magnetic capacitors were used to tune and match both coil elements. This combination of a stripline and a loop provided a 360° view of the tissue surrounding the port with a focus on the end-fire direction.

Figure 43:
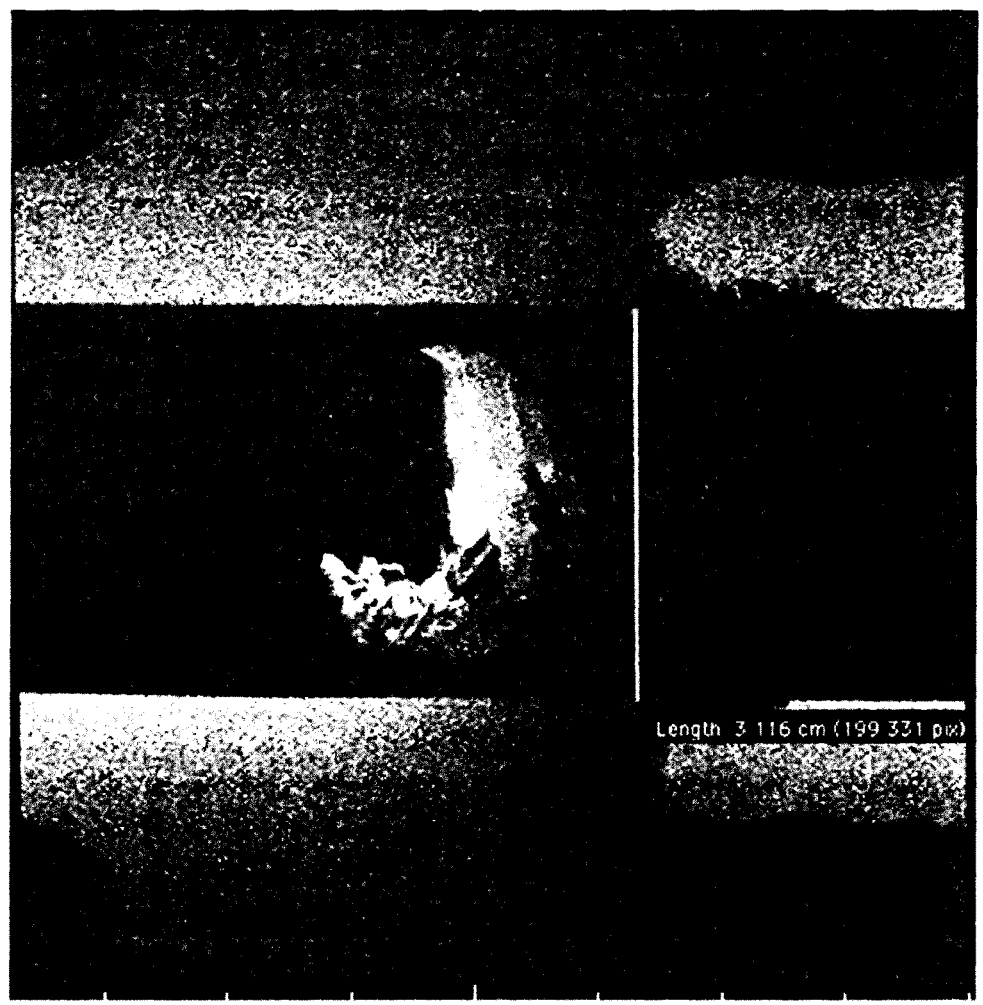
FIG. 43 shows an image acquired with the example MR imaging probe based on the coil design shown in FIG. 40.
Figure 44:
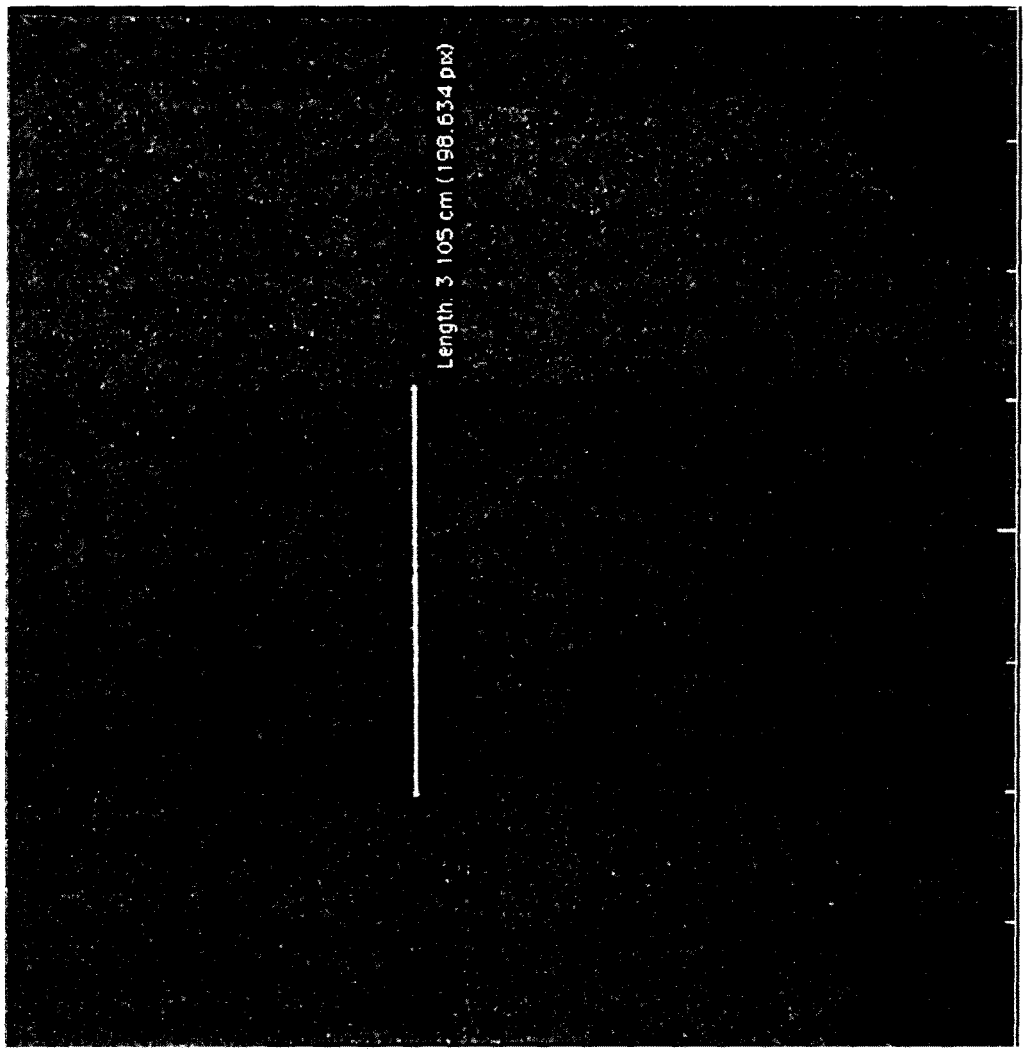
FIG. 44 shows the identical object imaged with a 32 channel head coil.

FIG. 43 and FIG. 44 show a high-resolution image of an approximately 2.5 cm by 3 cm broccoli floret acquired with the MR imaging probe embodiment described here and the equivalent image taken with a 32 channel head coil on a 3T MRI scanner with identical pulse sequences, respectively. The broccoli was located at the tip of the port coil to highlight the strong end-fire performance. As shown, the broccoli detail is quite intricate when imaged with the port coil yet imperceptible with the head coil. This clearly demonstrates the superior image quality attainable with the MR Imaging Probe.

2.10 Smart Coils

In some embodiments, coil arrays may be employed as smart coils, where the coils are dynamically (adaptively) controlled, such that only a portion of the coil elements of the array are activated or interrogated during scanning. It will be understood that the present "smart coil" embodiment pertain to any insertable MR imaging device having an array of coils, including insertable MR imaging probes, access ports with integrated coil arrays, imaging sleeves with integrated coil arrays, or combinations thereof, as described above.

In one example implementation, this may be achieved by an MR system that is configured to sample signals the elements of the coil array and to determine when a pre-selected signal level threshold has been achieved for each coil. When the threshold has been achieved for given coil, the coil are employed (e.g. activated or interrogated) for scanning. This arrangement allows an insertable MR imaging device to contain coils that are not necessarily orthogonal to the main magnetic field of the scanner.

Figure 46:
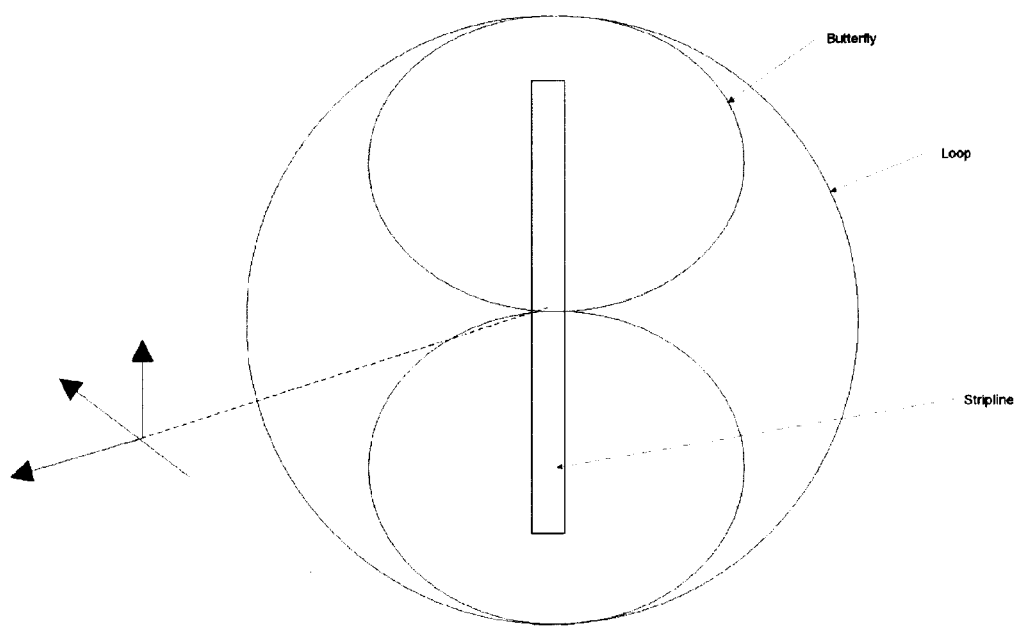
FIG. 46 illustrates an example insertable MR imaging probe containing an array of MR coils, where only a subset of coils are employed for scanning, based on comparing the coil signals to pre-selected criteria.

FIG. 46 illustrates an example implementation of a smart coil system, showing an insertable MR imaging probe having an array of coil. This coil arrangement consists of a butterfly, loop, and stripline element, which in combination excite fields in the x, y, and z direction. When this coil is inserted into an access port, and into the MR Field, a prescan may be conducted with the MRI system. The coils are sensitive to $B_1$ fields that are perpendicular to the main magnetic field $B_0$ will receive a stronger signal than those with a parallel $B_1$ field.

These signal values are then employed to determine which coil elements will be activated and which ones will remain off (or, which ones will be employed for constructing an image, and which will not).

In one example implementation, a criterion for determining which coils to activate or interrogate employs a threshold value, wherein, coils receiving signal levels that are below a certain value will remain off (or will not be interrogated) during signal acquisition.

Figure 45:
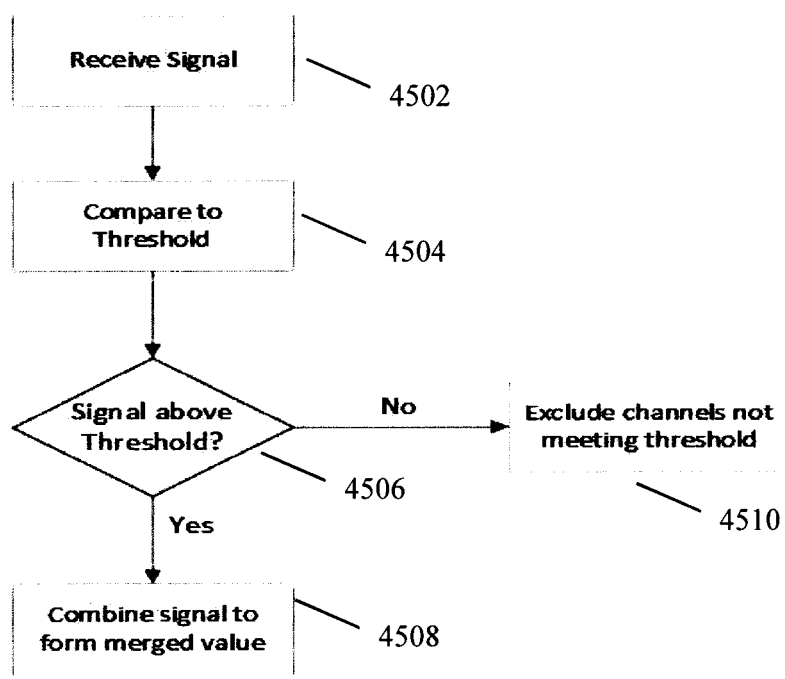
FIG. 45 is a flow chart illustrating an example method of selectively addressing selected coils within a coil array in order to achieve a smart coil array.

An example of one algorithm that would be employed by a controller/processor in order to determine which coils should be activated or interrogated is shown in the flow chart provided in FIG. 45. FIG. 45 is a flow chart illustrating an example method of selectively addressing selected coils within a coil array in order to achieve a smart coil array. Flow chart FIG. 45 begins with step 4502 where a data signal is received. The data signal (allocated through channels) is then compared to a threshold (step 4504). The threshold may include a predetermined noise level or known SNR (signal-to-noise ratio). Part of this comparison is to determine whether the signal is above the threshold (step 4506). If the result is not above the threshold, channels that do not meet this threshold are excluded (step 4510). If the channels do meet the threshold, then they are combined with the signal to form a merged value or image (step 4508). An alternate method may include weighing the worse images lower, but still use it to combine in the final image where the weight can be based on the threshold.

In some example methods, the signals from all coils should be sampled again after initially having determined a subset of coils to use. For example, the sampling may occur at a fixed time interval. Alternatively, the sampling may be based on a detected change in the orientation of the insertable MR imaging device within the $B_0$ field, such as, a changed detected by a tracking system, or a change detected by an inertial sensor associated with the insertable MR imaging device, such as an accelerometer.

In some embodiments, the coils could be selectively activated or interrogated according to a number of criteria. For example, criteria may be based on the signal of one coil compared to some other statistical measure associated with the other coils, such as the average signal magnitude, or criteria based on the a measure of signal to noise ratio, as opposed to signal strength. In another example embodiment, the signals to include could also be based on the orientation of the probe, as detected by a tracking system. The tracking system could be optical, RF, or accelerometer based (not claiming the tracking system in this patent). There could be a sensor such as a Hall sensor that is sensitive to the orientation of the static magnetic field.

2.11 Insertable MR Imaging Devices with Embedded Heating Elements

In some embodiments, an insertable MR imaging device, having an array of MR coils integrated therein, may further contain an array of heating elements, where the heating elements may be interspersed with coil array elements in order to generate thermal gradients during the imaging process. The heating and imaging cycles can be alternated to avoid interference between MR imaging elements and heating elements.

2.12 MR Imaging Probe with Magnet

Although the preceding insertable MR imaging embodiments have pertained to devices that employ the main magnet of an MRI scanner to generate the $B_0$ field, some alternative embodiments may include a magnet within the insertable MR imaging device for providing the $B_0$ field. Such devices may therefore be used outside of a conventional MRI scanner, since they are capable of generating their own $B_0$ field.

Figure 47A:
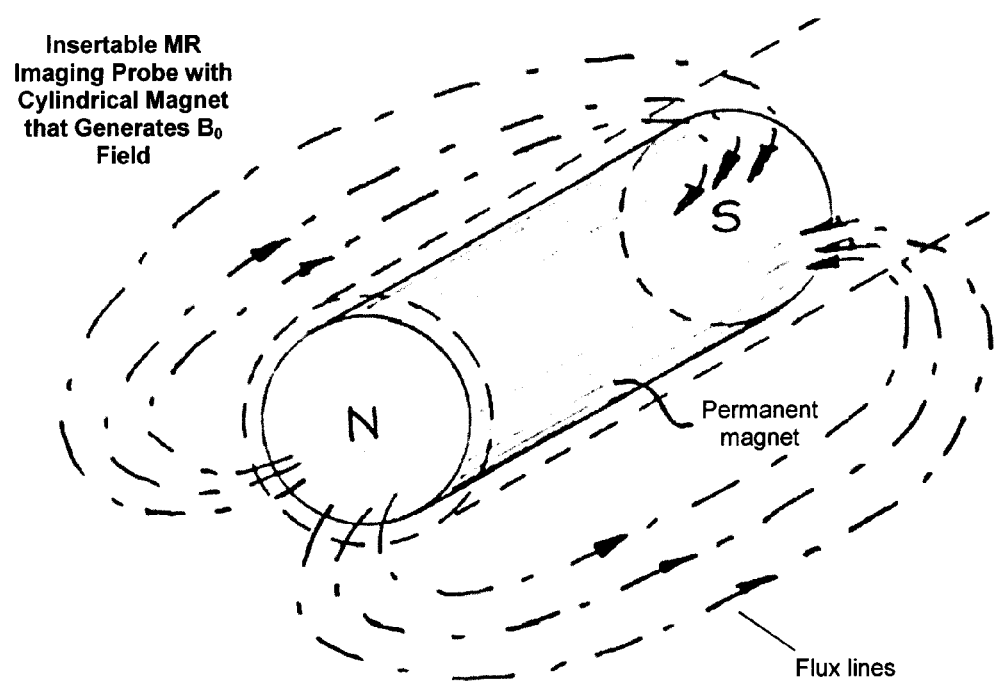
FIG. 47A illustrates an example implementation of an insertable MR imaging probe containing a cylindrical magnet that generates the $B_0$ field.

An example implementation of such embodiment is shown in FIG. 47A, which shows an insertable MR imaging probe containing a magnet within its body portion for generating the $B_0$ field. The magnet could be, for example, a cylindrical permanent magnet or electro-magnet, or, for example, a spherical permanent magnet or electro-magnet. In some embodiments, the magnet may be capable of producing different magnetic field strengths. In one example implementation, the magnetic field of a permanent magnet employed may be at least 0.5 Tesla.

In such a configuration, one can consider the conventional three Cartesian axes of an MRI system instead as axes of a cylindrical or spherical coordinate system, depending on the geometry of the $B_0$ magnet. For the cylindrical system, the Cartesian x,y,z axes could be replaced with cylindrical axes r, θ, and z. The main $B_0$ field would be in the z direction, decreasing with $1/r^2$ in the r direction.

Figure 47B:
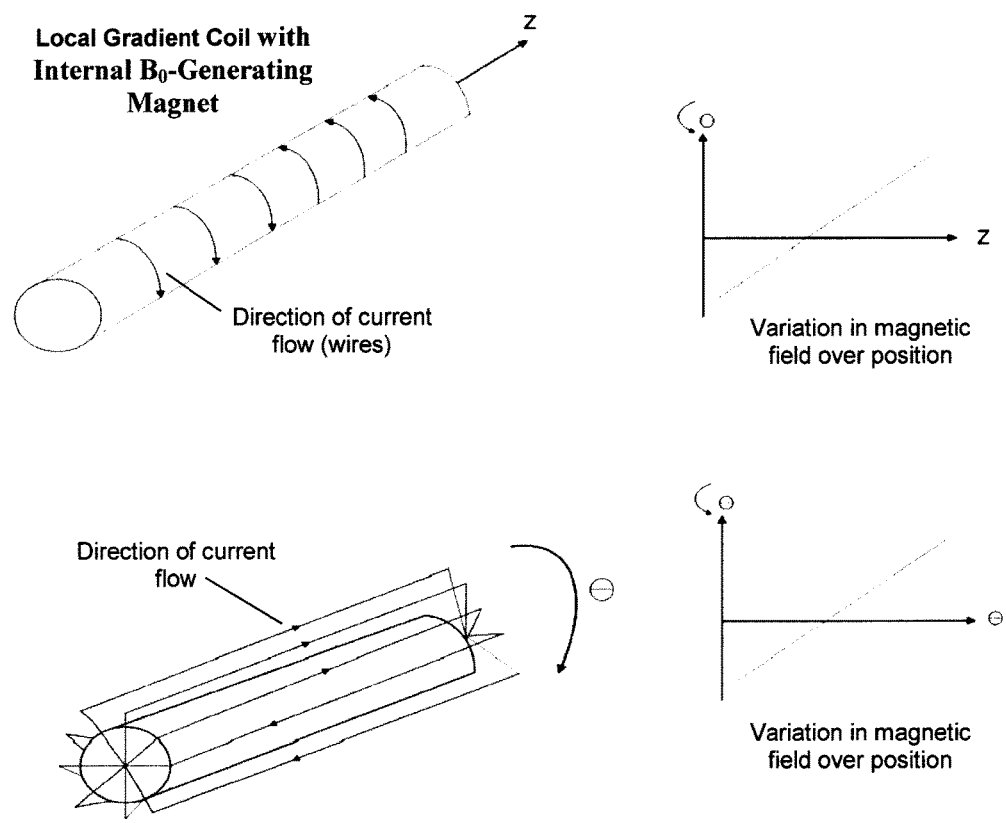
FIG. 47B illustrates the use of local gradient coils for producing a gradient field for an insertable MR imaging probe having an internal $B_0$-generating magnet.

As shown in FIG. 47A, the internal magnet produces an inhomogeneous magnetic field. There are several approaches to imaging within such an inhomogeneous field. One example implementation employs gradient coils to generate spatial encoding in the θ and z directions, as shown in FIG. 47B, and extrapolate from the non-uniform $B_0$ for the r gradient. The array of coils in FIG. 47B are used in this example as a transmit/receive coil.

The outside of the permanent magnet is typically coated in a non-conductive coating. Therefore, the gradient wiring may be wound directly against the permanent magnet itself. Alternately, a spacer could be placed between the permanent magnet and the gradient coils. The gradient coils are used to generate spatially varying magnetic fields in directions orthogonal to the static magnetic field. In this case, one set of gradient coils generates a field in phi (angle, around the probe), and the other generates a field in z (along the probe). Each set of gradient coils would require an independent gradient amplifier. The final gradient, r, radially away from the permanent magnet, is achieved through the natural drop-off in magnetic field strength of a permanent magnet. It should be noted that the gradients do not need to be perfectly linear, as long as they are known. Provided the spatial patterns of the gradient coils are well plotted, a modern reconstruction engine can undo any warping that occurs.

In order to reconstruct an image using a permanent magnet, the field of the permanent magnet, as well as the fields generated by the gradient coils would need to be accurately known. This could be generated through measurement, or through simulation. The method to reconstruct the image is the same as is currently used on modern MRI scanners. As long as the permanent magnet field is precisely known, there would not be a need to shim the magnet.

Figure 48A:
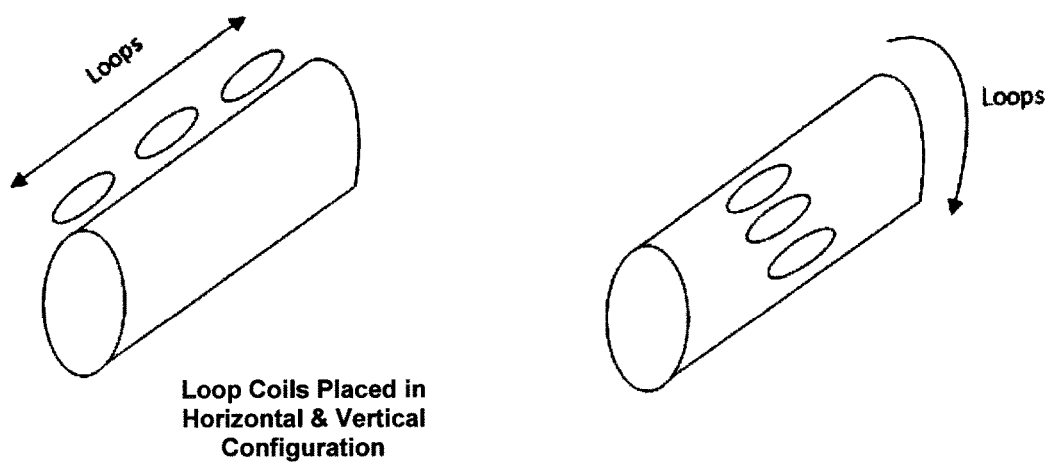
FIGS. 48A-C illustrate an example coil configuration for an insertable MR imaging probe having an internal $B_0$-generating magnet, where coil elements are arranged such that their imaging area can be used to determine spatial encoding in the θ and z directions.
Figure 48B:
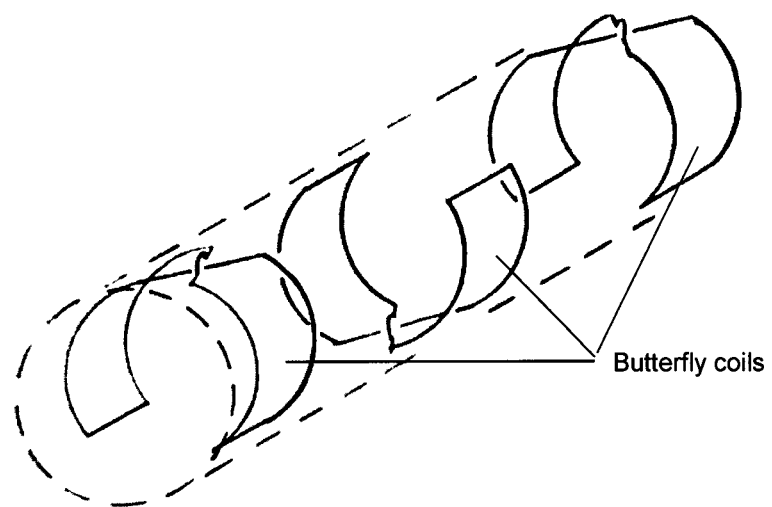
Figure 48C:
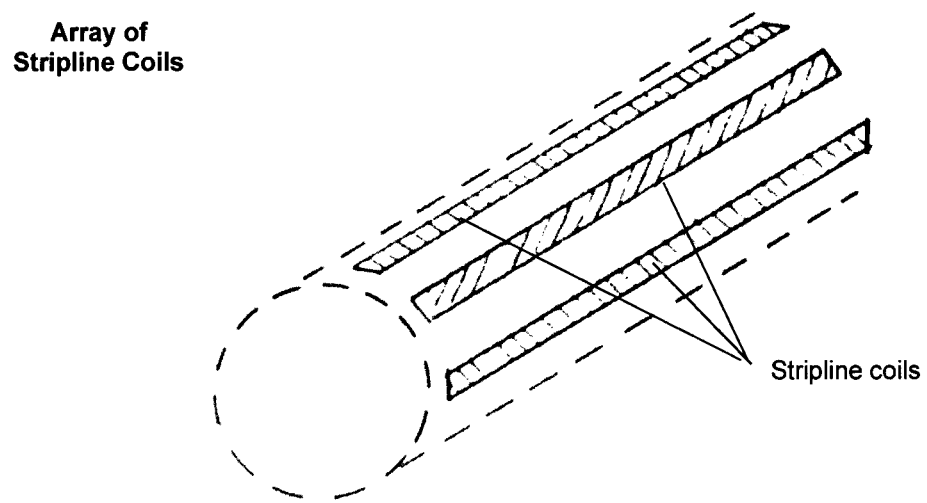

Another example option is to use a plurality of very coil elements (such that there size approaches the desired resolution) such that their imaging area can be used to determine spatial encoding in the θ and z directions while continuing to extrapolate from the non-uniform $B_0$ field for the r gradient. Three example implementations of this design are shown in FIG. 48A-C. FIG. 48A depicts an array of loop coils where the loops coils can be placed in a horizontal and a vertical configuration. FIG. 48B depicts a butterfly coil wrapping the perimeter, and finally FIG. 48C shows an array of striplines. These all serve to create a $B_1$ field orthogonal to the magnet generated $B_0$ field, and to receive an MR signal in the same orientation. Many combinations of these elements exist to enable a full volume imaging area surrounding the coil with a focused end-fire imaging area. In FIG. 48C, the stripline coils are used in combination with the magnet of FIG. 47A, and the gradients of FIG. 47B.

Another example embodiment may employ a plurality of very small coil elements and physically move the coil in the θ and z directions, and use the change in signal over time to serve as the gradients for these directions.

In a further embodiment, no physical gradients are used. Instead, the motion of a transmit/receive coil is used to artificially generate the situation of a magnetic field varying in space. By arranging a set of transmit/receive coils around a probe, the motion required to successfully approximate physical gradients would be rotating motion, as well as motion in the 'z' direction, along the axis of the probe. Signal acquisition would take place at the same time as the probe motion. This embodiment uses the same magnet configuration as FIG. 47A.

This spatial information can be captured with a navigation system and relayed to the MR system. Again, the non-uniform $B_0$ field is used for the r gradient. The physical movement of the coil can be achieved by moving the arm that is otherwise used to rigidly hold the coil in place. Consistent movement of the arm can be realized through automation of the arm to achieve consistent and constant movement along specific directions. Alternatively, the movement of the coil may be achieved by retracting the coil into the handle in a consistent manner while the handle is held rigidly in place by an external mechanical arm.

Figure 49:
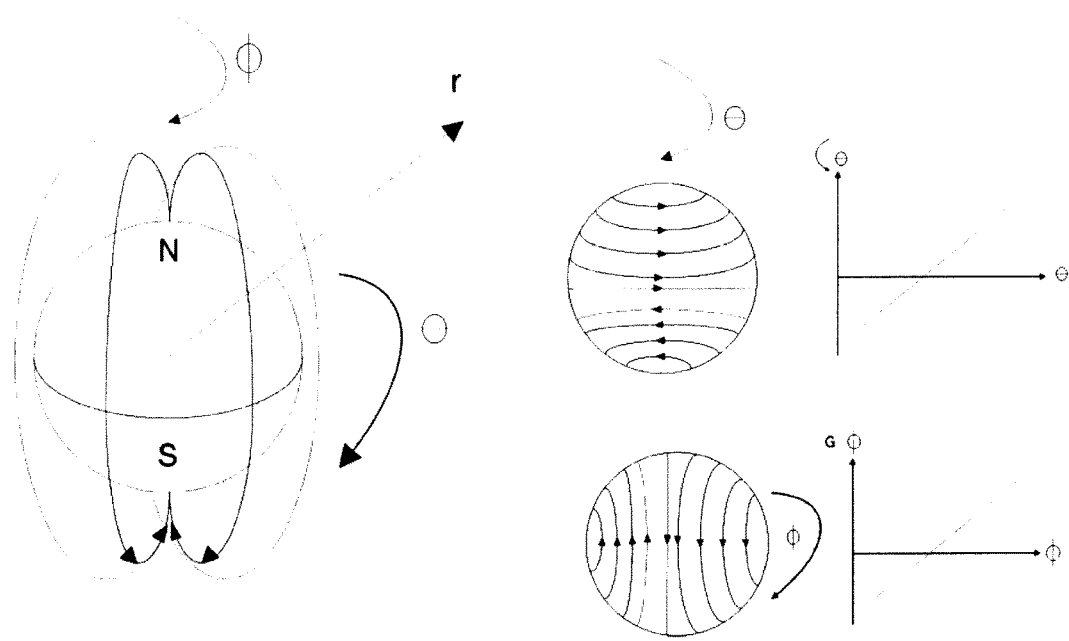
FIG. 49 illustrates an example implementation of an insertable MR imaging probe containing a spherical magnet that generates the $B_0$ field.

As noted above, in another example implementation, the magnet may be a spherically shaped magnet. The following three example implementations may be employed in such as case. The first embodiment employs gradient coils to generate spatial encoding in the θ and ϕ directions, and extrapolates from the non-uniform $B_0$ for the r gradient, as shown in FIG. 49.

It is noted that each gradient will require a separate gradient amplifier. The outside of permanent magnet is typically coated in a non-conductive coating. Therefore, the gradient wiring may be wound directly against the permanent magnet itself. Alternately, a spacer could be placed between the permanent magnet and the gradient coils. The gradient coils are used to generate spatially varying magnetic fields in directions orthogonal to the static magnetic field. In this case, one set of gradient coils generates a field in phi (angle, around the probe), and the other generates a field in theta (other angle around the magnet). The final gradient, r, radially away from the permanent magnet, is achieved through the natural drop-off in magnetic field strength of a permanent magnet. It should be noted that the gradients do not need to be perfectly linear, as long as they are known. Provided the spatial patterns of the gradient coils are well plotted, a modern reconstruction engine can undo any warping that occurs.

Another example implementation involves the use of a plurality of very small coil elements such that their imaging area can be used to determine spatial encoding in the θ and ϕ directions while continuing to extrapolate from the non-uniform $B_0$ field for the r gradient.

In another embodiment, a plurality of very small coil elements may be used in conjunction with physically moving the coil in the θ and ϕ directions, and use the change in signal over time to serve as the gradients for these directions. Once again, the non-uniform $B_0$ field is used for the r gradient.

The coil array surrounding the magnet may be selected from the elements described within to generate and receive orthogonal $B_1$ fields. The designs may be used either with or without externally applied gradients as noted. In the latter scenario, the combination of the magnetic field pattern, $B_0$, and the sensitivity profile of each element in the array may be used be to decode the spatial information in combination with the coil's physical position in space. As such, the port coil's movements may be tracked to provide z, and θ (or θ and ϕ for a spherical system) data and the radial information can be extrapolated from the non-uniform $B_0$ field.

2.13 Housing Material/Cannula Having a Susceptibility Map

Magnetic susceptibility is a measure of how a material reacts to a magnetic field. It is given by the equation $M=\chi H$ where M is the magnetization and H is magnetic field. Susceptibility ($\chi$) is related to magnetic permeability by the equation $\chi=\mu_r-1$. Although there is only a small susceptibility difference between Air (0.36E-6) and Water (-9.05E-6), this is enough to distort MR images, particularly diffusion weighted imaging (DWI) and the related diffusion tensor imaging (DTI). This distortion is particularly seen at the front of the brain, where the air of the sinuses causes a susceptibility difference in this area.

Typically, susceptibility induced distortions are ignored in MR, as they do not impact a radiologist's ability to read the scan. However, in an intraoperative setting, geometric accuracy can be of the utmost importance. Indeed, if an insertable MR imaging device is inserted into an access port, as described above, even if the insertable MR imaging device is formed from a non-magnetic material, the ability to perform geometrically accurate diffusion scans will be compromised if the insertable MR imaging device does not have a close susceptibility match to the brain.

Therefore, in some embodiments, insertable MR imaging devices are formed, at least in part, from a material having a susceptibility that is similar to that of the tissues being imaged (e.g. the tissues that reside adjacent to the insertable MR imaging device when it is inserted). A susceptibility that is similar to that of tissues is a susceptibility that differs from that of the tissue being imaged by approximately (−9.05E-6) which is similar to the range for water.

Examples of materials with a close susceptibility map to water (soft tissue in the body), which could be employed to fabricate an insertable MR imaging device, include nylon, silicon nitride, Teflon®, polysulfone, magnesia, steatitie, carbon fiber composites, Vespel® (acetal), zirconia, plexiglass, PEEK, wood and copper. In the class of carbon fiber composites, one other material is pyrolytic graphite foam (PG Foam, described in 'Pyrolytic Graphite Foam: A Passive Magnetic Susceptibility Matching Material' by Lee et al, Journal of Magnetic Resonance Imaging 32:684-691 (2010)). Suitable materials for forming the shell of an insertable MR probe include polycarbonate, Teflon, and PEEK, and a suitable material for forming the dielectric portion within the body of an insertable MR probe is Teflon.

In one embodiment in which an access port is employed with one or more insertable MR imaging devices, such as an insertable MR imaging probe or an insertable imaging sleeve, the access port and the insertable MR imaging devices are formed, at least in part, from a common material that is susceptibility matched to the tissue being imaged.

Furthermore, as described in Section 1.1, the access port and an insertable MR imaging probe may be configured such that a close fit is achieved between the outer wall of the insertable imaging probe and the access port, thereby reducing the amount of air between the imaging probe and the access port. This avoids MR image distortion caused by differences in susceptibility between air, tissue, and the materials forming the access port and the insertable imaging probe.

It is noted that while large conductor sizes can cause eddy current problems in scanners, the size of the port in the embodiments considered herein is expected to be sufficiently small to avoid eddy current problems.

3. Ultrasound

The present section describes various embodiments employing one or more ultrasound (acoustic) transducers (ultrasound elements) for imaging within an access port, in order to achieve ultrasonic imaging within an internal area of interest.

As described above, some embodiments described in the present section may complement a minimally-invasive neurological procedures (such as surgical procedures) whereby a procedure involving internal brain tissue is conducted via a narrow corridor formed via an access port. For example, an insertable ultrasonic imaging device may be adapted to be received (e.g. slidable received, as described in Section 1 above) into the bore of an access port and exploit its close position to produce ultrasound images, such as ultrasound images of the surrounding (lateral) brain tissue and/or forward-looking (anterior, distal) tissues. Such images may be used during medical procedures (e.g. surgical procedures), potentially providing detail that would otherwise not be obtainable with current technologies (or would otherwise be obtainable with less resolution or signal to noise, using currently available technologies).

The ultrasound transducers may be provided within an insertable imaging device according to a number of different configurations. For example, in one example implementation, a single ultrasonic transducer may be employed (including a single ultrasonic transducer with multiple electrical connections to act as a phased array). In another example embodiment, an array of ultrasonic transducers may be provided within an insertable imaging device, such as a radial array spanning a radial segment of the insertable ultrasonic imaging device, or as an array of transducers with an opening at the center to enable access to distal tissue through an internal bore.

The ultrasonic elements of an ultrasound array may be realized using known technologies such as piezoelectric transducers. It will be understood, however, that other solid-state transducers may alternative replace the piezoelectric transducers.

In some embodiments, an array of ultrasound transducers may be arranged as a phased array to generate beams that may be swept in predetermined fashion. This can be realized using a transducer driver circuit that implements necessary signal processing capability.

An array of ultrasonic transducers may be arranged sparsely so that the tissue region beyond the distal end of the insertable ultrasonic imaging device may be clearly visible for visual inspection or for simultaneous imaging through the use of an additional imaging device, such as an external videoscope. The array of transducers may be sparsely arranged without compromising the ability to acquire a complete ultrasonic volume image by appropriately overlapping the fields of adjacent transducers. Transducer configurations may be realized, for example as described in "Design Optimization for a 2D Sparse Transducer Array for 3D Ultrasound Imaging", Proc IEEE Ultrasound Symposium, 2010 Oct. 11; 2010:1928-1931.

Insertable ultrasonic imaging devices according to the embodiments described here may be, for example, an insertable ultrasonic imaging probe, an insertable ultrasonic imaging introducer for inserting an access port, an access port with one or more integrated ultrasonic transducers, one or more ultrasonic imaging sleeves that are configured to be coaxially inserted into an access port, or various combinations of these insertable imaging devices, as illustrated in Section 1. Various example implementations of such insertable ultrasonic imaging devices, and various ultrasonic transducer configurations, are described in detail below.

The ultrasonic transducer configurations presented below are provided as example and non-limiting implementations of potential configurations. Some of the following embodiments provide configurations that produce a forward-looking focused receiving or transmitting zone. In other words, some of the following embodiments provide transducer configurations that are sensitive to regions anterior to the longitudinal probe body (regions beyond the distal end of the probe body), e.g. in an end-fired configuration beyond the distal region of the body of the imaging probe. Such embodiments may be included or incorporated within the various imaging probes described within this disclosure.

3.1.1 Insertable Ultrasonic Imaging Probes

Figure 50A:
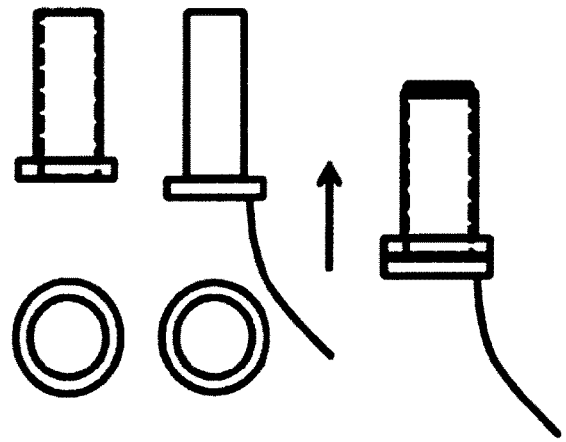
FIGS. 50A-C illustrate three example implementations of an insertable ultrasonic imaging probe having one or more distal ultrasonic transducers for imaging tissues in a forward-looking direction within an access port.
Figure 50B:
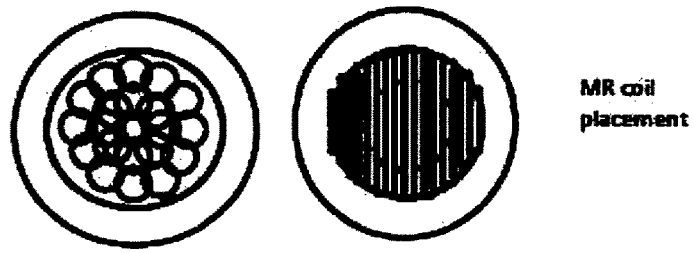
Figure 50C:
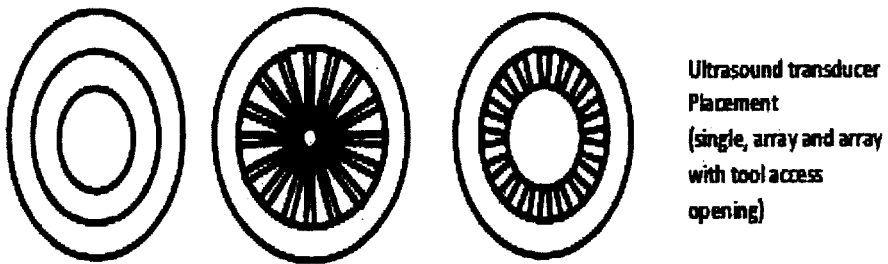

FIGS. 50A-C illustrate three example implementations of an insertable ultrasonic imaging probe having one or more distal ultrasonic transducers for imaging tissues in a forward-looking direction within an access port. FIG. 50A shows an embodiment with a single circular transducer 5010. This configuration supports the insertion of a second imaging probe through the central opening 5015. FIG. 50B shows an embodiment having a circularly-arranged ultrasonic array with MR transducer elements located in the opening. FIG. 50C shows an embodiment having a radial array of transducer elements, with an opening in the middle. The opening in the middle allows access for surgical tools, or light for multi-modality imaging. The imaging device may be a local ultrasound receiver and transmitter, or a local ultrasound receiver used in conjunction with an external ultrasound transmitter, or an internal ultrasound transmitter used in conjunction with an external ultrasound receiver.

Figure 64:
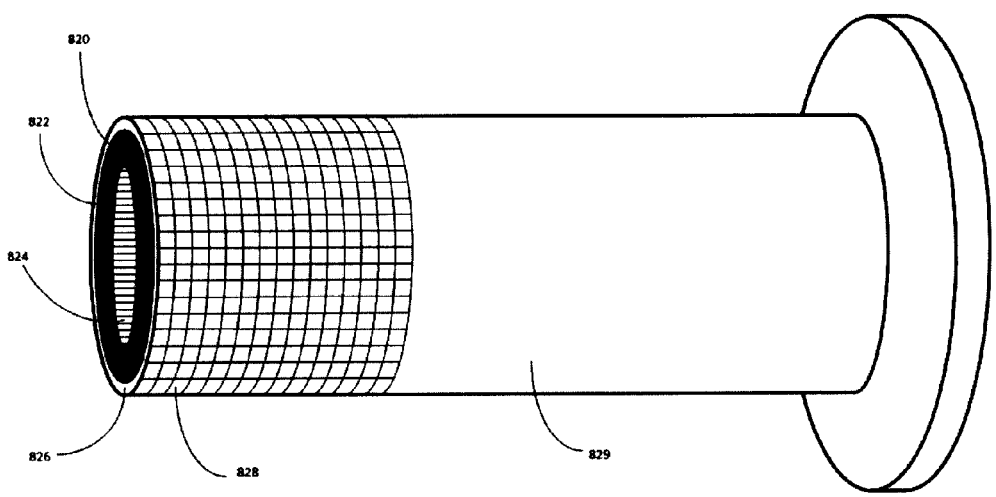
FIG. 64 is an exemplary embodiment of an ultrasound imaging assembly.

In an example embodiment as described herein, an ultrasonic transducer array can be oriented around the peripheral of the port in an annular orientation for ultrasound imaging of the area surrounding the port. FIG. 64 depicts such an ultrasound imaging assembly. In the figure, an ultrasound transducer array 6428 is oriented around a port 6429. It should be noted that the array 6428 can be of various types, including but not limited to, a flat phased array, a curved array, a phased sector array, a linear array, a multi-row array, and other 1D and 2D arrays. The ultrasound imaging assembly also consists of a backing layer 6420 to dampen and consequently shorten pulse duration. In addition an electrical connection layer 6422 creates a communication pathway between the array and an ultrasound control system (not shown).

Wiring from the electrical connection layer provides the electrical connection to the ultrasound control system not located in or on the port. Non limiting examples of this wiring may pass through the walls of the port through a conduit, or can be oriented on the inner or outer sides of the port, as well as be used in conjunction with a PCB or flexible PCB, etc. It should be noted that the wiring refers to any mechanism to transfer the electrical signals or information they carry generated by the ultrasound signals from the array to the ultrasound control system where it may be collected and analyzed.

Figure 51:
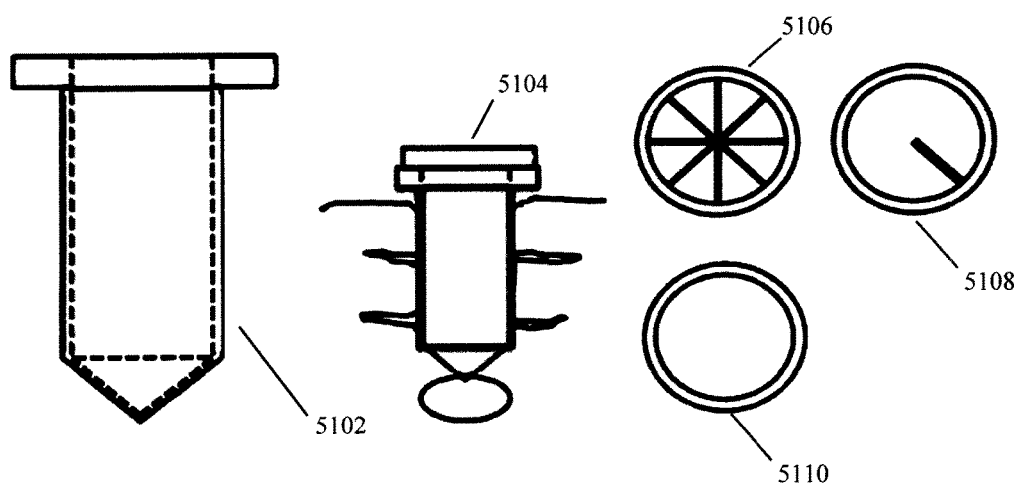
FIG. 51 illustrates an example implementation of an insertable ultrasonic imaging probe having an ultrasonic transducer integrated therein.

FIG. 51 illustrates an example implementation of an insertable ultrasonic imaging probe having an ultrasonic transducer integrated therein. In FIG. 51 a single ultrasonic transducer 5108 may be integrated within the probe body and a 3D ultrasonic image-based visualization of the tissues surrounding an access port, into which the insertable ultrasonic imaging probe is inserted, can be realized by mechanically (manually or robotically) rotating the insertable ultrasonic imaging probe during its insertion and/or withdrawal, and reconstructing the volume image through the use of standard software reconstruction methodologies. In FIG. 51, introducer 5104 and port 5102 when combined can produce insert imaging arrays in different configurations, including arrays that are swept along distal and sides of the port. Port insert with surface imaging array are shown as three pieces as elements 5106, 5108 and 5110 respectively. The radial arrangement of transducer arrays along the atraumatic tip of the imaging probe 5104 enable the acquisition of ultrasonic image of the distal end of the port during insertion of the port towards a tumor 5112. The transducer arrays (such as the one illustrated in 5106) can be used as transmitters and receivers by allocating some transducers as transmitters and others as receivers. This is known as spatial multiplexing of the transducer elements. In another embodiment, the transducers may be multiplexed in time as transmitters and receivers. In all of the configurations, the transducers may be energized using standard ultrasonic driver circuit such as that described in U.S. Pat. No. 5,590,658.

Figure 52:
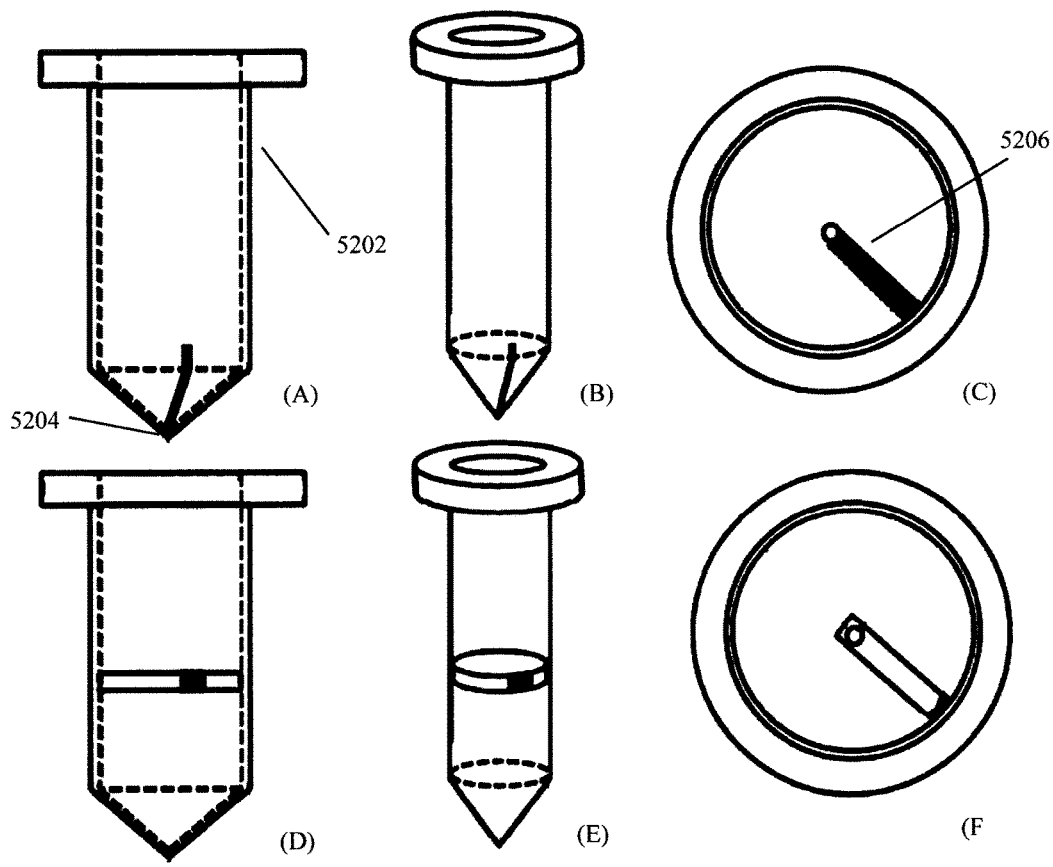
FIGS. 52A-F illustrate example implementations of an insertable ultrasonic imaging introducer having of a single radial array of ultrasound transducers positioned such that optical view through the introducer tip is not occluded.

FIGS. 52A-F illustrate example implementations of an insertable ultrasonic imaging introducer having of a single radial array of ultrasound transducers positioned such that optical view through the introducer tip is not occluded. The top row shows introducer 5202 with an opening to the distal tip 5204 of the insert in a side view in FIG. 52A and a perspective view in FIG. 52B. In FIG. 52C introducer 5202 is shown with a multimodality line scan array 5206. The multimodality line scan array 5206 may be composed of a combination of ultrasound element and fiber bundles placed adjacent to each other. While the ultrasound array may be used for ultrasonic imaging, the fiber bundle may be used for spectroscopic analysis such as Raman Spectroscopy or the fiber bundle may be used to deliver pulsed laser to the tissue layer and the generated photo-acoustic waves are measured by the ultrasound transducer. The bottom row of this figure (FIGS. 52D, 52E and 52F) shows a similar embodiment, without the angulated imaging array at the bottom.

The example embodiment shown in FIG. 51A-C may be further refined to provide an embodiment reducing the space within an access port, while providing sufficient space for including transducer arrays at the tip of the introducer. An example implementation of such an embodiment is shown in FIGS. 53A-C As shown in these figures, the insertable ultrasonic introducer 5315 includes an array of ultrasonic transducers, optionally orientated an oblique angle 5320 directed towards the tissue, providing an opening 5310 through which light may be delivered, or access for intervention. In this manner the device can be employed for imaging as it is inserted, or imaging can be performed while the port is moved to different areas within the body (e.g. the brain). In the example embodiment shown, the centre (5210) is open, while the sides, housing the ultrasonic array, are employed for imaging. In this manner, the insertable ultrasonic introducer can be inserted into the subject with transducer elements covering the field with an angled side viewing array, and optionally with forward-looking imaging provided by an additional insertable ultrasonic imaging probe that is insertable into the central bore of the introducer. The opening may be used to insert a probe with another imaging modality, such as MR strip coils (FIG. 53C). Hence, two imaging modalities may be combined in the same cavity and one imaging modality may be optionally removed to make space for surgical resection or tissue access.

Figure 54:
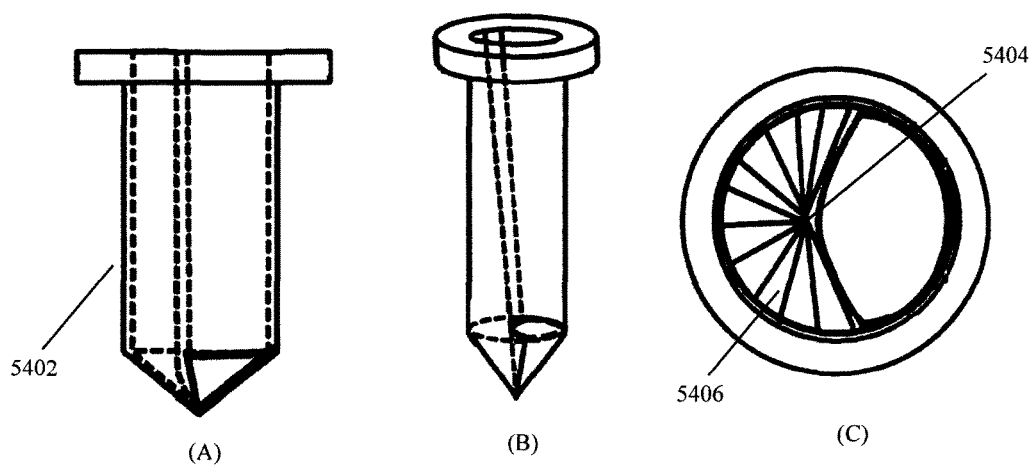
FIGS. 54A-C illustrate another example implementation of an insertable ultrasonic imaging probe having an ultrasonic transducer integrated therein, where the introducer includes an opening and a non-conical tip.

In another example implementation, shown in FIG. 54A-C, the insertable ultrasonic introducer 5402 may include a non-conical tip 5404 as seen in FIG. 54C, where the tip 5404 is offset to one side of the axis of the introducer 5402. In this way, the innermost face of the tip 5404 can have an array of transducer elements 5406 that can be aimed towards the tissue that is accessible by the aperture, and the outermost elements can image the outside surface. In this way, the tissue can be imaged during tissue resection. This introducer could be positioned deeper into the surgical cavity as a means for the surgeon to explore the inner imaging volume concurrently with surgical resection.

3.1.2 Access Ports and Imaging Sleeves with Integrated Ultrasonic Transducers

The preceding embodiments of Section 3 have disclosed various example insertable ultrasonic imaging probes and introducers. However, it will be understood that in alternative embodiments, one or more ultrasonic transducers may be provided formed on or within (e.g. embedded or recessed within) an access port, or a sleeve that is insertable into an access port, as initially described in Sections 1.3 and 1.4.

In one embodiment, one or more ultrasonic transducers are formed on, or embedded within, an access port, thus providing a hollow imaging sleeve wherein instruments such as surgical tools can be inserted during a medical procedure. This provides an entry point for other imaging devices, image guided therapies, or contrast agent administration. This may include biopsy tools, deep brain stimulation devices, thermal imaging equipment, or ultrasound devices among others. Such embodiments are similar to the access ports with integrated MR coils, as disclosed in Section 2.6.

In other embodiments, an imaging sleeve with one or more integrated ultrasonic transducers may be provided, where the imaging sleeve is insertable into an access port, thereby providing a reconfigurable and optional means of port-based-imaging while still providing a central bore that provides access (direct or indirect) to internal tissues. This embodiment was introduced in Section 1.4, and is similar to the MR imaging sleeve embodiments disclosed in Section 2.6.

In one embodiment, one or more ultrasonic transducers are formed on, or embedded within, a sleeve that is slidably received within an access port, thus providing a hollow imaging sleeve wherein instruments such as surgical tools can be inserted during a medical procedure.

3.2 Embodiments with Combinations of Multiple Insertable Ultrasonic Imaging Devices Finally, it will be understood that, as described in Section 1.5 (and in Sections 1.5.1-1.5.5), additional embodiments may be provided by combining two or more of the above insertable ultrasonic imaging devices.

For example, in one example implementation, an insertable imaging apparatus may include one insertable imaging device that includes an access port having an array of integrated laterally directed ultrasonic transducer elements, and an insertable imaging probe having an array of ultrasonic transducer elements that are oriented for forward-looking (end-fire) imaging.

4. Conductive Sensors for Local Resistance Map

In another embodiment, an additional measurement modality can be realized through the inclusion, on an insertable imaging device configured to contact the tissue, of an array of electrical sensors for the generation of a local resistance map. This is achieved by sensing the conductivity between pairs of conductors where the tissue forms part of the electrical circuit. By sharing one of the conductors, a map may be generated by measuring conductivity between a shared conductor and an array of complementary conductors that are individually addressable. The resulting measurements may be then used to construct a vector indicating the physical orientation of least resistance.

Figure 55:
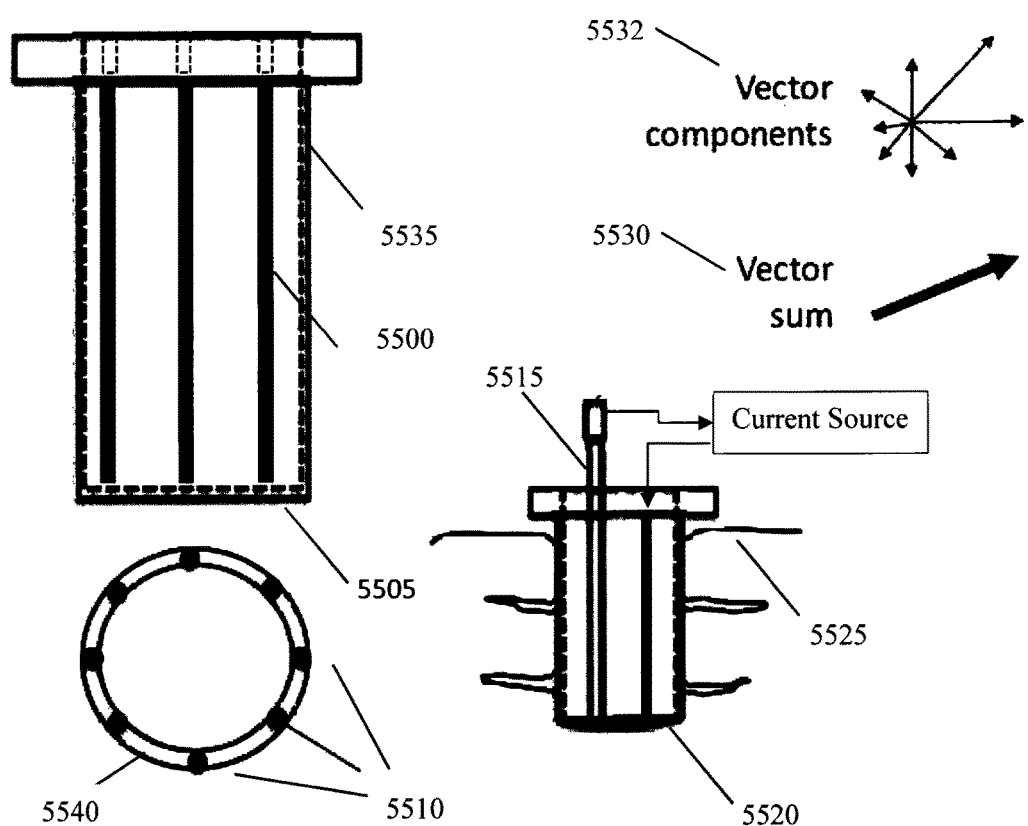
FIG. 55 illustrates an example implementation of an access port having an array of conductive elements on an outer surface thereof for performing a measurement of a resistance map.

For example, as shown in FIG. 55 an array of electrical conductors (cathodes or anodes, 5510 and 5500) may be placed along the circumference of an access port near its distal portion 5505 of the port 5535, where each conductor 5510 is individually addressable. FIG. 55 also shows the distal view of the port 5540 illustrating the arrangement of exposed contact points that form one polarity for measuring conductivity. A conductor of the opposite polarity may be presented through a needle or a modified surgical tool 5515. Electrical contact with exposed conductors 5510 is established via conductors 5500 embedded in the sleeve of the port. One polarity of an external current source is attached to these conductors at the proximal end of the port which will be outside of the tissue throughout the surgical procedure. Electrical connection between the current source and the conductors 5500 may be established, for example, using welded connection, spring-loaded connection or clamps. All these connection mechanism are commonly used in medical and laboratory equipment. The opposite polarity of the same current source is provided through a needle or modified surgical tool 5515. A surgical tool may be modified for this purpose by constructing a tool with non-conductive material and providing a conductive point only at the tip of the tool. Hence, electrical contact is established by the surgical tool only at a specific point at its tip. Such specific conductive contact may be placed at any predetermined position on the surgical tool.

The conductance or resistance measured from the needle tip 5515 to each of the array elements 5510 at the distal end of the port can be used to construct a vector map that can be used to infer arrangement of conductive tissue structures such as nerve bundles. Vector components 5532 and Vector sum 5530 illustrates inferring nerve bundle direction 5530 based on multiple vector component measurements 5532. The geometric location of each measurement electrode (5510) is known a priori since this is fixed by design.

Further, if the electrode located on the surgical tool (5515) is positioned at the centre of the port at the distal end, then relative orientation of current paths from the surgical tool's tip to each of the measurement electrodes (5510) is known. Since each measurement electrode (5510) is individually addressable, the corresponding conductance along that specific orientation can be measured. Hence, a vector can be used to represent the magnitude and direction of each of the measured conductance. The resulting vectors can be then added using standard vector addition methods to arrive at a single vector that represents the magnitude and direction of conductance in the region of the tissue that is in contact with the distal end of the port. The orientation of conductance vector will imply the physical orientation of conductive tissue (nerve bundles) that is in contact with the distal end of the port. The measurement can involve DC current or oscillating current. For example, oscillations in the range of 20 kHz to 100 MHz result in significant differences in dielectric properties of the tissue when the region under investigation is breast tissue (reference: "Dielectric properties of breast carcinoma and surrounding tissues", IEEE Trans. BME, Volume 35).

Such measurement may be also extended to discerning bioelectric differences, so that presence of sufficient healthy tissue margin can be confirmed after resecting tumor tissue. For example, bulk of tumor tissue may be resected first and then above described tool may be introduced in the open cavity left after resection to assess the electrical characteristic of the tissue surface. The conductance measurement can be used to assess if the residual tissue left after resecting bulk of the tumor still contains tumor tissue. This inference technique is described in detail in "A Review of Parameters for the Bioelectrical Characterization of Breast Tissue", Jacques Jossinet, Mchel Schmitt, Annals of the New York Academy of Sciences, April 1999.

In another embodiment, a series of real-time sensing electrode arrays may be located on the introducer, where the sensing arrays record physiologic information as the access port is introduced into the tissue, or is repositioned within the patient.

Figure 56:
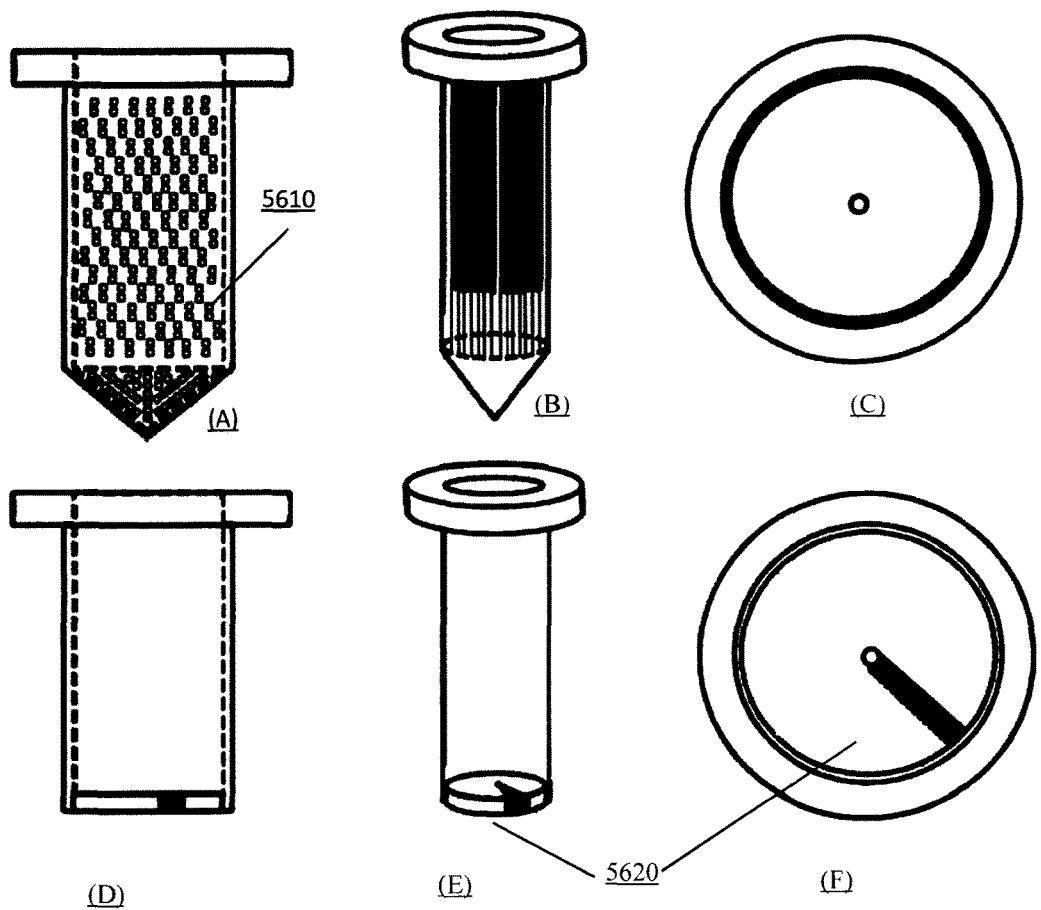
FIG. 56 illustrates an example implementation of an introducer having an array of sensing elements for making physiological measurements.

Example implementations of such an embodiment are shown in FIG. 56. FIGS. 56 (A) and (B) illustrate implementations where outside of the port is lined with sensor elements. Such sensor elements may be simple electrical contacts that are individually addressable (as described for FIG. 55). FIG. 56 (C) illustrates the arrangement of such sensors from top view of ports shown in (A) and (B). Such conformable sensors may be constructed from flexible organic transistors and circuits as described in "Flexible organic transistors and circuits with extreme bending stability," Sekitani et. al., Nature Materials, Vol. 9, December 2010. Another approach to embedding sensors on the walls of the introducer or the port may be as described in "A Locally Amplified Strain Sensor Based on a Piezoelectric Polymer and Organic Field-Effect Transistors," Hsu Y-, Jia Z, Kymissis I., IEEE Transactions on Electron Devices. 2011; 58 (3). Also, the port may be constructed with a flat transparent bottom where only radial portion (a sector, 5620) is occupied by sensing electrodes. The sensing electrodes may be the same type as those described in FIG. 55. Further, FIGS. 56 (D) and (E) illustrate two different perspectives of such a design. The sensors are preferably arranged in a radial fashion (5620) so that the port can be rotated about its longitudinal axis to view and measure different portions of the tissue that is in contact with the flat bottom of the port. In other words, the rotating action exposes different regions and hence the entire bottom surface can be visually analyzed while the sensors arranged radially can be used to make electrical measurements. A port with a flat transparent bottom is typically introduced in the cavity after an introducer is removed from the tissue area.

Figure 57:
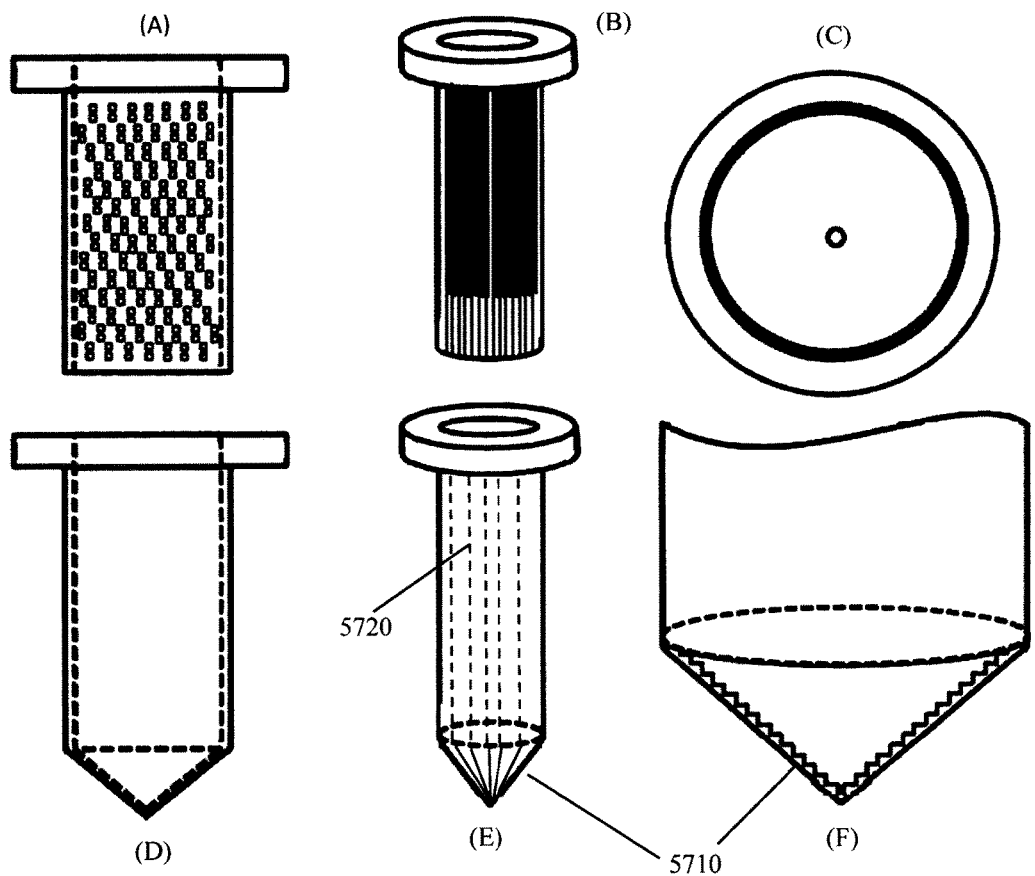
FIG. 57 illustrates an example implementation of an access port having an array of sensing elements for making physiological measurements.

Another example implementation is shown in FIGS. 57 (A) and (B), where the access port is lined with multiple elements of an electrode array. These electrodes can be employed for a number of uses, including, but not limited to, measuring physiologic activity, stimulating and measuring the response of nerves and tissues, and measuring strains (as a series of strain gauges). The electrode arrays may be also used to stimulate regions of the tissue in direct contact with the port. Hence, functional electrical stimulation may be performed using the same port during neuro surgery. In other words, specific regions of the brain that is in contact with the port may be stimulated while the same port provides access for surgical resection.

The front tip of the introducer may be lined with piezoelectric transducers to measure contact strain as the introducer is inserted in the tissue. Alternate means of measuring contact strain may be implemented on the introducer tip as described in "A Locally Amplified Strain Sensor Based on a Piezoelectric Polymer and Organic Field-Effect Transistors," Hsu Y-, Jia Z, Kymissis I., IEEE Transactions on Electron Devices. 2011; 58 (3). FIG. 57(C) illustrates the arrangement of electrodes from the top view of the same port illustrated in FIGS. 57 (A) and (B). Finally, FIGS. 57 (D), (E) and (F) illustrate arrangement of strain gauges at the tip of the introducer. The strain gauges may be piezoelectric transducers (5710) that are exposed on the surface and electrically connected (5720) to the proximal end of the port. The proximal end has electrical wires directly welded or attached via spring-loaded contacts (not shown). The wires are then connected to standard strain measurement system (not shown) such as a Wheatstone Bridge (as described in "Instrumentation for engineering measurements", Daily, James W. et. al., Engineering instruments, pg. 584, Wiley (New York)). The latter measurement system is a common means of measuring strain signals using a current source.

5. Optical

Insertable optical imaging devices according to the embodiments described here may be, for example, an insertable optical imaging probe, an insertable optical imaging introducer for inserting an access port, an access port with one or more integrated optical devices or channels provided therein, one or more optical imaging sleeves that are configured to be coaxially inserted into an access port, or various combinations of these insertable imaging devices, as illustrated in Section 1. Various example implementations of such insertable optical imaging devices are described in detail below.

5.1 Insertable Imaging Device with Integrated Optical Channels

The terms optical fiber and light guide can be used interchangeably in the following section. The optical fibers or light guides provide light delivery and/or collection from the tissue, with each fiber being purposed for illumination, light collection, or both. In addition, imaging could be performed using an insert optical imaging device comprising of a coherent array of fiber optics or light guides. In these configuration, each optical fiber or light guide provides a single illumination and/or collection measurement, which when combined with all other fibers or light guides provides a plurality of spatial measurements or an image.

Figure 58:
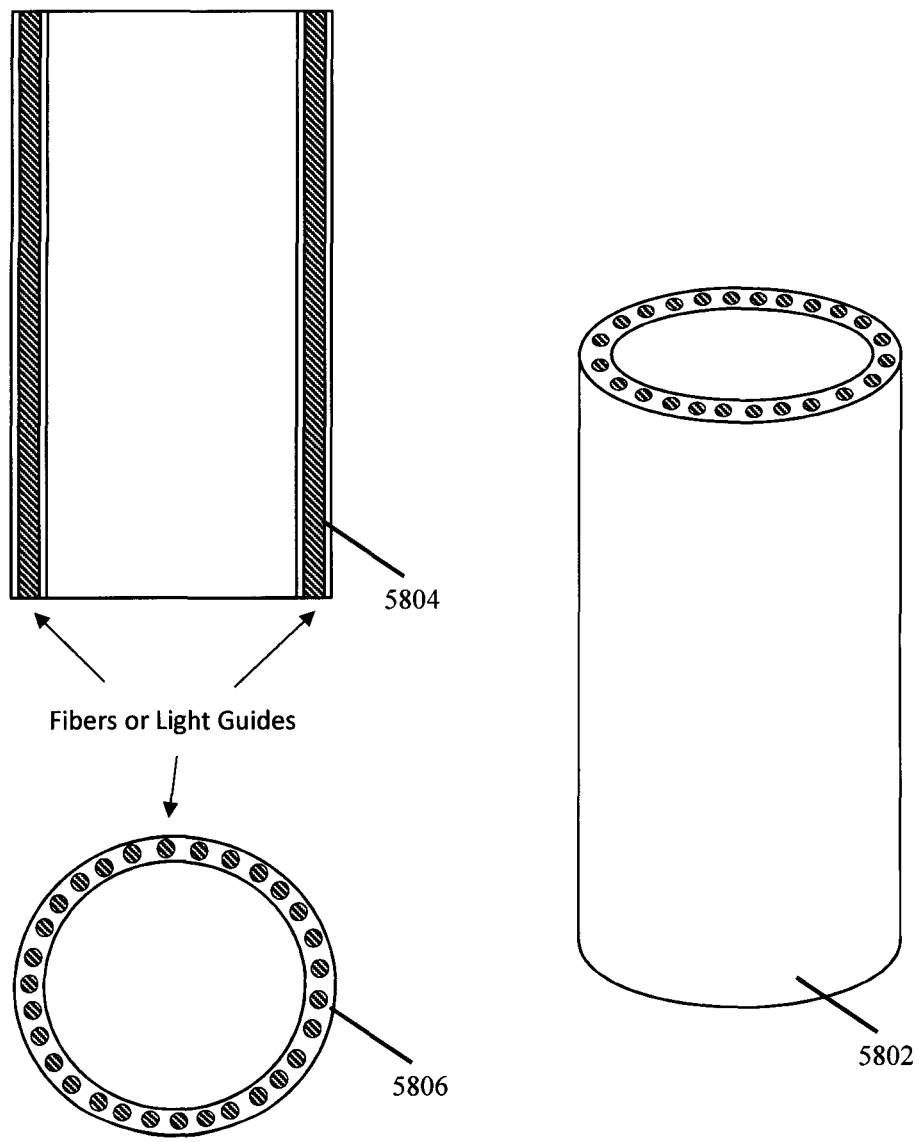
FIG. 58 illustrates light guides in walls of access port.

In some embodiments, optical measurements and imaging can be performed using fiber optics or light guides integrated into the walls of the access port as seen in FIG. 58 or in an insertable sleeve as seen in FIG. 59, or as an insert device as seen in FIG. 60.

Figure 61:
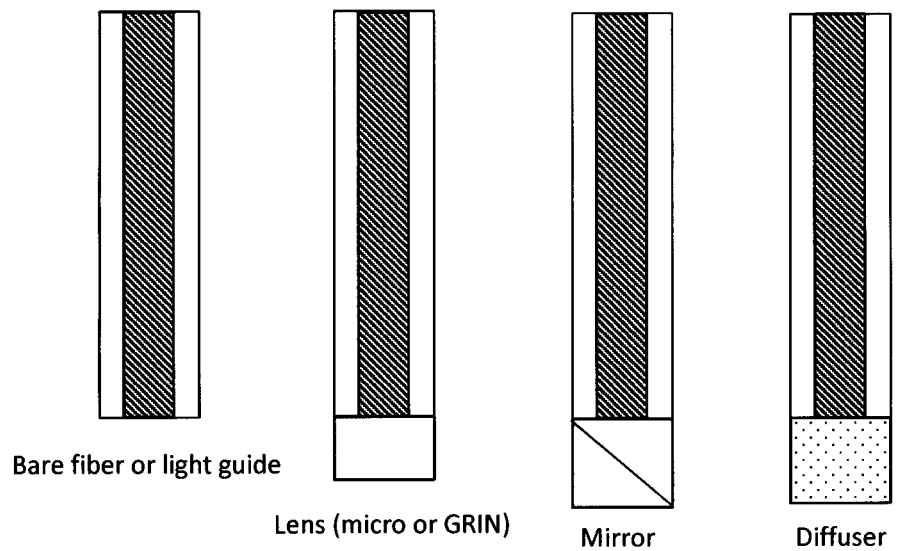
FIG. 61 illustrates different configuration for distal end of light guide.

FIG. 58 illustrates an example of light guides in the walls of an access port. At the distal end of an access port 5802, optical fibers or light guides 5804 can be bare or fitted with optical elements 5806 including microlenses and gradient index lenses to focus and/or collimate the illumination and collection light exiting and/or entering the fiber or light guide. Micromirrors can also be utilized to redirect the illumination or collection light in the desired direction. In addition, optical diffusers can be utilized at the distal end of the fibers or light guides provide directionally homogenized illumination light. Different configuration (i.e., lens, mirror or diffuser) of the distal end of fibers or light guides is illustrated in FIG. 61.

On the proximal end of the access port, sleeve, or insert device the fiber optics can be bundled together into a single or multiple fiber optic bundle cables as seen in FIG. 60. The proximal end of light guides can be optically and mechanically coupled to fiber optic cables, which can be similarly bundled together into a single or multiple fiber optic cables. A variety of optical imaging modalities can make use of these fiber optic or light guide structures including, but not limited to the following diffuse optical imaging (DOI), diffuse optical tomography (DOT), fluorescence diffuse optical tomography (FDOT) make use of multiple illumination and collection fibers to acquire optical measurement where the illumination and light collection locations/geometries are varied.

The acquisitions of measurements with vary illumination and detection geometries is used to construction a volumetric image of optical properties of the tissue (absorption, scattering, fluorescence, etc.), typically in a tomographic fashion. The multiple illumination and collection fibers or waveguides also form an ideal platform for multichannel or multiplexed optical coherence tomography (OCT). The acquisition of an OCT A-scan can be done through each fiber or light guide by either multiplexing using a single OCT detector, having detector for each fiber or light guide, or using spatially separated pixels or rows on an array or 2D detector. The fibers or light guides could also be used for excitation light for photoacoustic imaging (PA) if used in conjunction with an ultrasonic transducer to acquire the stimulated pressure wave, in this case the fibers or light guides would be used to delivery excitation light. More conventional optical imaging could also be performed using these fiber or light guide structures, particularly the insert coherent array where imaging is performed is a similar manner to conventional fiberscopes.

Beyond optical imaging modalities, these fiber or wave guide structures can be used for a wide variety of optical measurements either individually or as part of a multichannel systems. These measurements include, but are not limited to spectroscopy, NIR spectroscopy, Raman spectroscopy, surface enhanced Raman spectroscopy, stimulated Raman spectroscopy, and coherent anti-stokes Raman spectroscopy, fluorescence spectroscopy.

5.2 Insertable Optical Imaging Device with Integrated Optical Imaging Camera

In one example embodiment, a lower resolution video chip with an integrated lens may be placed as an insert to acquire local video information about the distal portion of the port.

According to various example implementations, the optical imaging device may employ imaging modalities such as visible imaging, infrared imaging (e.g. near infrared imaging), hyperspectral imaging, and Raman Imaging.

5.3 Imaging through a Conical Distal Portion of Introducer or Access Port

Figure 62:
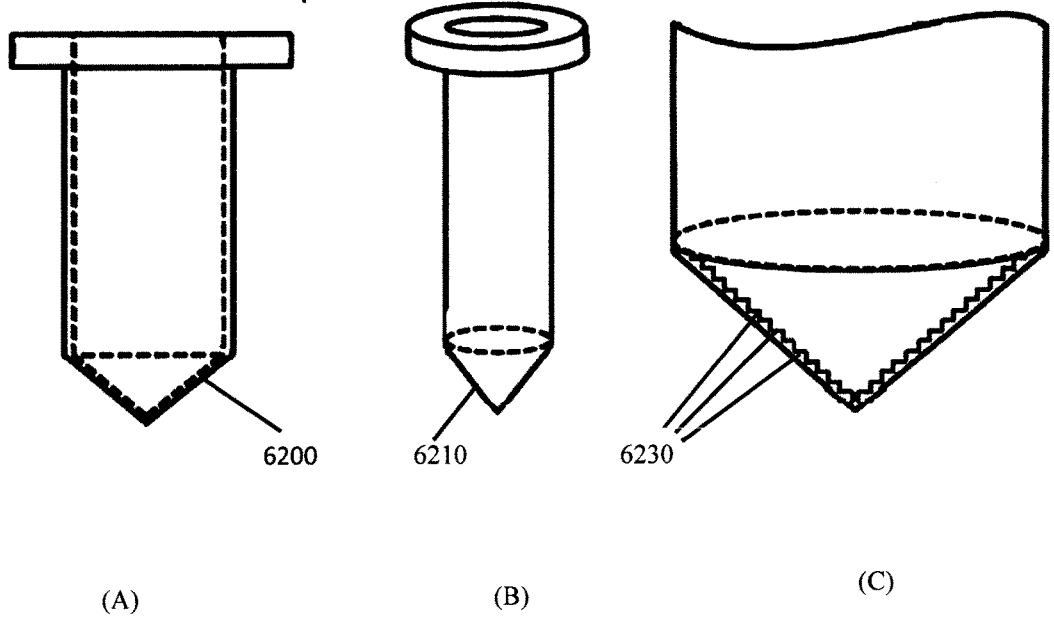
FIG. 62 illustrates an example implementation an access port or introducer having a conical distal portion that preserves the visibility of the path ahead of the conical portion.

In some embodiments, the design of the distal portion of the access port (6200 in FIG. 62 (A)) or the introducer (6210 in FIG. 62 (B)) can be conical in nature without compromising the visibility of the path ahead of the conical portion. This can be realized through use of Fresnel lens that is conical in shape (FIG. 62 (C)). The refractive indices of the concentric rings (6230) in the Fresnel lens can be modified such that the focal point of rays entering the various concentric rings is coincident. However, the facets or the grooves between concentric rings can generate visible artifacts and should be below the visual acuity of the human eye (approx. 1 arc minute). The pitch or width of the individual lens components should be such that Moiré patterns are minimized for the observation distance. The Fresnel lens is composed of concentrically arranged prisms. The exact focal point is adjusted by appropriately choosing slope angles and draft angles of the Fresnel lens prisms. The slope angle faces correspond to faces of prism that summatively create the intended image and draft angle faces are used to transition from one Fresnel prism to the adjacent Fresnel prism. These methods are described in optical design text books (reference: "Optical Design using Fresnel Lenses: Basic principles and some practical examples," Arthur Davis et. al., Optik & Photonik, December 2007, No. 4). The design is extended to a non-flat profile to match the conical profile of the port.

Any visible artifacts can be further reduced by acquiring the image through the port using an external video scope and then correcting for artifacts caused by grooves located between concentric lens rings in the Fresnel lens. A simple method for such correction is averaging of imaged pixels over an averaging area that is larger than the dimension of the draft angle of the Fresnel lens prims. Another correction method would be replacement of imaged regions corresponding to draft angle faces of the prism with values that are interpolated values of pixels corresponding to image created by slope angle faces of the Fresnel prism. This can be achieved since the geometries of the concentric portions are known and the exact distance of the distal portion of the insert port can be interfered from location of the port acquired through navigation systems or optical fiducial markers placed on the exposed surface of the port. This design will enable the surgeon to observe the brain structures as the port is introduced into brain. This embodiment is illustrated in FIG. 62. It should be noted that even though a standard staircase structure is illustrated for Fresnel lens, a uniform shape of Fresnel lens prisms will not provide the same focal point when the surface is not flat; instead, the slope angle and draft angle of the Fresnel needs to be varied to accommodate the conical shape of the imaging surface. A standard methodology described in "Optical Design using Fresnel Lenses: Basic principles and some practical examples, Arthur Davis et al., Optik & Photonik, December 2007, No. 4" can be employed to arrive at the optimal angles for the prisms.

5.4 Embodiments Providing Delivery of Light to Distal End of Access Port

All port-based surgical methods are limited by the amount of light that can be delivered to the tissue at the distal end of the port during surgical procedure. Introduction of tools occludes light delivery from externally placed light sources such as overhead surgical lamps. This limitation can be overcome as follows. Light energy can be projected onto the tissue via fibre bundles embedded in the walls of the port or by guiding the light through the port walls using total internal reflections within the wall. Light can be efficiently captured from an external light source using the ring located at the top of the port and then guided within the walls. Appropriately shaped lens can be fabricated along the top ring to maximize light capture and transmission to the inside of the port walls. A symmetrical lens will not be as efficient as a radially asymmetric lens fabricated or mounted on the top ring surface of the port.

Figure 63:
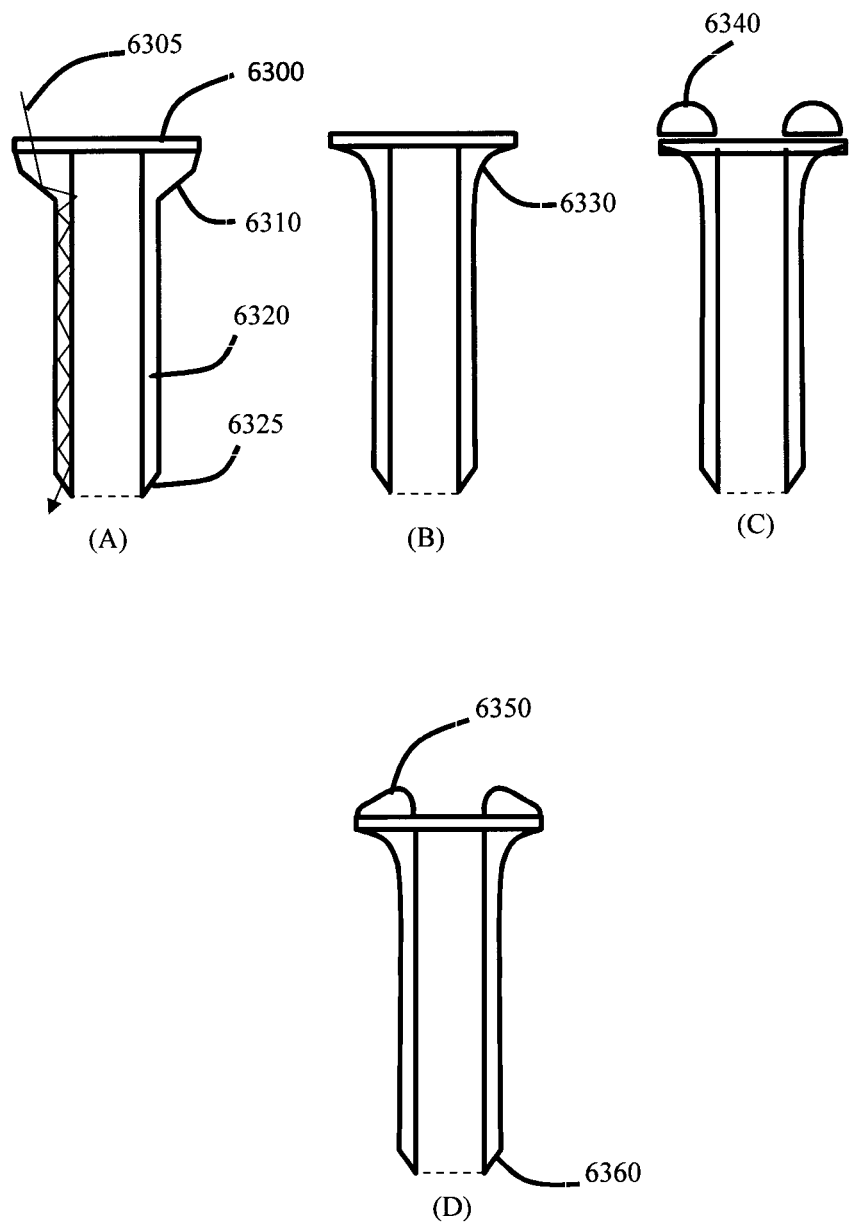
FIGS. 63A-D illustrate embodiments of an access port in which the walls of the access port are configured to guide light to a distal portion of the port via total internal reflection.

In another embodiment, light energy could be delivered with minimal occlusion by utilizing walls of the port as light pipe. FIG. 63A illustrates the design where the internal propagation of light beam 6305 from the top of the port 6300 to the distal tip 6125 of the port is facilitated by a slanted wall 6310. This can be further enhanced through use of a wall that has a gradually changing radius of curvature 6330) in FIG. 63B. FIGS. 63A and 63B are still limited by the amount of light incident on the top surface of the access port. Additional light can be captured and piped into the port through the use of lens structures 6340 shown in FIG. 63C.

Although not shown in FIGS. 63A-C, the delivery of light from the proximal portion of the access port to the distal portion of the access port can be facilitated by providing an outer layer on the outer portion (and optionally the inner portion) of the access port, where the outer layer has a refractive index such that the refractive index contrast between the outer layer and the access port is sufficiently high to support total internal reflection of light introduced in the top of the port. The refractive index contrast may be selected so that the effective numerical aperture of the access port is suitable for guidance of the light incident on the top of the port, such that light introduced over a given angular bandwidth (or solid angle) is totally internally reflected when light propagating within the walls of the access port encounters the outer layer.

This design aids in the collimation of light arriving at various angles into the port walls. This design can be further enhanced through the use of radially asymmetric lenses 6350 to maximize light capture, as shown in FIG. 63D. Finally, light emanating from the distal end into the tissue region can be preferentially directed using similar lens structures fabricated at this tip 6360. Hence, particular f/# (also known as 'f number') of the output beam can be achieved based on the design of the lens at this tip.

6. Multiple Imaging Modalities

Figure 53:
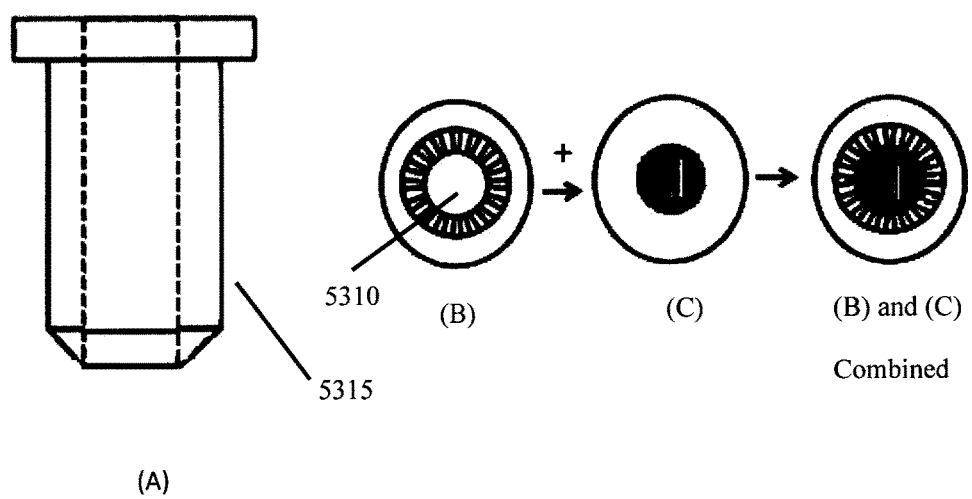
FIGS. 53A-C illustrate another example implementation of an insertable ultrasonic imaging probe having an ultrasonic transducer integrated therein, where the introducer includes an opening.

FIG. 53 illustrates one arrangement for combining multiple modalities. An outer coaxial array of ultrasonic transducers can be combined with one of open cavity, inner radial array of ultrasonic transducer or smaller MR coil array. This arrangement allows the removal and introduction of different imaging modalities during surgery.

In one embodiment, a smaller opening can be left in the middle of the probe to facilitate access for surgical procedures. The insert probe shall be held at a consistent location using an external holding assembly that shall be firmly and removably affixed to an external reference frame used for the purpose of surgical navigation. Hence, local images acquired through the insert probe can be easily registered with pre-operative whole-head images. Alternatively, the insert imaging devices may be secured to the skull surface.

In a further embodiment the insert-imaging array may consist of two or more inserts that fit inside each other (see, for example, FIG. 10). In this way different combinations of imaging modalities can be used that are complementary to one another for the appropriate surgical purpose. Shown on the top left of the FIG. 53A is an external port with an opening in the middle, that accommodates a pointed, atraumatic tip introducer. On the bottom right of the FIG. 53C., we see the external port on end view illustrated with an array of radially arranged transducer elements. Inside of this port can be placed multiple inserts. On the top right we see an additional ultrasound array, this array may be an array with a different detection/excitation frequency, or a set of elements that can be used in concert with the external array. In the middle is shown a single element. This element may be an optical fiber, or a single ultrasound element. In the bottom is shown a radial array, where each arm of the array consists of multiple elements. In all examples these elements may exchange ultrasound, optical or MRI elements. The opening 5310 in FIG. 53B may be used to excite tissue using pulsed laser and the resulting photo-acoustic emissions may be captured using the ultrasonic receiver array. In another embodiment, the pulsed laser may be targeted by a robotic arm positioned above the port with the arm positioning the pulsed laser in a raster pattern or random sampling pattern on the exposed tissue at the bottom of the port.

FIG. 57 illustrates an example embodiment involving both MR and ultrasound transducer elements in the insert device placed in the port. The MR transducer coils may be constructed from strip lines, loops or bipolar coils. Further, the coils may or may not contain a local magnet.

In one embodiment the device provides localized magnetic resonance images that enables parallel imaging protocols by way of multiple channel coil imaging, while also providing a means to enable additional imaging modalities such as ultrasound, optical imaging, hyperspectral imaging and photo acoustic imaging. This device can be inserted and/or re-inserted during imaging protocols to provide updated MR images of the area of interest during points of a surgical procedure. It should be further noted that in the case of embodiments involving multiple imaging modalities, the said modalities can be registered relative to each other since the respective transducers are located at fixed geometric locations relative to each other. Hence, image acquired in the first modality can be geometrically transformed to appropriately overlap with the image acquired using the second modality.

The following are further examples where multiple transducers can be used with multiple imaging modalities:

6.1 MR-Elastography

Similarly, the stiffness of various regions of the brain that are close to the port coil can be estimated using MR-elastography. This technique presents the elastographic data as an image map. In this embodiment, the conductive elements along the perimeter of the port can be interspersed with piezoelectric plates driven by a pulse generator that oscillates at approximately 300 Hz. The resulting vibration is transmitted to the tissue and relative movement of the tissue can be imaged via MR imaging techniques. Hence, a stiffness distribution of tissues in the vicinity of the port can be generated to identify presence of different tissue types. Use of this elastographic information to model tissue deformation is presented in PCT Patent Application No. PCT/CA2014 050243, titled "SYSTEM AND METHOD FOR DETECTING TISSUE, FIBER TRACT DEFORMATION" and filed on Mar. 14, 2014, the entire contents of which is incorporated herein by reference.

6.2 Other Imaging Modalities Involving Excitation of Tissue

In addition, proximity to the tissue, particularly in the case of the brain, providing access through the skull and, hence, enables a multitude of tissue excitation methods previously not anticipated or possible. For instance, one may provide a local audio vibrational excitation to allow for elastography imaging (using MRI, US or OCT), or provide for novel photo-acoustic excitation strategies, including direct excitation down the port, or through the patients ear canals. In the case of elastographic imaging, the stiffness of the tissue can be measured as the device is being driven through the tissue and then displayed to the surgeon. As described previously, use of optical delivery paths in the port enable the use of optical measurements systems such as OCT for understanding elastographic property of local tissue and polarization imaging to visualize anisotropy of the tissue.

6.3 Insert Imaging Devices Including Mechanism of Infusing Contrast Agents

Additional designs embodiments of the distal portion of the insert component include the ability to infuse into the adjacent surface, a known concentration of contrast agent. In this way, a controlled delivery of fluids can be delivered to targets of interest in ways not previously allowed due to the presence of the blood-brain barrier. The infusion strategy can include, for example, a pre-saturated surface of contrast agent; an irrigation tube or array of tubes on the surface, that can deliver saline, contrast agent, or chemotherapy locally that allows for clearance of fluids (this allows for better distal surface imaging, as well as clearance of contrast agents to enable local bolus delivery of agents); an integrated suction device or array to remove fluids; or an activated array, that delivers agents only when activated (either by a touch probe, or interaction with the navigation system).

Such embodiments can be used to deliver a variety of contrast agents, such as MRI based contrast agents (gadolinium, iron-oxide particles, etc.), CT (Iodine), Ultrasound (micro-bubbles), photodynamic contrast agents (gold spheres, carbon nanotube agents), PET (nuclear agents). Including biological bound contrast agents.

In addition, the concept can be extended to include chemotherapy agents. In the manner described above, specific locations within the port field of view can be indicated (either through navigation system or touch), and the chemotherapeutic agents can be delivered to those areas. In this way the systematic delivery of agents through the vascular system can be avoided. This provides the ability to deliver a high dose to an area of interest, as well as being able to delivery multiple agents to various regions. Fast acting chemo-therapy agents may also be flushed from the area.

To provide for even more accurate delivery of therapy, a combination of detection and treatment agent can be used, for instance photodynamic therapy. With the method described prior, localized delivery of agents can be performed, and an external light source can be used to activate the photo-sensitizing agent.

6.4 Bottom of Insert Component Having "Flat Transparent Surface Laden with Biochemical Assays"

In another embodiment, the distal portion of the insert component may be a flat transparent surface that is laden with biochemical markers arranged as a micro-array or as a binding surface with a single type of binding molecule. An embodiment of this may be a substrate (distal portion of port that is covered) that has specific receptors laid out in patterns. A non-limiting example of a receptor may be calcitonin receptor (reference: "The expression of calcitonin receptor detected in malignant cells of the brain tumor glioblastoma multiforme and functional properties in the cell line A172," Wookey et. al., Histopathology, 2012 May, 60(6):895-910). The composition of the chemical assay shall be any of previously published biochemical means of differentiating tumor and healthy tissues. The selective binding of tumor cells or particles associated with them may be measured using an external video scope equipped with sensors sensitive to the appropriate wavelengths (e.g. Hyperspectral imaging at specific wavelength ranges). Alternatively, the binding surface may be illuminated using a technique similar to that described in US patent (U.S. Pat. No. 7,314,749) to automatically identify selective binding of molecules and cells.

Figure 67:
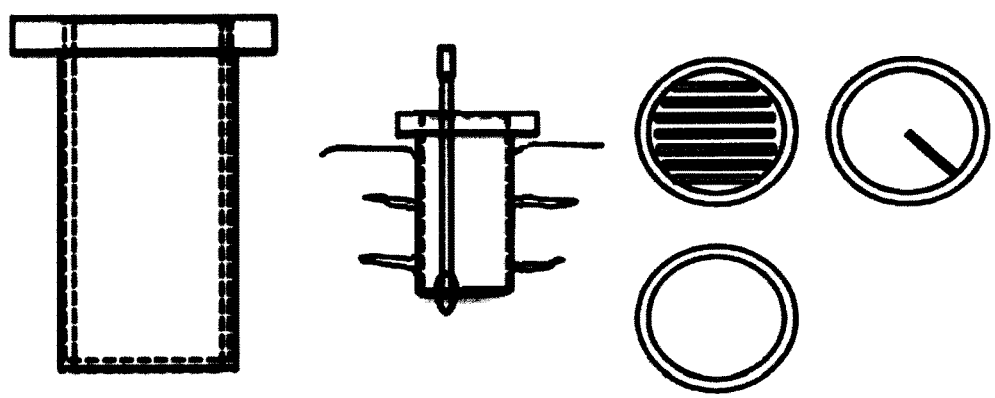
FIG. 67 is an illustration demonstrating an example embodiment involving the use of microarrays attached to a port.

An example arrangement for illustrating this embodiment is shown in FIG. 67. As seen in FIG. 67, specific receptors may be attached to a grid-like substrate 6702 at the distal end of access port 6706. An externally positioned camera 6704 may be used to detect selective binding of molecules to the specific receptors. Camera 6704 detects these binding through such chemicals as fluorophores attached to the molecules.

7. Tracking and Incorporation of Fiducial Elements 7.1 Tracking of Probe

Once the MR imaging probe has been inserted, it may be fixated to a mechanical arm for stability during imaging, or to the port cuff or surgical clamping device, or alternatively held in place manually. This port coil may form part of an overarching navigation system in which case the MR Imaging Probe's location will be tracked and recorded. The use of tracking system or vibration sensors located on the Imaging Probe can also enable detection of movement of the probe during measurement and appropriate compensation for motion artefacts introduced in the acquired data.

In addition, calibration elements may be included, as well as fiducials, to allow for accurate registration. Coupling this probe with a tracking, or position device will allow for 3D imaging reconstruction if the imaging planes of interests are known. Coupling this imaging device with external volumetric imaging systems (whole organ), will allow for a larger scale volumetric scan if needed (i.e. significant tissue removal or deflection during surgery).

Within the port coil, fiducial elements may be included for reference, navigation, or registration purposes. These fiducials may be T1 and/or T2 markers and are intentionally included within the imaging area of the MR probe. When the MR probe is used after the retraction of an introducer, the former component may be equipped with a pressure sensor at the tip so that a signal is generated when the port coil reaches the tissue surface. This signal can be translated into a warning signal to alert the surgeon that the port coil has reached the tissue surface and hence prevent application of excessive pressure on the tissue surface.

8. Use of Insert Imaging for Minimally Invasive Procedures

Figure 65:
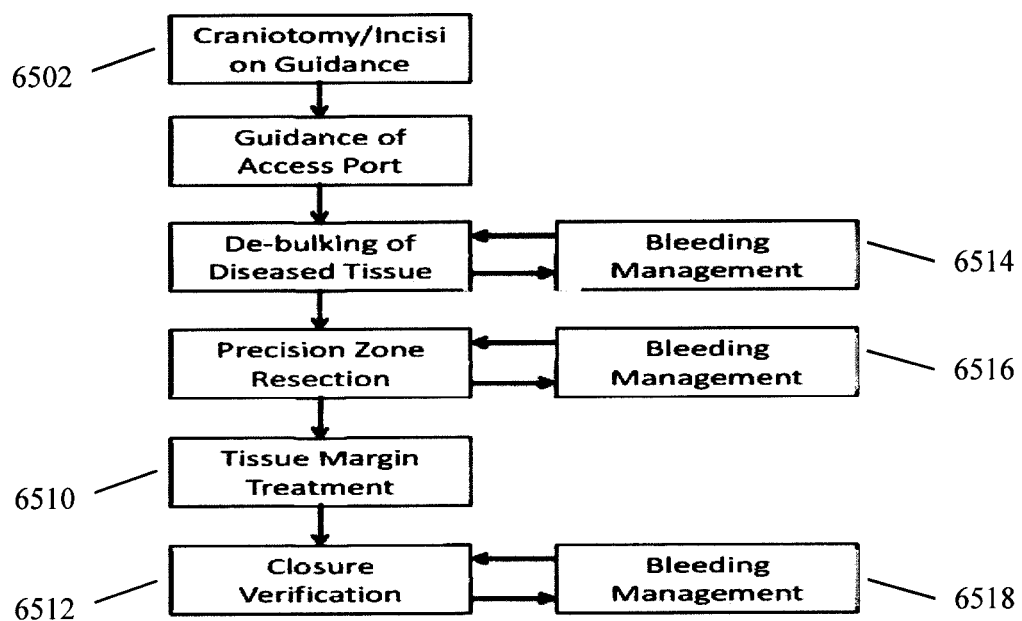
FIG. 65 shows a flowchart depicting the stages of minimally invasive port based surgical procedure where imaging is valuable as an integral tool.

FIG. 65 shows a flowchart depicting the stages of minimally invasive port based surgical procedure where imaging is valuable as an integral tool. In FIG. 65, the first step is the incision of the scalp and craniotomy (step 6502) where a bone flap is temporarily removed from the skull to access the brain. The next step is guidance of the access port (step 6504) into the brain typically with assistance of a navigation system. Thereafter, the surgeon will debulk the tumour or disease tissue (step 6506). The surgeon may follow that up with precision zone or fine resection (step 6508) to further remove any finer tissue details. Next, the surgeon could perform tissue margin treatment (step 6510) by delivering therapeutic agents to the surgical site to remove any remainning unhealthy tissue from the area and assure an optimal recovery. The final step is closure verification (step 6512) which involves the removal of the port and closure or suturing of the wound in addition to the application of materials to assist in healing the surgical area. Furthermore, in steps 6506, 6508 and 6512 bleeding management is monitored and contained which is represented by 6514, 6516 and 6518, respectively.

Several stages of a minimally invasive procedure, including similar procedures applied to the brain, will benefit from the use of appropriate imaging modalities. Application of specific imaging techniques and their embodiments for surgical removal of brain tumors is explained in the next several sections.

Figure 68:
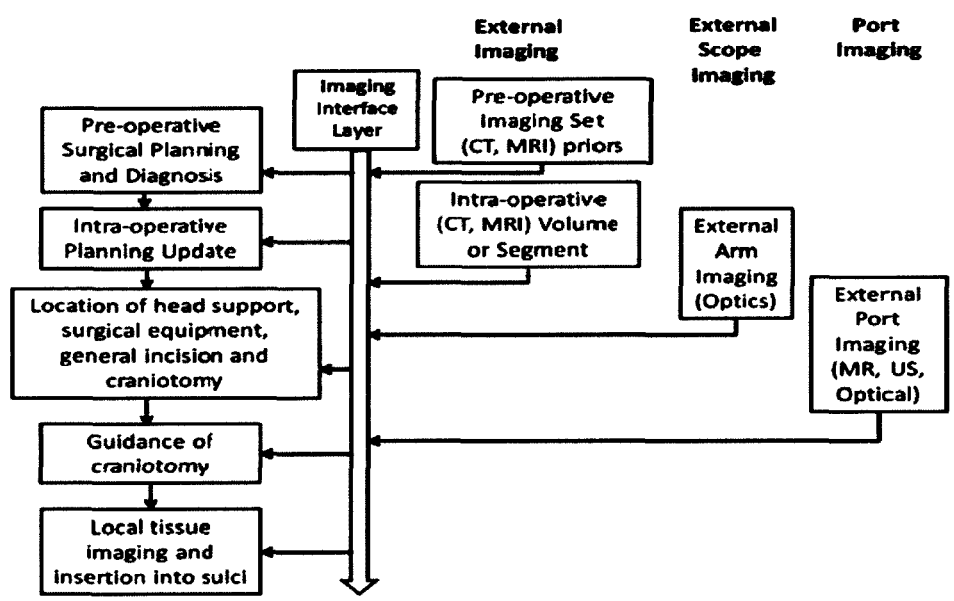
FIG. 68 shows a flowchart depicting the utilization of imaging data for craniotomy/incision guidance.

FIG. 68 shows a flowchart depicting the utilization of imaging data for craniotomy/incision guidance, in particular, the different surgical steps and application of specific imaging modalities. The imaging modalities can be broadly grouped into external imaging, internal scope-based imaging and port-based imaging to capture different scales of clinically relevant images. All of these images may be co-registered and presented to the surgeon using a unified framework (depicted as "Imaging Interface Layer" in FIG. 68).

Figure 26:
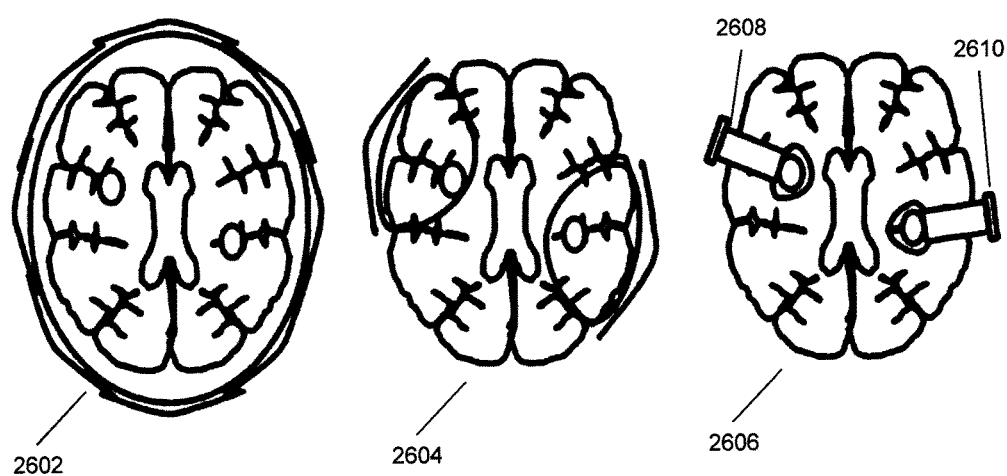
FIG. 26 is an illustration demonstrating the imaging coverage on a brain using multiple coil arrays.

The imaging devices used may consist of external imaging devices, either full-volume or sub-volume surface arrays, port based insert-imaging devices, external arm optical imaging devices, surgical tool based imaging devices, or margin surface imaging devices. At each stage the appropriate contrast and resolution may be selected for imaging. Imaging using various MRI sensors to cover various arrays of interest is shown in FIG. 26, where a full volume array is shown on the left 2602, a regional array in the center 2604, and a local port area coil on the right 2606. On the right image 2606, access ports (2608 and 2610) integrated with imaging coils is seen inserted into the brain.

Figure 66:
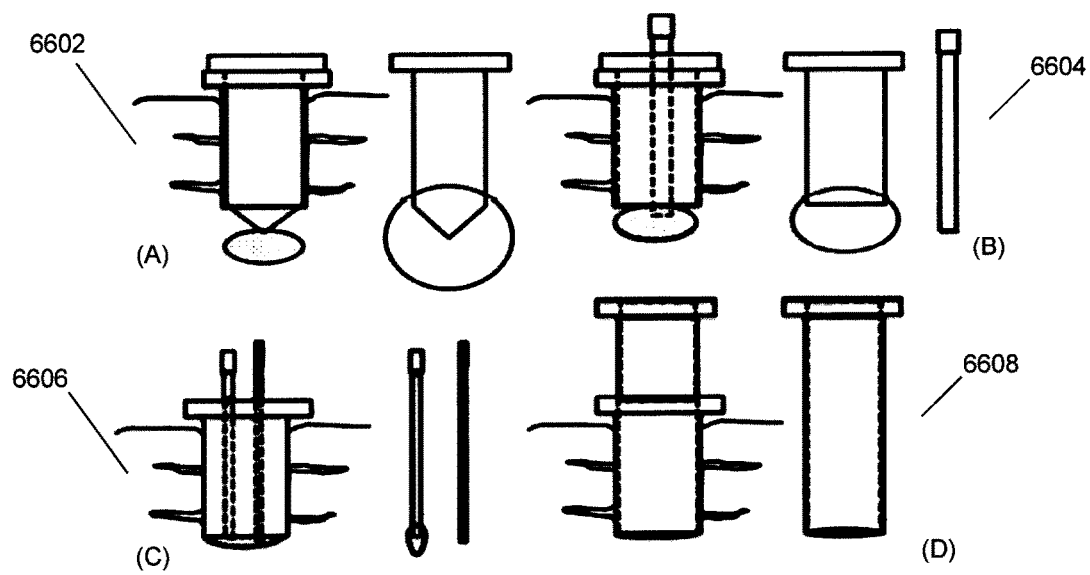
FIG. 66 is an illustration demonstrating an example embodiment involving insert imaging devices with differing imaging fields and resolutions.

FIG. 66 is an illustration demonstrating an example embodiment involving insert imaging devices with differing imaging fields and resolutions, shown as (A) and introducer imaging array, (B) a port imaging array, (C) a tool imaging array, (D) a surface imaging array. In FIG. 66, there are four different scales and resolutions of imaging devices shown in the context of delivery of the devices to the tumor (top left 6602), imaging the surgical field of the tumor, (top right 6604), imaging a thin volume along the edge of the tumor (bottom left 6606), and imaging of a very thin volume of tissue, along the margin of healthy tissue (bottom right 6608).

8.1 Use of Insert Imaging Modality to Obtain Improved Contrast Images Relative to Pre-Operative Contrast Images In one embodiment, imaging contrast mechanisms that were acquired with a pre-operative imaging modality, will be able to be performed with the insert imaging modality, except with a higher performance (higher signal to noise, and/or higher resolution image). For instance, tissue anisotropy, water content, oxygen concentration, blood flow, tissue stiffness, etc.

8.2 Real-Time Imaging During Insert Process, Sulci-Based Port Delivery

In some embodiments, the device may be configured to perform various multi-modal imaging combinations in real-time while it is being inserted. Imaging in this way allows for delivery of the insert device to the location of interest with updating imaging guidance. For example, the sulci may be detected as the device is inserted. These structures provide minimally invasive orifice access into the brain, and their distinctive folds and branch points can provide a means to navigate to the point of interest. In addition, unique patterns of vessels can be used as internal landmarks. Most neurosurgical applications do not plan the delivery of the tracked devices along a specific trajectory, but rather a only target to a point—in the application of sulci-based port delivery, the trajectory is also important so as to minimize the white matter trauma of the patient.

Upon successful navigation, the body of the imaging device can then be removed, while leaving the rigid tube structure in place to allow for surgical access to the tissue. The outer sleeve can be inserted using the introducer through the sulci and subsequent retraction of the introducer. The inner imaging array can be inserted at any time to allow for re-imaging of the tissue.

8.3 Surgical Planning—Craniotomy/Incision Guidance

The first stage of surgery generally involves utilizing images of the whole head, in order to determine the location of the diseased tissue, the minimally invasive access corridors, and the structures that need to be avoided (vessels, white matter tracts).

Typically a pre-operative scan (done on a previous day) has been done using MRI or CT, that allows for diagnosis of the tissue, and visualization of the critical structures in a single scan. If multiple scans are required (MRI and CT), they are registered using a variety of strategies. In some cases, intra-operative scanning (at the time of surgery) may be performed, before the incision is made into the head, which could provide for more accurate surgical guidance information as it is acquired at the time of the surgery. Current systems do not provide for high performance imaging intra-operatively either due to limited performance coils of MRI hardware.

Alternatively a localized coil may be used to image the region of interest that is important, for instance, the quadrant of the brain for which the incision is planned. Until the skull is opened in surgery, it is expected that the brain position would be substantially similar to the position in which it was in for pre-operative imaging, however once a piece of the skull is removed, the brain will swell outside of the skull, where it has been documented the shift of the brain at that point could exceed 1 cm.

Therefore quadrant, or whole head imaging done pre or post skull resection addresses the following concerns: differences in patient position and general brain condition (brain sagging or swelling); pathologies causing shifts and displacements—i.e. growth of the tumor, fluid build up, internal bleeding since pre-operative imaging; brain shift due to skull opening-craniotomy (smaller with burr-hole; poor tissue differentiation—higher resolution local imaging (higher acquisition matrix can be addressed when imaging a smaller volume of interest); the need to provide better visualization of tumor close to surface for better surgical planning and compressed gyrus to locate sulcus for sulcus based approaches; and poor differentiation of sulci, nerves and tumor pre-operatively—focused local imaging will provide better imaging locally (higher resolution, better contrast, better defined nerve fibers (more angular acquisitions, thinner slices).; reduced brain shift due to large craniotomy—better located craniotomy and smaller dura opening reduces brain shift; and more accurate location of head supports (pinning) based on more accurate intraoperative plan (reduce head trauma associated with poor head pinning).

Imaging may be performed using a whole head coil array, a quadrant array, or by positioning a port coil close to the entrance of the skull. In addition, according to embodiments disclosed herein, after the skull has been resected, MRI imaging can be done using the insert coil, US imaging can be done through the burr-hole, or surface imaging can be done through the dura using an external optical imaging system (photo acoustic imaging has been shown to image sulci through the skull and dura, where US will permit imaging through the dura, and can adequately visualize sulci with a high frequency probe (upwards of 7 Mhz)).

MRI imaging can be directly registered to the pre-operative MRI images, or alternatively the structure of the gyrus, or blood vessels in the area may be used to register to pre-operative structures. If the visualization of the sulci is difficult to determine before the craniotomy or dura opening, additional sequences may be acquired at the discretion of the surgeon.

8.4 Guidance of Access Port

Figure 69:
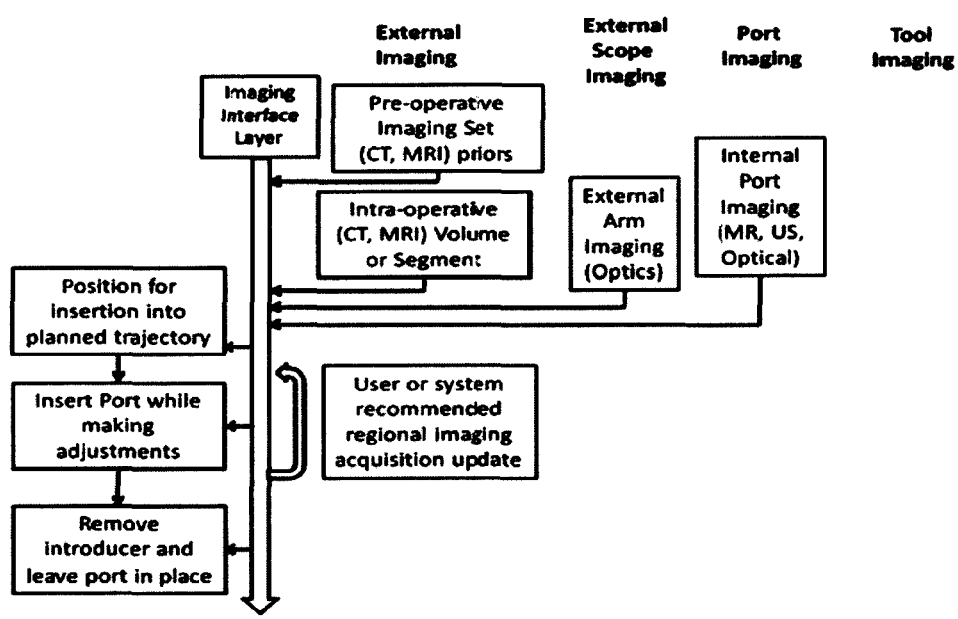
FIG. 69 shows a flowchart depicting the utilization of imaging data for guidance of the access port.

Once the pre-operative plan is updated, craniotomy is made, and opening made in the dura, the challenge is delivery of the port to the tumor, following a minimally invasive path (as measured by white matter and cortex traversal), while following the selected path (often the sulci). The steps of the surgical procedure are shown in FIG. 69, in coordination with possible imaging modality utilization.

Imaging at a smaller field of view (less than 6 cm, 1 cm close to tumor), a faster temporal resolution (approaching 30 fps), and higher resolution that is more appropriate to insertion of a port into the brain (less than 1 mm to resolve sulci), will address the following problems at this stage of the procedure: travelling down an incorrect sulcus corridor; traversing or puncturing the sulcus; traversing or puncturing critical banks of grey and white matter; puncturing/shearing or cutting a blood vessel; mis-targeting or displacing the tumor; avoiding moving off of pre-planned navigated pathway; navigating past nerves in real-time (i.e. taking a non-linear pathway); measuring tissue stiffness to minimize tissue mechanical trauma; measuring tissue state—measuring electrical activity and/or measuring tissue oxygenation and/or tissue pH, and/or tissue anisotropy.

It is expected that the introduction of the port, and introducer will displace a significant amount of tissue internally, as well as displace the folds of the sulci as it is pushed into the brain. For tissues that are stiffer than the surrounding brain tissue, for instance some clots/hematomas, cellular tumors, there will be an expected internal shift of tissue as the introducer pushes against the tissue.

In one embodiment, this displacement can be predicted with accurate simulation, using a priori tissue stiffness information, geometric knowledge of the introducer and port, a biomechanical model of tissue deformation, (using the skull as a boundary condition) and using pre-operative imaging data. This model can be updated using real-time imaging information as the introducer is positioned inside of the head, and more accurately if real-time imaging is performed using the in-situ port. For instance, real-time ultrasound imaging done on the tip of the port, can detect tissue stiffness inside the brain. This information can be used instead of the priori-predicted stiffness, and can provide a better estimate of tissue movement. In addition, ultrasound can be used to identify sulci patterns as the port is being introduced. These sulci patterns can be matched to the pre-operative sulcus patterns, and a deformed pre-operative model can be generated based on this information.

Alternatively, the port can be guided based on the actual real-time imaging from the port. In the most basic form is the use of an optical path to the bottom of the port by way of a set of glass fibers, or a clear path with a lens at the bottom that is aligned with an external camera (as described in a related patent application—see below). Alternatively a combination of an optical lens, and a plurality of US elements could be used. In this combination the US elements may be mechanically scanned, or focused appropriately to image forward and sideways, thus providing an optical and US image in real-time. Alternatively, or in addition, photo-acoustic imaging may be used with an external laser excitation, and receiving using the ultrasound elements. Alternatively, or in addition, OCT may be used to measure local tissue structure, Doppler imaging, or in-combination with photo-acoustic imaging. For the purpose of guiding the port into position, there should be at least a 1 cm forward field of view for imaging. Optimally the field of view would be larger when inserting into the sulcus, and when approaching the tumor, it would be reduced, and the imaging resolution is increased.

It is expected there will be a discrepancy between the pre-operative imaging data, and the real-time port information (US, OCT, photo acoustic, optical). This can be measured by matching sulci patterns, blood vessel positions, or by quantifiable common contrast mechanisms such as elastic modulus, tissue anisotropy, blood-flow, etc. The real-time port information would be expected to represent the truth, and when there is a significant discrepancy, a scan would be done to update the volumetric MRI and/or CT scans to update the pre or intraoperative scanning volume. In the optimal configuration, an MRI port coil would be used in conjunction with an external MRI system to acquire a 3D volume demonstrating sulci path, tumor, nerve fascicles by way of DTI acquisition, and blood vessels. As the acquisition time is typically much longer than US, OCT or photo-acoustic imaging, it is not expected to be used as a real-time modality, however it can be effectively utilized as a single modality to position the access port with pseudo-real time capability (typically not faster than 1 fps).

Alternatively sensors on the outside surface of the port, can measure quantifiable physical measures, such as electrical conductivity/resistivity, stress/strain, temperature in real-time. This provides valuable physiologic information pertaining to the forces applied to the nerve fibers, the port (and associated tissues), and the nerve activations. This real-time physiologic information can be used to ascertain tissue conditions around all surfaces of the port.

8.5 De-Bulking of Diseased Tissue and Precision Zone Resection

Figure 70:
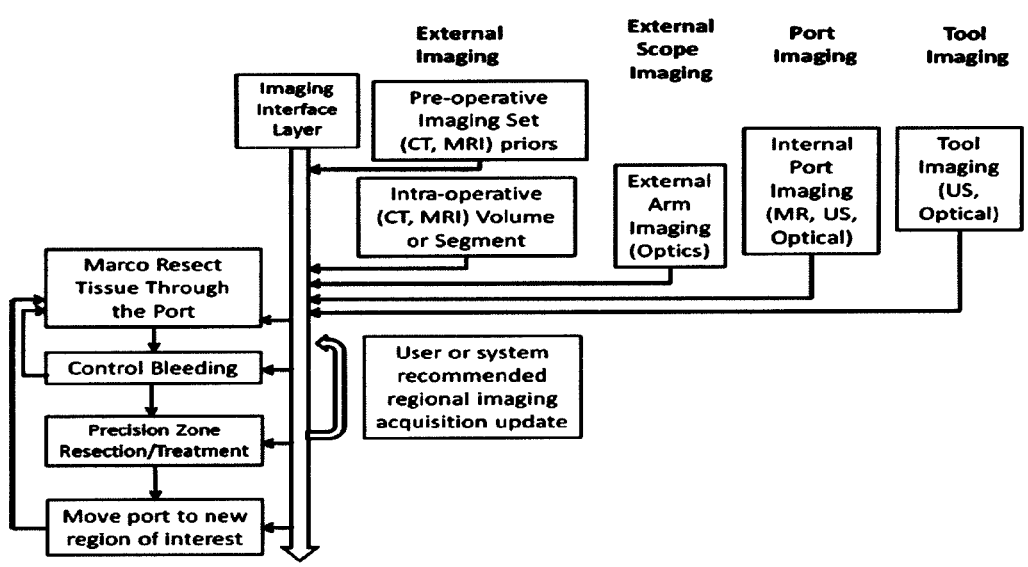
FIG. 70 shows a flowchart depicting the utilization of imaging data for de-bulking of diseased tissue.

FIG. 70 shows a flowchart depicting the utilization of imaging data for de-bulking of diseased tissue. Once the port has been positioned into the tissue of interest by way of imaging guidance, the introducer can be removed and the access to the tissue granted through the opening in the port.

The objective at this point is to establish a pattern of tissue resection, bleeding management, and port alignment so as to remove the maximum amount of diseased tissue, while, minimizing trauma to surrounding tissue. This will be done in conjunction with clearing the margins of the tumor, where the diseased tissue comes into contact with normal brain tissue.

The process involves a multi-resolution approach to resection of tissue at a coarse resolution with coarse tools (for instance using scissors, forceps, tissue ablation, suction or large volume aspiration cutting tool setting) in combination with real-time imaging, (external video scope feed), and fine resection using shaving tools (for instance small volume aspiration cutting tool, or small focus laser ablation), in combination with high resolution imaging (high resolution focused external video scope, tool based OCT, tool based spectroscopy, tool based US, tool based photo acoustic). In each case, the imaging resolution, and field of view is appropriately sized to the surgical implement.

Imaging in this manner allows the following issues to be addressed: healthy to diseased tissue differentiation in vivo; visualization of blood vessels to better manage bleeding and cauterization; imaging of nerves in vivo to avoid their resection/damage; tracking of pathology samples to known imaging properties (currently not possible in any surgical or radiology system); and assessing the state of grey matter/white matter in-vivo.

Surgical resection through port necessitates focus on the local surgical volume of interest distal to the opening of the port and the volume beyond. By tracking the port relative to the pre-operative, or previously acquired intra-operative images, the corresponding pre-operative volume can be presented relative to this opening. The ability to track a port in the context of the immobilized patient head, external scope and navigation system, is demonstrated in FIG. 8. FIG. 8 is an illustration demonstrating an example simplified neurosurgical configuration where a port 802 is held by a skull based guide clamp 804. Tracked tools 806 may be placed down port 802. Nearby is an equipment tower 808 containing imaging and navigation system 820. Navigation system 820 assists in aligning port 802 using an automated imaging arm 810, tracking camera 812 and external imaging scope 814. External video image and preoperative images are shown on two separate monitors 816 and 818 respectively.

However as the surgery processes, this volume becomes a less accurate representation of the actual tumor, margin and surround tissue position. In order to achieve a more accurate local representation, a new volume representing the local region of interest can be acquired. For instance, an MRI port coil can be introduced into the coil and a 3D volume may be acquired (approximately 2 cm volume). In addition, a scan of the volume can be accomplished using high-frequency ultrasound (5 mm-2 cm), OCT (2-3 mm), or photo-acoustic imaging (variable field of view with resolution, therefore 2 cm to 2 mm).

Figure 72:
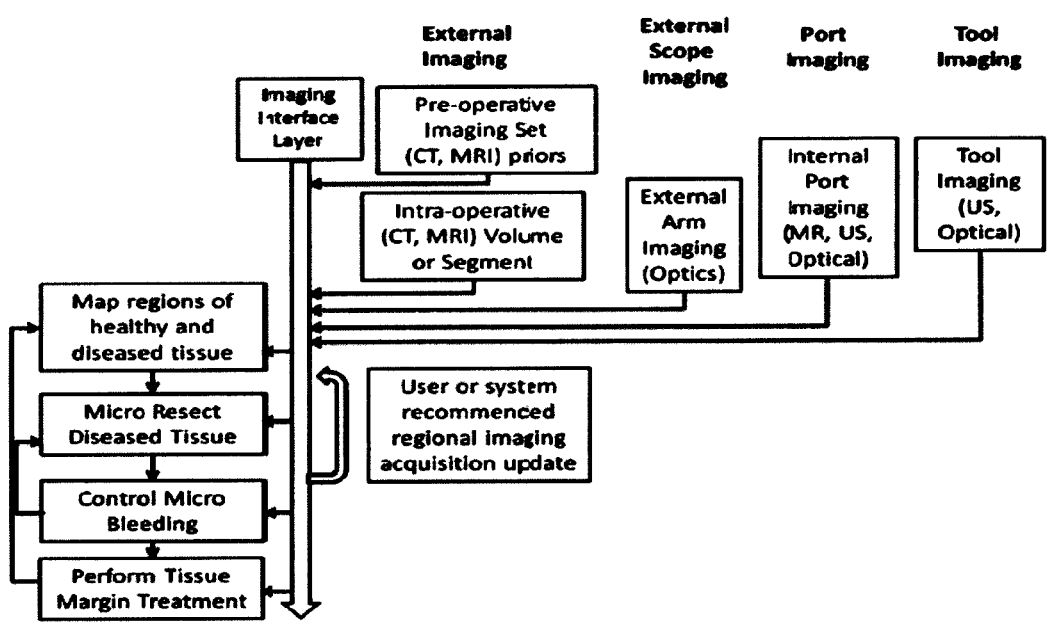
FIG. 72 shows a flowchart depicting the utilization of imaging data for precision zone resection.

This newly acquired information can provide the best representation of the surrounding tissue for resection. When approaching the margins of the tumor, local imaging devices, or point source imaging can be utilized to define volumes on the order of 1 mm-5 mm. This is presented in FIG. 72, which shows a flowchart depicting the utilization of imaging data for precision zone resection. In this mode, the boarders of the diseased tissue can be resected, and the condition of the tissue can be established.

In addition, Raman spectroscopic probes can be used to gather chemical information relating to the tissue, and the multiple imaging signatures of resected tissue can be recorded and tracked relative to specific surgical resection samples. This information will be important to select the appropriate margin treatment protocols, and help to identify tissue types relative to other tissues in the same patient, or between patients.

One aspect of the present disclosure is the ability to use the distal surface of the port, or any imaging devices inserted into the port to immobilize tissue. This is demonstrated in FIG. 67, where on the bottom row, a port insert is shown with an additional insert whose purpose is to immobilize the tissue at the end of the port. By doing so in conjunction with any of the insert imaging devices, very high-resolution imaging, and accurate tissue location can be achieved in a manner currently not achieved (i.e. tissue immobilization relative to an external reference, controlling for tissue pulsation, respiration and general movement). As will be discussed further, this provides unprecedented ability to perform tissue treatment and ablation.

8.6 Tissue Margin Treatment

Current surgical procedures are limited by the inability to image at a very fine resolution, provide fine tissue contrast, and provide tools to selectively resect small areas of tissue, or small populations of cells. The use of microscopes can be effective at the surface of the brain, but in deep tissue, or tissue with pulsatile flow, this is not possible. In addition, current tools, or the precision of the surgeons hand with a scalpel is limited to >400 micrometers. Relative to the novel imaging modalities immerging, where resolutions of 10's of micrometers are achievable, this degree of surgical resection control is not sufficient. Even using traditional lasers at this scale is impractical with a zone of damage >800 micrometers.

Figure 73:
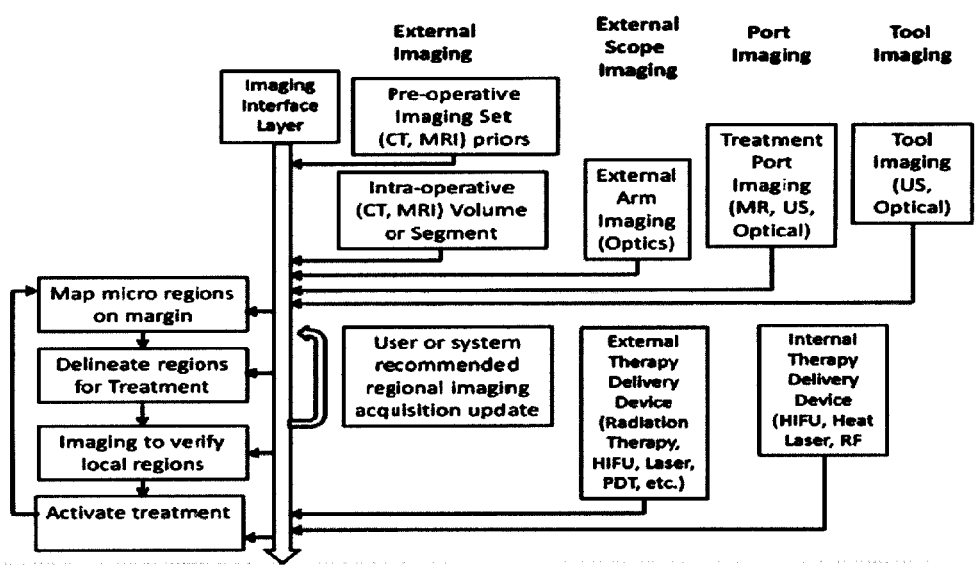
FIG. 73 shows a flowchart depicting the utilization of imaging data for tissue margin treatment.

FIG. 73 shows a flowchart depicting the utilization of imaging data for tissue margin treatment. This concept is shown in FIG. 73 where the addition of external therapy and internal therapy options are listed and included at the end of the procedure flow chart. In addition, this is presented in FIG. 74, where an external imaging, and laser ablative device 7402 is shown positioned above a tracked port 7404. The inner port surface in this case is immobilizing the tissue relative to the laser that is held in place by an external arm 7406.

Figure 74:
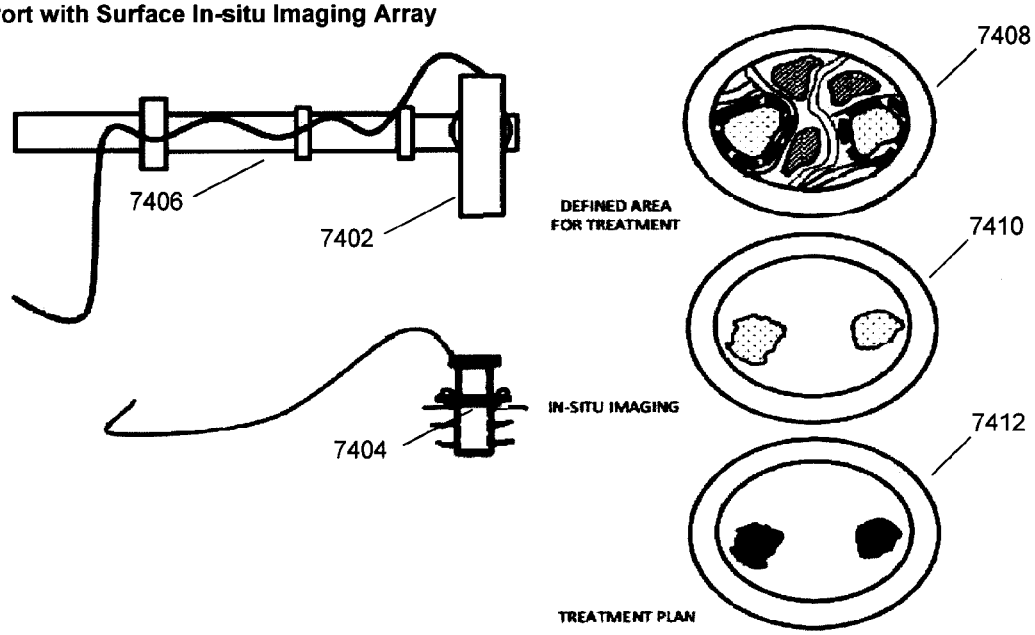
FIG. 74 is an illustration demonstrating an example port with a surface in-situ imaging array.

In FIG. 74, the external camera 7402 is showing a view down the port 7404 on the right with outlined regions 7414 defined by the surgeon in the top right view 7408. In the middle view 7410 standard threshold method may be applied to identify and segment area selected by the surgeon. This region may be imaged using a second imaging modality. In the bottom view 7412 is the calculated treatment plan as formulated by the treatment planning system, using the imaging, regions of interest, and surgeons input. In one embodiment the treatment planning system may compute area of interest to estimate the mass of the affected tissue. The mass of the tissue and a priori knowledge of therapy absorption properties of the tissue may be used to compute the treatment dose since dose is proportional to absorption rate of the therapy and mass of the tissue being treated. The therapy delivered may be selective tissue ablation delivered by a pico-second laser as described in "Tissue ablation with 100-fs and 200-ps laser pulses", Nishimura et al., Engineering in Medicine and Biology Society, 1998. Proceedings of the 20th Annual International Conference of the IEEE (Volume:4). This method avoids tissue charring and bubble formation. In another embodiment, the therapy delivered may be in the form of pharmaceuticals delivered directly to the exposed tissue region. The latter approach bypasses blood-brain barrier since the tissue is directly accessed via a port.

It is well understood that the more of the tumor volume is resected, the more effective secondary treatment strategies can be, to provide more localized cellular level therapy. These therapies include radiation therapy and chemotherapy. As with surgical approach, these therapies also follow the premise that the more healthy tissue is spared, the better the patient's recovery and longer-term functional outcomes. A fundamental limitation to this is the ability to do high resolution imaging at the margins of the tumor, and high-resolution therapy delivery in conjunction. Combining the two and delivering therapy in-vivo through a port device, provides surface access and imaging, the expected patient outcomes would be significantly improved.

Combining therapy and imaging in such a manner may be overcomes fundamental issues with plaguing therapy today: movement of tissue within body on the order of 2-5 mm from pulsatile flow, respiration limits fundamental therapy delivery; skull and sensitive brain tissue makes margins inaccessible; chemotherapies have been ineffective due to blood-brain barrier and non-selective killing mechanism; radiation therapy has been ineffective due to cell killing mechanism, inaccuracies of delivery, tissue differentiation, and collateral damage; high-frequency ultrasound cannot focus well through the brain; laser ablation cannot limit collateral damage; photodynamic therapy inability to access tissue, and tissue delivery through the blood-brain barrier.

By providing localized access to tissues of interest, and de-bulking the diseased tissue to a small region and depth through a multi-resolution imaging and resection approach, the problem of localized margin treatment can be more effectively managed in-vivo. In fact, the ability to administer imaging contrast agents, externally activated therapy agents, locally targeted biological agents, and local chemotherapy agents are available. The ability to use surface imaging techniques, particularly with external imaging sources such as the automated external imaging system, and specialized external laser ablative sources provides a means to treat residual disease at a level finer than a surgeon's scalpel.

8.7 Closure Verification

Figure 71:
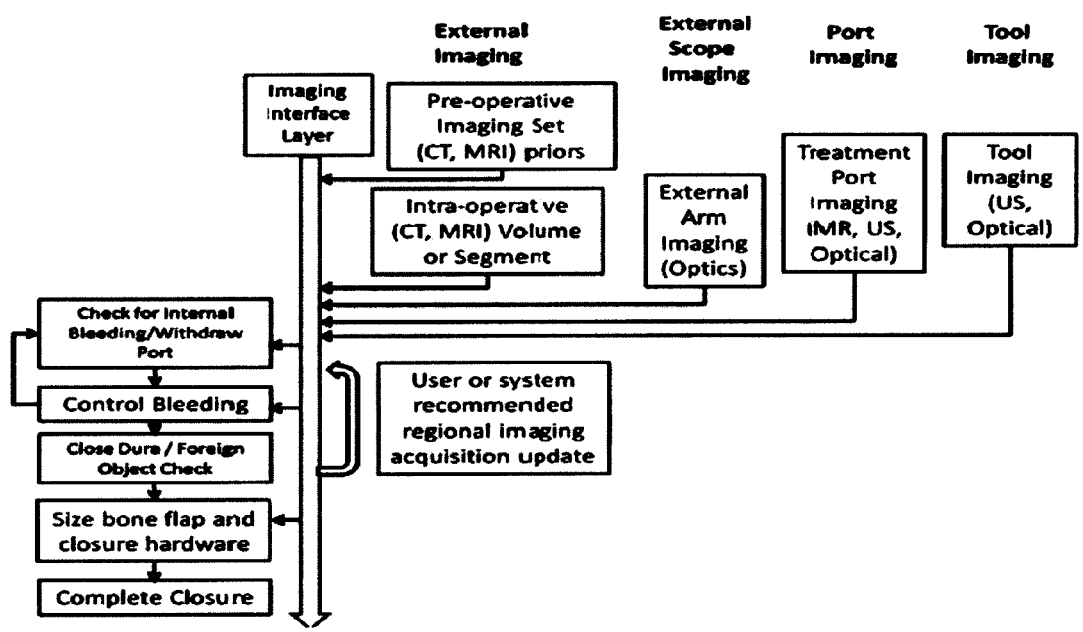
FIG. 71 shows a flowchart depicting the utilization of imaging data for surgical closure verification.

As a final verification that the surgery has been successfully performed, the same smaller field of view, and higher resolution imaging approach is performed in reverse as shown in FIG. 71. FIG. 71 shows a flowchart depicting the utilization of imaging data for surgical closure verification. Instead of focusing on smaller regions of interest as the surgeon de-bulks the tumor and addresses the margins, the port is withdrawn, and the surgeon images a larger and larger region of interest looking for residual tumor, un-controlled bleeding, excessive seepage, surgical object left in cavity, and recovery of the tissue next to the surgical cavity.

In some instances devices to assist in tissue recovery, such as chemotherapy delivery devices, or stem cell delivery devices may be left in the cavity, or in the sulcus folds of the brain. In the case of neuro-stimulation devices, the ability to image inside of the brain can enable predicting whether the anticipated surgical outcome will occur (for instance, Hall effect imaging with MRI, or local DTI to visualize nerve fiber integrity). Insert imaging may be done as the port is withdrawn, and after the dura is closed. Additional imaging may be used, in conjunction with navigation tip tracing, and external optical imaging, to define the appropriate geometry of bone flap and craniotomy closure hardware. A final scan may be required to validate there is no internal bleeding or excessive swelling after the surgeon has completed.

In some of the embodiments presented herein, an insert imaging device is provided that allows for image acquisition using one or more multiple modalities, and optionally the ability to acquire images at various resolutions. Such a device may enable the acquisition of images using one of the following possible configurations, (or combinations of configurations) through the surgical port:

1. Imaging of the distal end of the surgical port using an externally placed imaging device such as an external video scope, stand-off Raman sensor or hyper-spectral imager.

2. Imaging of the walls and the distal end of the surgical port through the use of sensors or sensor arrays placed in an insert in the port. This data may be used to construct 3D volume at high resolution due to proximal placement of sensors to areas of interest.

3. Image or analyze specific points on the exposed tissue located at the distal end of the port using touch sensors such as Raman probes, conductance measurement probes (or arrays), spectrometer-on-a-chip located at the tip of surgical tools or assay-based bio-chemical sensors. Any of the touch probes can be also tracked by attaching the touch probes, such as a Raman probe, to a holding assembly that also includes fiducial markers. Such tracking of the touch probe enables the association of measured data with exact location in the brain where such data was collected.

The device may be used in conjunction with therapeutic approaches, where the improved access afforded by the access port provides for better imaging, and better bi-manual access to the tissue and better therapeutic delivery. The therapeutic mechanism may be integrated into the insert imaging array, or located externally as shown in FIG. 74. Apart from energy-based therapeutic mechanisms, pharmaceuticals may be applied directly at the surgical region due to the availability of direct access.

Examples of surgical and therapeutic fields that may be impacted by the present disclosure include: imaging and navigation used in surgery; intraoperative tumor removal and critical structure detection; accessing brain regions via the skull base, removal of deep seeded tumors and stem cell detection; placement of probes and devices for deep brain stimulation, shunts, implantable devices; vascular brain defect surgery, Intra-cerebral hemorrhage (ICH); surgical procedures to address neurodegenerative disease (Parkinson's, Alzheimer's, Huntington's, Dystonia, Major Depression, OCD, Epilepsy, Brain Tumor); and access to inner brain regions via various access ports to the brain.

8.8 Robotic Positioning

It is to be noted that at each stage of the surgery where guidance of devices, instruments, lasers, or surgical tools are performed, the means of delivery and guidance of said devices may be performed by a human operator, a human-assisted robotic delivery, or a closed loop robotic guidance/delivery of the instruments. The insert imaging array concept can be utilized to augment robotic, or semi-automatic delivery of tools by way of improved dynamic imaging, and/or static imaging with immobilization. Examples of robotic positioning systems and methods are provided in PCT Patent Application No. PCT/CA2014/######, titled "SYSTEMS AND METHODS FOR INTELLIGENT POSITIONING OF DEVICES DURING A MEDICAL PROCEDURE" and filed on Mar. 14, 2014, the entire contents of which is incorporated herein by reference.

8.9 Surgical Workflow (Methods)

The utility of the present disclosure may be employed at a multitude of stages of surgical intervention. While pre-operative imaging is used to guide the decision on incision location, local imaging is used to guide the port along the sulci. This may be realized through ultrasound, MR, or OCT imaging modalities. Such images help identify potential risk of deviating from the sulci and potentially severing nerve bundles. The surgical region of interest may be identified through any of the tissue differentiation modalities such as MR, OCT, ultrasound and Raman spectroscopy. The diseased tissue is then de-bulked and any bleeding may be managed by preventing the excess fluid from occluding the image. Impact of glare and excessive fluid in the image can be minimized through selective filtering achieved through Hyper-spectral imaging, NIR imaging and OCT.

Subsequent to de-bulking of tumor mass, selective regions may be identified through probe-based Raman spectroscopy or assay-based chemiluminescence achieved through the use of appropriate chemical probes at the distal portion of the insert component in the port. Presence of healthy tissue margin after resection of tumor may be confirmed through the use of bio-electric sensors located at the distal portion of the insert probe. Upon confirmation that all tumor regions have been removed, the port may be closed and external video scope based imaging may be used to check for bleeding immediately below the dermis.

In FIGS. 68 to 73, the steps of the surgical procedure, as well as iterative components, such as re-imaging when tumor or tissue is removed, bleeding is needed to be surgically controlled, when surgical margins need to be interrogated, or the iterative process of moving the port to a new area for interrogation or tissue resection is performed. Shown on the right side of the flow chart are the instances where external Imaging (either pre-operative, intra-operative), external scope imaging, port imaging (either at surface or inserted into the brain), or tool based imaging may be used. The imaging modalities previously presented may be utilized in different combinations as appropriate for the task at hand. The arrows represent where the imaging information is included into the procedure, and the "Imaging Interface Layer" identified with a vertical arrow, represents a software and hardware configuration that integrates the imaging into a representation that can be utilized by the surgeon to assist in the procedure steps represented on the left of the figures above. The image sets may be simply represented as 2D or 3D representations on a single, or multiple screens, or fused together spatially, or temporally. When imaging sets are registered, either by way of mutual information, such as gradient changes in the data (image or frequency space), or by registration of common quantifiable contrast mechanisms (i.e. stiffness (elastic modulus), density, anisotropy, etc.), the data sets may be super-imposed, or one data-set can be used to morph the other data set to the same spatial coordinate frame (i.e. shift in tissue, or tissue being removed), or same temporal frame (i.e. imaging taken at different time). The software system can calculate similarity metrics between registered sets, and suggested to the user that additional imaging sets are required, as the prior sets (taken pre-surgically, or earlier in the procedure), are no longer representative of the current state of the tissue during that stage of the procedure. This concept can be extended to control robotic manipulators, such that if the system determines the imaging data to fall outside of a particular threshold for a similarity metric, the system will not allow the robotic system to operate autonomously, or will required user interaction.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A magnetic resonance imaging probe comprising:
  a longitudinal body;
  first, second and third magnetic resonance coils supported by said longitudinal body;
  wherein said first coil is configured to measure fields having a first direction within a region of interest beyond a distal end of said longitudinal body;
  said first coil comprising:
    one or more magnetic resonance coils housed within said longitudinal body, wherein at least one coil is a folded stripline coil comprising:
      two longitudinal stripline conductors having a ground plane conductor provided therebetween;
      a folded conductor segment connecting said two longitudinal stripline conductors near a distal portion of said longitudinal body;
  wherein said second coil is configured to measure fields having a second direction within a region of interest beyond the distal end of said longitudinal body, wherein said first direction and said second direction are approximately orthogonal;
  said second coil comprising:
    an additional folded stripline coil comprising:
    additional longitudinal stripline conductors oriented having said ground plane conductor provided therebetween; and
    an additional folded conductor segment connecting said two additional longitudinal stripline conductors near said distal portion of said longitudinal body;
    wherein said two additional longitudinal stripline conductors are oriented such that said folded conductor segment and said additional folded conductor segment are approximately orthogonal, thereby forming a folded stripline quadrature pair;
  wherein said third coil is configured to measure fields having a third direction within the region of interest beyond said distal end of said longitudinal body, wherein said third direction is approximately orthogonal to said first direction and said second direction;
  said third coil comprising:
    a coil loop provided near said distal portion of said longitudinal body, said coil loop having a coil axis that is approximately parallel to a longitudinal axis of said longitudinal body;
  electrical circuits housed within said longitudinal body for tuning and matching said first, second and third coils and preamplifying signals detected by said first, second, and third coils;
  said electrical circuits comprising:
    a pair of matching capacitors, each matching capacitor provided between one of said longitudinal stripline conductors and said ground plane conductor;
    a tuning capacitor serially provided within one of said longitudinal stripline conductors;
    a preamplifier circuit housed within said longitudinal body, wherein said preamplifier circuit is operatively coupled to said folded stripline coil;
    a pair of additional matching capacitors, each additional matching capacitor provided between one of said additional longitudinal stripline conductors and said ground plane conductor; and
    an additional preamplifier circuit housed within said longitudinal body, wherein said additional preamplifier circuit is operatively coupled to said additional folded stripline coil.

2. A magnetic resonance imaging probe comprising:
  a longitudinal body;
  first, second and third magnetic resonance coils supported by said longitudinal body;
  wherein said first coil is configured to measure fields having a first direction within a region of interest beyond a distal end of said longitudinal body;
  said first coil comprising:
    one or more magnetic resonance coils housed within said longitudinal body, wherein at least one coil is a folded stripline coil comprising:
      two longitudinal stripline conductors having a ground plane conductor provided therebetween;
      a folded conductor segment connecting said two longitudinal stripline conductors near a distal portion of said longitudinal body;
  wherein said second coil is configured to measure fields having a second direction within a region of interest beyond the distal end of said longitudinal body, wherein said first direction and said second direction are approximately orthogonal;

said second coil comprising:
an additional folded stripline coil comprising:
additional longitudinal stripline conductors oriented having said ground plane conductor provided therebetween; and
an additional folded conductor segment connecting said two additional longitudinal stripline conductors near said distal portion of said longitudinal body;
wherein said two additional longitudinal stripline conductors are oriented such that said folded conductor segment and said additional folded conductor segment are approximately orthogonal, thereby forming a folded stripline quadrature pair;

wherein said third coil is configured to measure fields having a third direction within the region of interest beyond said distal end of said longitudinal body, wherein said third direction is approximately orthogonal to said first direction and said second direction;

said third coil comprising:
a coil loop provided near said distal portion of said longitudinal body, said coil loop having a coil axis that is approximately parallel to a longitudinal axis of said longitudinal body;

electrical circuits housed within said longitudinal body for tuning and matching said first, second and third coils and preamplifying signals detected by said first, second, and third coils;

said electrical circuits comprising:
a pair of matching capacitors, each matching capacitor provided between one of said longitudinal stripline conductors and said ground plane conductor;
a tuning capacitor serially provided within one of said longitudinal stripline conductors;
a preamplifier circuit housed within said longitudinal body, wherein said preamplifier circuit is operatively coupled to said folded stripline coil;
a pair of additional matching capacitors, each additional matching capacitor provided between one of said additional longitudinal stripline conductors and said ground plane conductor; and
an additional preamplifier circuit housed within said longitudinal body, wherein said additional preamplifier circuit is operatively coupled to said additional folded stripline coil;

an access port; and the claimed magnetic resonance imaging probe, wherein said longitudinal body is a cylindrical body portion configured to be slidably and removably inserted within an inner lumen of said access port.

3. The magnetic resonance imaging probe according to claim 2 further comprising
one or more air passage features provided on or with said cylindrical body portion for facilitating expulsion of air from the inner lumen of the access port during insertion of said cylindrical body portion into the access port.

4. The magnetic resonance imaging probe according to claim 3 wherein said one or more air passages comprise one or more grooves formed within an outer surface of said cylindrical body portion.

5. The magnetic resonance imaging probe according to claim 3 wherein said cylindrical body portion is formed from a material having a magnetic susceptibility approximately equal to that of water.

* * * * *